US011603554B2

(12) United States Patent
Belgrader et al.

(10) Patent No.: US 11,603,554 B2
(45) Date of Patent: *Mar. 14, 2023

(54) PARTITION PROCESSING METHODS AND SYSTEMS

(71) Applicant: 10X Genomics, Inc., Pleasanton, CA (US)

(72) Inventors: Phillip Belgrader, Livermore, CA (US); Donald A. Masquelier, Tracy, CA (US)

(73) Assignee: 10x Genomics, Inc., Pleasanton, CA (US)

(*) Notice: Subject to any disclaimer, the term of this patent is extended or adjusted under 35 U.S.C. 154(b) by 421 days.

This patent is subject to a terminal disclaimer.

(21) Appl. No.: 16/913,084

(22) Filed: Jun. 26, 2020

(65) Prior Publication Data

US 2021/0032678 A1 Feb. 4, 2021

Related U.S. Application Data

(63) Continuation of application No. 15/050,948, filed on Feb. 23, 2016, now Pat. No. 10,697,000.

(60) Provisional application No. 62/119,930, filed on Feb. 24, 2015.

(51) Int. Cl.
| | | |
|---|---|---|
| *C12Q 1/6806* | (2018.01) | |
| *C12N 15/10* | (2006.01) | |
| *C12Q 1/6869* | (2018.01) | |
| *G01N 1/34* | (2006.01) | |
| *G01N 1/40* | (2006.01) | |

(52) U.S. Cl.
CPC ....... *C12Q 1/6806* (2013.01); *C12N 15/1006* (2013.01); *C12N 15/1013* (2013.01); *C12Q 1/6869* (2013.01); *G01N 1/34* (2013.01); *G01N 1/405* (2013.01); *G01N 2001/4038* (2013.01)

(58) Field of Classification Search
CPC ............. C12Q 1/6806; C12Q 1/6869; C12Q 2563/143; C12Q 2563/149; C12Q 2563/179; C12Q 2565/629; C12N 15/1006; C12N 15/1013; G01N 1/34; G01N 1/405; G01N 2001/4038
See application file for complete search history.

(56) References Cited

U.S. PATENT DOCUMENTS

| | | | |
|---|---|---|---|
| 2,797,149 A | 6/1957 | Skeggs | |
| 3,047,367 A | 7/1962 | Kessler | |
| 3,479,141 A | 11/1969 | Smythe et al. | |
| 4,124,638 A | 11/1978 | Hansen | |
| 4,253,846 A | 3/1981 | Smythe et al. | |
| 4,582,802 A | 4/1986 | Zimmerman et al. | |
| 4,895,650 A * | 1/1990 | Wang | B01L 9/06 422/561 |
| 5,137,829 A | 8/1992 | Nag et al. | |
| 5,149,625 A | 9/1992 | Church et al. | |
| 5,185,099 A | 2/1993 | Delpuech et al. | |
| 5,202,231 A | 4/1993 | Drmanac et al. | |
| 5,270,183 A | 12/1993 | Corbett et al. | |
| 5,413,924 A | 5/1995 | Kosak et al. | |
| 5,418,149 A | 5/1995 | Gelfand et al. | |
| 5,436,130 A | 7/1995 | Mathies et al. | |
| 5,478,893 A | 12/1995 | Ghosh et al. | |
| 5,489,523 A | 2/1996 | Mathur | |
| 5,512,131 A | 4/1996 | Kumar et al. | |
| 5,558,071 A | 9/1996 | Ward et al. | |
| 5,585,069 A | 12/1996 | Zanzucchi et al. | |
| 5,587,128 A | 12/1996 | Wilding et al. | |
| 5,605,793 A | 2/1997 | Stemmer | |
| 5,618,711 A | 4/1997 | Gelfand et al. | |
| 5,658,548 A | 8/1997 | Padhye et al. | |
| 5,695,940 A | 12/1997 | Drmanac et al. | |
| 5,700,642 A | 12/1997 | Monforte et al. | |
| 5,705,628 A | 1/1998 | Hawkins | |
| 5,708,153 A | 1/1998 | Dower et al. | |
| 5,736,330 A | 4/1998 | Fulton | |
| 5,739,036 A | 4/1998 | Parris | |
| 5,744,311 A | 4/1998 | Fraiser et al. | |
| 5,756,334 A | 5/1998 | Perler et al. | |
| 5,830,663 A | 11/1998 | Embleton et al. | |
| 5,834,197 A | 11/1998 | Parton | |
| 5,842,787 A | 12/1998 | Kopf-Sill et al. | |
| 5,846,719 A | 12/1998 | Brenner et al. | |
| 5,846,727 A | 12/1998 | Soper et al. | |
| 5,851,769 A | 12/1998 | Gray et al. | |
| 5,856,174 A | 1/1999 | Lipshutz et al. | |
| 5,872,010 A | 2/1999 | Karger et al. | |
| 5,897,783 A | 4/1999 | Howe et al. | |
| 5,900,481 A | 5/1999 | Lough et al. | |

(Continued)

FOREIGN PATENT DOCUMENTS

| | | |
|---|---|---|
| CN | 102292455 A | 12/2011 |
| CN | 103202812 A | 7/2013 |
| EP | 0249007 A2 | 12/1987 |
| EP | 0271281 A2 | 6/1988 |
| EP | 0637996 B1 | 7/1997 |
| EP | 1019496 B1 | 9/2004 |
| EP | 1672064 A1 | 6/2006 |
| EP | 1482036 B1 | 10/2007 |
| EP | 1841879 A2 | 10/2007 |
| EP | 1944368 A1 | 7/2008 |

(Continued)

OTHER PUBLICATIONS

Burger et al, Novel Automated Blood Separations Validate Whole Cell Biomarkers, 2011, 6, e22430, pp. 1-11 (Year: 2011).*

(Continued)

*Primary Examiner* — Narayan K Bhat
(74) *Attorney, Agent, or Firm* — Clark & Elbing LLP

(57) ABSTRACT

The disclosure provides methods for separating and/or purifying one or more molecules released from one or more fluid compartments or partitions, such as one or more droplets. Molecules can be released from a fluid compartment(s) and bound to supports that can be isolated via any suitable method, including example methods described herein. The disclosure also provides devices that can aid in isolating supports bound to molecules.

20 Claims, 11 Drawing Sheets

(56) References Cited

U.S. PATENT DOCUMENTS

| | | |
|---|---|---|
| 5,942,609 A | 8/1999 | Hunkapiller et al. |
| 5,958,703 A | 9/1999 | Dower et al. |
| 5,965,443 A | 10/1999 | Reznikoff et al. |
| 5,994,056 A | 11/1999 | Higuchi |
| 5,997,636 A | 12/1999 | Gamarnik et al. |
| 6,033,880 A | 3/2000 | Haff et al. |
| 6,046,003 A | 4/2000 | Mandecki |
| 6,051,377 A | 4/2000 | Mandecki |
| 6,057,107 A | 5/2000 | Fulton |
| 6,057,149 A | 5/2000 | Burns et al. |
| 6,103,537 A | 8/2000 | Ullman et al. |
| 6,110,678 A | 8/2000 | Weisburg et al. |
| 6,123,798 A | 9/2000 | Gandhi et al. |
| 6,133,436 A | 10/2000 | Koster et al. |
| 6,143,496 A | 11/2000 | Brown et al. |
| 6,159,717 A | 12/2000 | Savakis et al. |
| 6,171,850 B1 | 1/2001 | Nagle et al. |
| 6,172,218 B1 | 1/2001 | Brenner |
| 6,207,384 B1 | 3/2001 | Mekalanos et al. |
| 6,258,571 B1 | 7/2001 | Chumakov et al. |
| 6,265,552 B1 | 7/2001 | Schatz |
| 6,291,243 B1 | 9/2001 | Fogarty et al. |
| 6,294,385 B1 | 9/2001 | Goryshin et al. |
| 6,296,020 B1 | 10/2001 | McNeely et al. |
| 6,297,006 B1 | 10/2001 | Drmanac et al. |
| 6,297,017 B1 | 10/2001 | Schmidt et al. |
| 6,303,343 B1 | 10/2001 | Kopf-Sill |
| 6,306,590 B1 | 10/2001 | Mehta et al. |
| 6,327,410 B1 | 12/2001 | Walt et al. |
| 6,355,198 B1 | 3/2002 | Kim et al. |
| 6,361,950 B1 | 3/2002 | Mandecki |
| 6,372,813 B1 | 4/2002 | Johnson et al. |
| 6,379,929 B1 | 4/2002 | Burns et al. |
| 6,406,848 B1 | 6/2002 | Bridgham et al. |
| 6,409,832 B2 | 6/2002 | Weigl et al. |
| 6,432,290 B1 | 8/2002 | Harrison et al. |
| 6,432,360 B1 | 8/2002 | Church |
| 6,485,944 B1 | 11/2002 | Church et al. |
| 6,492,118 B1 | 12/2002 | Abrams et al. |
| 6,511,803 B1 | 1/2003 | Church et al. |
| 6,524,456 B1 | 2/2003 | Ramsey et al. |
| 6,569,631 B1 | 5/2003 | Pantoliano et al. |
| 6,579,851 B2 | 6/2003 | Goeke et al. |
| 6,586,176 B1 | 7/2003 | Trnovsky et al. |
| 6,593,113 B1 | 7/2003 | Tenkanen et al. |
| 6,613,752 B2 | 9/2003 | Kay et al. |
| 6,632,606 B1 | 10/2003 | Ullman et al. |
| 6,632,655 B1 | 10/2003 | Mehta et al. |
| 6,670,133 B2 | 12/2003 | Knapp et al. |
| 6,723,513 B2 | 4/2004 | Lexow |
| 6,767,731 B2 | 7/2004 | Hannah |
| 6,800,298 B1 | 10/2004 | Burdick et al. |
| 6,806,052 B2 | 10/2004 | Bridgham et al. |
| 6,806,058 B2 | 10/2004 | Jesperson et al. |
| 6,859,570 B2 | 2/2005 | Walt et al. |
| 6,880,576 B2 | 4/2005 | Karp et al. |
| 6,884,788 B2 | 4/2005 | Bulpitt et al. |
| 6,913,935 B1 | 7/2005 | Thomas |
| 6,929,859 B2 | 8/2005 | Chandler et al. |
| 6,969,488 B2 | 11/2005 | Bridgham et al. |
| 6,974,669 B2 | 12/2005 | Mirkin et al. |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,138,267 B1 | 11/2006 | Jendrisak et al. |
| 7,211,654 B2 | 5/2007 | Gao et al. |
| 7,262,056 B2 | 8/2007 | Wooddell et al. |
| 7,268,167 B2 | 9/2007 | Higuchi et al. |
| 7,282,370 B2 | 10/2007 | Bridgham et al. |
| 7,294,503 B2 | 11/2007 | Quake et al. |
| 7,297,485 B2 | 11/2007 | Bornarth et al. |
| 7,316,903 B2 | 1/2008 | Yanagihara et al. |
| 7,323,305 B2 | 1/2008 | Leamon et al. |
| 7,329,493 B2 | 2/2008 | Chou et al. |
| 7,425,431 B2 | 9/2008 | Church et al. |
| 7,536,928 B2 | 5/2009 | Kazuno |
| 7,544,473 B2 | 6/2009 | Brenner |
| 7,604,938 B2 | 10/2009 | Takahashi et al. |
| 7,608,434 B2 | 10/2009 | Reznikoff et al. |
| 7,608,451 B2 | 10/2009 | Cooper et al. |
| 7,622,280 B2 | 11/2009 | Holliger et al. |
| 7,638,276 B2 | 12/2009 | Griffiths et al. |
| 7,645,596 B2 | 1/2010 | Williams et al. |
| 7,666,664 B2 | 2/2010 | Sarofim et al. |
| 7,700,325 B2 | 4/2010 | Cantor et al. |
| 7,708,949 B2 | 5/2010 | Stone et al. |
| 7,709,197 B2 | 5/2010 | Drmanac |
| 7,718,421 B2 | 5/2010 | Chen et al. |
| 7,745,178 B2 | 6/2010 | Dong |
| 7,745,218 B2 | 6/2010 | Kim et al. |
| 7,776,927 B2 | 8/2010 | Chu et al. |
| RE41,780 E | 9/2010 | Anderson et al. |
| 7,799,553 B2 | 9/2010 | Mathies et al. |
| 7,842,457 B2 | 11/2010 | Berka et al. |
| 7,901,891 B2 | 3/2011 | Drmanac |
| 7,910,354 B2 | 3/2011 | Drmanac et al. |
| 7,947,477 B2 | 5/2011 | Schroeder |
| 7,960,104 B2 | 6/2011 | Drmanac et al. |
| 7,968,287 B2 | 6/2011 | Griffiths et al. |
| 7,972,778 B2 | 7/2011 | Brown et al. |
| 8,003,312 B2 | 8/2011 | Krutzik et al. |
| 8,008,018 B2 | 8/2011 | Quake et al. |
| 8,053,192 B2 | 11/2011 | Bignell et al. |
| 8,067,159 B2 | 11/2011 | Brown et al. |
| 8,101,346 B2 | 1/2012 | Takahama |
| 8,124,404 B2 | 2/2012 | Alphey |
| 8,133,719 B2 | 3/2012 | Drmanac et al. |
| 8,137,563 B2 | 3/2012 | Ma et al. |
| 8,168,385 B2 | 5/2012 | Brenner |
| 8,252,539 B2 | 8/2012 | Quake et al. |
| 8,268,564 B2 | 9/2012 | Roth et al. |
| 8,273,573 B2 | 9/2012 | Ismagilov et al. |
| 8,278,071 B2 | 10/2012 | Brown et al. |
| 8,298,767 B2 | 10/2012 | Brenner et al. |
| 8,304,193 B2 | 11/2012 | Ismagilov et al. |
| 8,318,433 B2 | 11/2012 | Brenner |
| 8,318,460 B2 | 11/2012 | Cantor et al. |
| 8,329,407 B2 | 12/2012 | Ismagilov et al. |
| 8,337,778 B2 | 12/2012 | Stone et al. |
| 8,361,299 B2 | 1/2013 | Sabin et al. |
| 8,420,386 B2 | 4/2013 | Ivies et al. |
| 8,461,129 B2 | 6/2013 | Bolduc et al. |
| 8,563,274 B2 | 10/2013 | Brenner et al. |
| 8,592,150 B2 | 11/2013 | Drmanac et al. |
| 8,598,328 B2 | 12/2013 | Koga et al. |
| 8,603,749 B2 | 12/2013 | Gillevet |
| 8,679,756 B1 | 3/2014 | Brenner et al. |
| 8,748,094 B2 | 6/2014 | Weitz et al. |
| 8,748,102 B2 | 6/2014 | Berka et al. |
| 8,765,380 B2 | 7/2014 | Berka et al. |
| 8,822,148 B2 | 9/2014 | Ismagilov et al. |
| 8,829,171 B2 | 9/2014 | Steemers et al. |
| 8,835,358 B2 | 9/2014 | Fodor et al. |
| 8,871,444 B2 | 10/2014 | Griffiths et al. |
| 8,889,083 B2 | 11/2014 | Ismagilov et al. |
| 8,927,218 B2 | 1/2015 | Forsyth |
| 8,975,302 B2 | 3/2015 | Light et al. |
| 8,986,286 B2 | 3/2015 | Tanghoej et al. |
| 8,986,628 B2 | 3/2015 | Stone et al. |
| 9,005,935 B2 | 4/2015 | Belyaev |
| 9,012,390 B2 | 4/2015 | Holtze et al. |
| 9,017,948 B2 | 4/2015 | Agresti et al. |
| 9,029,083 B2 | 5/2015 | Griffiths et al. |
| 9,029,085 B2 | 5/2015 | Agresti et al. |
| 9,040,256 B2 | 5/2015 | Grunenwald et al. |
| 9,068,210 B2 | 6/2015 | Agresti et al. |
| 9,074,251 B2 | 7/2015 | Steemers et al. |
| 9,080,211 B2 | 7/2015 | Grunenwald et al. |
| 9,102,980 B2 | 8/2015 | Brenner et al. |
| 9,150,916 B2 | 10/2015 | Christen et al. |
| 9,175,295 B2 | 11/2015 | Kaminaka et al. |
| 9,238,671 B2 | 1/2016 | Goryshin et al. |
| 9,249,460 B2 | 2/2016 | Pushkarev et al. |
| 9,273,349 B2 | 3/2016 | Nguyen et al. |

(56) References Cited

U.S. PATENT DOCUMENTS

| | | |
|---|---|---|
| 9,290,808 B2 | 3/2016 | Fodor et al. |
| 9,328,382 B2 | 5/2016 | Drmanac et al. |
| 9,347,056 B2 | 5/2016 | Saito et al. |
| 9,347,059 B2 | 5/2016 | Saxonov |
| 9,388,465 B2 | 7/2016 | Hindson et al. |
| 9,410,201 B2 | 8/2016 | Hindson et al. |
| 9,436,088 B2 | 9/2016 | Seul et al. |
| 9,567,631 B2 | 2/2017 | Hindson et al. |
| 9,574,226 B2 | 2/2017 | Gormley et al. |
| 9,637,799 B2 | 5/2017 | Fan et al. |
| 9,644,204 B2 | 5/2017 | Hindson et al. |
| 9,689,024 B2 | 6/2017 | Hindson et al. |
| 9,694,361 B2 | 7/2017 | Bharadwaj et al. |
| 9,695,468 B2 | 7/2017 | Hindson et al. |
| 9,701,998 B2 | 7/2017 | Hindson et al. |
| 9,856,530 B2 | 1/2018 | Hindson et al. |
| 9,951,386 B2 | 4/2018 | Hindson et al. |
| 9,957,558 B2 | 5/2018 | Leamon et al. |
| 10,011,872 B1 | 7/2018 | Belgrader et al. |
| 10,017,759 B2 | 7/2018 | Kaper et al. |
| 10,030,267 B2 | 7/2018 | Hindson et al. |
| 10,041,116 B2 | 8/2018 | Hindson et al. |
| 10,053,723 B2 | 8/2018 | Hindson et al. |
| 10,059,989 B2 | 8/2018 | Giresi et al. |
| 10,071,377 B2 | 9/2018 | Bharadwaj et al. |
| 10,119,167 B2 | 11/2018 | Srinivasan et al. |
| 10,137,449 B2 | 11/2018 | Bharadwaj et al. |
| 10,144,950 B2 | 12/2018 | Nolan |
| 10,150,117 B2 | 12/2018 | Bharadwaj et al. |
| 10,150,963 B2 | 12/2018 | Hindson et al. |
| 10,150,964 B2 | 12/2018 | Hindson et al. |
| 10,150,995 B1 | 12/2018 | Giresi et al. |
| 10,174,310 B2 | 1/2019 | Nolan |
| 10,208,343 B2 | 2/2019 | Hindson et al. |
| 10,221,436 B2 | 3/2019 | Hardenbol et al. |
| 10,221,442 B2 | 3/2019 | Hindson et al. |
| 10,227,648 B2 | 3/2019 | Hindson et al. |
| 10,253,364 B2 | 4/2019 | Hindson et al. |
| 10,273,541 B2 | 4/2019 | Hindson et al. |
| 10,441,957 B2 * | 10/2019 | Park .................. B01L 9/06 |
| 10,697,000 B2 | 6/2020 | Belgrader et al. |
| 2001/0020588 A1 | 9/2001 | Adourian et al. |
| 2001/0036669 A1 | 11/2001 | Jedrzejewski et al. |
| 2001/0041357 A1 | 11/2001 | Fouillet et al. |
| 2001/0044109 A1 | 11/2001 | Mandecki |
| 2001/0048900 A1 | 12/2001 | Bardell et al. |
| 2001/0053519 A1 | 12/2001 | Fodor et al. |
| 2002/0001856 A1 | 1/2002 | Chow et al. |
| 2002/0005354 A1 | 1/2002 | Spence et al. |
| 2002/0034737 A1 | 3/2002 | Drmanac |
| 2002/0043463 A1 | 4/2002 | Shenderov |
| 2002/0051971 A1 | 5/2002 | Stuelpnagel et al. |
| 2002/0051992 A1 | 5/2002 | Bridgham et al. |
| 2002/0058332 A1 | 5/2002 | Quake et al. |
| 2002/0065609 A1 | 5/2002 | Ashby |
| 2002/0068278 A1 | 6/2002 | Giese et al. |
| 2002/0089100 A1 | 7/2002 | Kawasaki |
| 2002/0092767 A1 | 7/2002 | Bjornson et al. |
| 2002/0113009 A1 | 8/2002 | O'Connor et al. |
| 2002/0119455 A1 | 8/2002 | Chan |
| 2002/0119536 A1 | 8/2002 | Stern |
| 2002/0131147 A1 | 9/2002 | Paolini et al. |
| 2002/0160518 A1 | 10/2002 | Hayenga et al. |
| 2002/0164820 A1 | 11/2002 | Brown |
| 2002/0166582 A1 | 11/2002 | O'Connor et al. |
| 2002/0172965 A1 | 11/2002 | Kamb et al. |
| 2002/0175079 A1 | 11/2002 | Christel et al. |
| 2002/0179849 A1 | 12/2002 | Maher et al. |
| 2003/0005967 A1 | 1/2003 | Karp |
| 2003/0007898 A1 | 1/2003 | Bohm et al. |
| 2003/0008285 A1 | 1/2003 | Fischer |
| 2003/0008323 A1 | 1/2003 | Ravkin et al. |
| 2003/0022231 A1 | 1/2003 | Wangh et al. |
| 2003/0027203 A1 | 2/2003 | Fields |
| 2003/0027214 A1 | 2/2003 | Kamb |
| 2003/0027221 A1 | 2/2003 | Scott et al. |
| 2003/0028981 A1 | 2/2003 | Chandler et al. |
| 2003/0032141 A1 | 2/2003 | Nguyen et al. |
| 2003/0036206 A1 | 2/2003 | Chien et al. |
| 2003/0039978 A1 | 2/2003 | Hannah |
| 2003/0044777 A1 | 3/2003 | Beattie |
| 2003/0044836 A1 | 3/2003 | Levine et al. |
| 2003/0075446 A1 | 4/2003 | Culbertson et al. |
| 2003/0082587 A1 | 5/2003 | Seul et al. |
| 2003/0089605 A1 | 5/2003 | Timperman |
| 2003/0104466 A1 | 6/2003 | Knapp et al. |
| 2003/0108897 A1 | 6/2003 | Drmanac |
| 2003/0124509 A1 | 7/2003 | Kenis et al. |
| 2003/0149307 A1 | 8/2003 | Hai et al. |
| 2003/0170698 A1 | 9/2003 | Gascoyne et al. |
| 2003/0182068 A1 | 9/2003 | Battersby et al. |
| 2003/0207260 A1 | 11/2003 | Trnovsky et al. |
| 2003/0215862 A1 | 11/2003 | Parce et al. |
| 2004/0040851 A1 | 3/2004 | Karger et al. |
| 2004/0063138 A1 | 4/2004 | McGinnis et al. |
| 2004/0081962 A1 | 4/2004 | Chen et al. |
| 2004/0101680 A1 | 5/2004 | Barber |
| 2004/0101880 A1 | 5/2004 | Rozwadowski et al. |
| 2004/0132122 A1 | 7/2004 | Banerjee et al. |
| 2004/0214175 A9 | 10/2004 | McKernan et al. |
| 2004/0224331 A1 | 11/2004 | Cantor et al. |
| 2004/0258701 A1 | 12/2004 | Dominowski et al. |
| 2005/0013741 A1 | 1/2005 | a' Brassard |
| 2005/0019839 A1 | 1/2005 | Jespersen et al. |
| 2005/0042625 A1 | 2/2005 | Schmidt et al. |
| 2005/0079510 A1 | 4/2005 | Berka et al. |
| 2005/0130188 A1 | 6/2005 | Walt et al. |
| 2005/0172476 A1 | 8/2005 | Stone et al. |
| 2005/0181379 A1 | 8/2005 | Su et al. |
| 2005/0202429 A1 | 9/2005 | Trau et al. |
| 2005/0202489 A1 | 9/2005 | Cho et al. |
| 2005/0221339 A1 | 10/2005 | Griffiths et al. |
| 2005/0244850 A1 | 11/2005 | Huang et al. |
| 2005/0272159 A1 | 12/2005 | Ismagilov et al. |
| 2005/0287572 A1 | 12/2005 | Mathies et al. |
| 2006/0002890 A1 | 1/2006 | Hersel et al. |
| 2006/0008799 A1 | 1/2006 | Cai et al. |
| 2006/0020371 A1 | 1/2006 | Ham et al. |
| 2006/0040382 A1 | 2/2006 | Heffron et al. |
| 2006/0073487 A1 | 4/2006 | Oliver et al. |
| 2006/0078888 A1 | 4/2006 | Griffiths et al. |
| 2006/0153924 A1 | 7/2006 | Griffiths et al. |
| 2006/0163385 A1 | 7/2006 | Link et al. |
| 2006/0177832 A1 | 8/2006 | Brenner |
| 2006/0177833 A1 | 8/2006 | Brenner |
| 2006/0199193 A1 | 9/2006 | Koo et al. |
| 2006/0240506 A1 | 10/2006 | Kushmaro et al. |
| 2006/0257893 A1 | 11/2006 | Takahashi et al. |
| 2006/0263888 A1 | 11/2006 | Fritz et al. |
| 2006/0275782 A1 | 12/2006 | Gunderson et al. |
| 2006/0286570 A1 | 12/2006 | Rowlen et al. |
| 2006/0292583 A1 | 12/2006 | Schneider et al. |
| 2007/0003442 A1 | 1/2007 | Link et al. |
| 2007/0020617 A1 | 1/2007 | Trnovsky et al. |
| 2007/0020640 A1 | 1/2007 | McCloskey et al. |
| 2007/0026401 A1 | 2/2007 | Hofmann et al. |
| 2007/0031829 A1 | 2/2007 | Yasuno et al. |
| 2007/0042400 A1 | 2/2007 | Choi et al. |
| 2007/0042419 A1 | 2/2007 | Barany et al. |
| 2007/0054119 A1 | 3/2007 | Garstecki et al. |
| 2007/0072208 A1 | 3/2007 | Drmanac |
| 2007/0077572 A1 | 4/2007 | Tawfik et al. |
| 2007/0092914 A1 | 4/2007 | Griffiths et al. |
| 2007/0099208 A1 | 5/2007 | Drmanac et al. |
| 2007/0134277 A1 | 6/2007 | Chen et al. |
| 2007/0141584 A1 | 6/2007 | Roberts et al. |
| 2007/0154903 A1 | 7/2007 | Marla et al. |
| 2007/0160503 A1 | 7/2007 | Sethu et al. |
| 2007/0172873 A1 | 7/2007 | Brenner et al. |
| 2007/0190543 A1 | 8/2007 | Livak |
| 2007/0195127 A1 | 8/2007 | Ahn et al. |
| 2007/0207060 A1 | 9/2007 | Zou et al. |
| 2007/0228588 A1 | 10/2007 | Noritomi et al. |
| 2007/0231823 A1 | 10/2007 | McKernan et al. |

(56) References Cited

U.S. PATENT DOCUMENTS

| | | |
|---|---|---|
| 2007/0238113 A1 | 10/2007 | Kanda et al. |
| 2007/0259357 A1 | 11/2007 | Brenner |
| 2007/0264320 A1 | 11/2007 | Lee et al. |
| 2008/0003142 A1 | 1/2008 | Link et al. |
| 2008/0004436 A1 | 1/2008 | Tawfik et al. |
| 2008/0014589 A1 | 1/2008 | Link et al. |
| 2008/0124726 A1 | 5/2008 | Monforte |
| 2008/0138878 A1 | 6/2008 | Kubu et al. |
| 2008/0213766 A1 | 9/2008 | Brown et al. |
| 2008/0228268 A1 | 9/2008 | Shannon et al. |
| 2008/0241820 A1 | 10/2008 | Krutzik et al. |
| 2008/0242560 A1 | 10/2008 | Gunderson et al. |
| 2008/0268450 A1 | 10/2008 | Nam et al. |
| 2008/0268507 A1 | 10/2008 | Xu et al. |
| 2009/0005252 A1 | 1/2009 | Drmanac et al. |
| 2009/0011943 A1 | 1/2009 | Drmanac et al. |
| 2009/0012187 A1 | 1/2009 | Chu et al. |
| 2009/0025277 A1 | 1/2009 | Takanashi |
| 2009/0035770 A1 | 2/2009 | Mathies et al. |
| 2009/0048124 A1 | 2/2009 | Leamon et al. |
| 2009/0053169 A1 | 2/2009 | Castillo et al. |
| 2009/0062129 A1 | 3/2009 | McKernan et al. |
| 2009/0068170 A1 | 3/2009 | Weitz et al. |
| 2009/0098555 A1 | 4/2009 | Roth et al. |
| 2009/0099041 A1 | 4/2009 | Church et al. |
| 2009/0105959 A1 | 4/2009 | Braverman et al. |
| 2009/0118488 A1 | 5/2009 | Drmanac et al. |
| 2009/0134027 A1 | 5/2009 | Jary |
| 2009/0137404 A1 | 5/2009 | Drmanac et al. |
| 2009/0137414 A1 | 5/2009 | Drmanac et al. |
| 2009/0143244 A1 | 6/2009 | Bridgham et al. |
| 2009/0148961 A1 | 6/2009 | Luchini et al. |
| 2009/0155780 A1 | 6/2009 | Xiao et al. |
| 2009/0155781 A1 | 6/2009 | Drmanac et al. |
| 2009/0197248 A1 | 8/2009 | Griffiths et al. |
| 2009/0197772 A1 | 8/2009 | Griffiths et al. |
| 2009/0202984 A1 | 8/2009 | Cantor |
| 2009/0203531 A1 | 8/2009 | Kurn |
| 2009/0264299 A1 | 10/2009 | Drmanac et al. |
| 2009/0286687 A1 | 11/2009 | Dressman et al. |
| 2009/0325260 A1 | 12/2009 | Otto et al. |
| 2010/0021973 A1 | 1/2010 | Makarov et al. |
| 2010/0021984 A1 | 1/2010 | Edd et al. |
| 2010/0022414 A1 | 1/2010 | Link et al. |
| 2010/0035254 A1 | 2/2010 | Williams |
| 2010/0062494 A1 | 3/2010 | Church et al. |
| 2010/0069263 A1 | 3/2010 | Shendure et al. |
| 2010/0086914 A1 | 4/2010 | Bentley et al. |
| 2010/0105112 A1 | 4/2010 | Holtze et al. |
| 2010/0113296 A1 | 5/2010 | Myerson |
| 2010/0120098 A1 | 5/2010 | Grunenwald et al. |
| 2010/0130369 A1 | 5/2010 | Shenderov et al. |
| 2010/0136544 A1 | 6/2010 | Agresti et al. |
| 2010/0137163 A1 | 6/2010 | Link et al. |
| 2010/0173394 A1 | 7/2010 | Colston, Jr. et al. |
| 2010/0187705 A1 | 7/2010 | Lee et al. |
| 2010/0210479 A1 | 8/2010 | Griffiths et al. |
| 2010/0216153 A1 | 8/2010 | Lapidus et al. |
| 2010/0248237 A1 | 9/2010 | Froehlich et al. |
| 2010/0248991 A1 | 9/2010 | Roesler et al. |
| 2010/0304982 A1 | 12/2010 | Hinz et al. |
| 2011/0000560 A1 | 1/2011 | Miller et al. |
| 2011/0008775 A1 | 1/2011 | Gao et al. |
| 2011/0028412 A1 | 2/2011 | Cappello et al. |
| 2011/0033548 A1 | 2/2011 | Lai et al. |
| 2011/0033854 A1 | 2/2011 | Drmanac et al. |
| 2011/0053798 A1 | 3/2011 | Hindson et al. |
| 2011/0059556 A1 | 3/2011 | Strey et al. |
| 2011/0071053 A1 | 3/2011 | Drmanac et al. |
| 2011/0086780 A1 | 4/2011 | Colston, Jr. et al. |
| 2011/0092376 A1 | 4/2011 | Colston, Jr. et al. |
| 2011/0092392 A1 | 4/2011 | Colston, Jr. et al. |
| 2011/0160078 A1 | 6/2011 | Fodor et al. |
| 2011/0166034 A1 | 7/2011 | Kwong et al. |
| 2011/0195496 A1 | 8/2011 | Muraguchi et al. |
| 2011/0201526 A1 | 8/2011 | Berka et al. |
| 2011/0212090 A1 | 9/2011 | Pedersen et al. |
| 2011/0217736 A1 | 9/2011 | Hindson |
| 2011/0218123 A1 | 9/2011 | Weitz et al. |
| 2011/0263457 A1 | 10/2011 | Krutzik et al. |
| 2011/0267457 A1 | 11/2011 | Weitz et al. |
| 2011/0281736 A1 | 11/2011 | Drmanac et al. |
| 2011/0281738 A1 | 11/2011 | Drmanac et al. |
| 2011/0287435 A1 | 11/2011 | Grunenwald et al. |
| 2011/0305761 A1 | 12/2011 | Shum et al. |
| 2011/0306141 A1 | 12/2011 | Bronchetti et al. |
| 2011/0319281 A1 | 12/2011 | Drmanac |
| 2012/0000777 A1 | 1/2012 | Garrell et al. |
| 2012/0003657 A1 | 1/2012 | Myllykangas et al. |
| 2012/0010091 A1 | 1/2012 | Linnarson |
| 2012/0010098 A1 | 1/2012 | Griffiths et al. |
| 2012/0010107 A1 | 1/2012 | Griffiths et al. |
| 2012/0014977 A1 | 1/2012 | Furihata et al. |
| 2012/0015382 A1 | 1/2012 | Weitz et al. |
| 2012/0015822 A1 | 1/2012 | Weitz et al. |
| 2012/0071331 A1 | 3/2012 | Casbon et al. |
| 2012/0121481 A1 | 5/2012 | Romanowsky et al. |
| 2012/0132288 A1 | 5/2012 | Weitz et al. |
| 2012/0135893 A1 | 5/2012 | Drmanac et al. |
| 2012/0165219 A1 | 6/2012 | Van Der Zaag et al. |
| 2012/0172259 A1 | 7/2012 | Rigatti et al. |
| 2012/0184449 A1 | 7/2012 | Hixson et al. |
| 2012/0190032 A1 | 7/2012 | Ness et al. |
| 2012/0190037 A1 | 7/2012 | Durin et al. |
| 2012/0196288 A1 | 8/2012 | Beer |
| 2012/0208705 A1 | 8/2012 | Steemers et al. |
| 2012/0208724 A1 | 8/2012 | Steemers et al. |
| 2012/0211084 A1 | 8/2012 | Weitz et al. |
| 2012/0220494 A1 | 8/2012 | Samuels et al. |
| 2012/0220497 A1 | 8/2012 | Jacobson et al. |
| 2012/0222748 A1 | 9/2012 | Weitz et al. |
| 2012/0231972 A1 | 9/2012 | Golyshin et al. |
| 2012/0252012 A1 | 10/2012 | Armougom et al. |
| 2012/0253689 A1 | 10/2012 | Rogan |
| 2012/0289428 A1 | 11/2012 | Duffy et al. |
| 2012/0297493 A1 | 11/2012 | Cooper et al. |
| 2012/0309002 A1 | 12/2012 | Link |
| 2012/0316074 A1 | 12/2012 | Saxonov |
| 2013/0017978 A1 | 1/2013 | Kavanagh et al. |
| 2013/0018970 A1 | 1/2013 | Woundy et al. |
| 2013/0022682 A1 | 1/2013 | Lee et al. |
| 2013/0028812 A1 | 1/2013 | Prieto et al. |
| 2013/0041004 A1 | 2/2013 | Drager et al. |
| 2013/0046030 A1 | 2/2013 | Rotem et al. |
| 2013/0059310 A1 | 3/2013 | Brenner et al. |
| 2013/0078638 A1 | 3/2013 | Berka et al. |
| 2013/0079231 A1 | 3/2013 | Pushkarev et al. |
| 2013/0079251 A1 | 3/2013 | Boles |
| 2013/0084243 A1 | 4/2013 | Goetsch et al. |
| 2013/0096073 A1 | 4/2013 | Sidelman |
| 2013/0109575 A1 | 5/2013 | Kleinschmidt et al. |
| 2013/0109576 A1 | 5/2013 | Shuber et al. |
| 2013/0109596 A1 | 5/2013 | Peterson et al. |
| 2013/0121893 A1 | 5/2013 | Delamarche et al. |
| 2013/0130919 A1 | 5/2013 | Chen et al. |
| 2013/0157870 A1 | 6/2013 | Pushkarev et al. |
| 2013/0157899 A1 | 6/2013 | Adler, Jr. et al. |
| 2013/0178368 A1 | 7/2013 | Griffiths et al. |
| 2013/0189700 A1 | 7/2013 | So et al. |
| 2013/0203605 A1 | 8/2013 | Shendure et al. |
| 2013/0203675 A1 | 8/2013 | DeSimone et al. |
| 2013/0210639 A1 | 8/2013 | Link et al. |
| 2013/0210991 A1 | 8/2013 | Fonnum et al. |
| 2013/0211055 A1 | 8/2013 | Raines et al. |
| 2013/0225418 A1 | 8/2013 | Watson |
| 2013/0225623 A1 | 8/2013 | Buxbaum et al. |
| 2013/0273640 A1 | 10/2013 | Krishnan et al. |
| 2013/0274117 A1 | 10/2013 | Church et al. |
| 2013/0296173 A1 | 11/2013 | Callow et al. |
| 2013/0343317 A1 | 12/2013 | Etemad et al. |
| 2013/0344508 A1 | 12/2013 | Schwartz et al. |
| 2014/0030350 A1 | 1/2014 | Ashrafi et al. |
| 2014/0037514 A1 | 2/2014 | Stone et al. |
| 2014/0038178 A1 | 2/2014 | Otto et al. |

(56) References Cited

U.S. PATENT DOCUMENTS

| | | |
|---|---|---|
| 2014/0057799 A1 | 2/2014 | Johnson et al. |
| 2014/0065234 A1 | 3/2014 | Shum et al. |
| 2014/0080717 A1 | 3/2014 | Li et al. |
| 2014/0093916 A1 | 4/2014 | Belyaev |
| 2014/0120529 A1 | 5/2014 | Andersen et al. |
| 2014/0155274 A1 | 6/2014 | Xie et al. |
| 2014/0155295 A1 | 6/2014 | Hindson et al. |
| 2014/0194323 A1 | 7/2014 | Gillevet |
| 2014/0199730 A1 | 7/2014 | Agresti et al. |
| 2014/0199731 A1 | 7/2014 | Agresti et al. |
| 2014/0206554 A1 | 7/2014 | Hindson et al. |
| 2014/0227684 A1 | 8/2014 | Hindson et al. |
| 2014/0227706 A1 | 8/2014 | Kato et al. |
| 2014/0228255 A1 | 8/2014 | Hindson et al. |
| 2014/0235506 A1 | 8/2014 | Hindson et al. |
| 2014/0242664 A1 | 8/2014 | Zhang et al. |
| 2014/0274740 A1 | 9/2014 | Srinivasan et al. |
| 2014/0287963 A1 | 9/2014 | Hindson et al. |
| 2014/0302503 A1 | 10/2014 | Lowe et al. |
| 2014/0315725 A1 | 10/2014 | Faham et al. |
| 2014/0315755 A1 | 10/2014 | Chen et al. |
| 2014/0357500 A1 | 12/2014 | Vigneault et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005188 A1 | 1/2015 | Levner et al. |
| 2015/0005199 A1 | 1/2015 | Hindson et al. |
| 2015/0005200 A1 | 1/2015 | Hindson et al. |
| 2015/0011430 A1 | 1/2015 | Saxonov |
| 2015/0011432 A1 | 1/2015 | Saxonov |
| 2015/0031037 A1 | 1/2015 | Li et al. |
| 2015/0057163 A1 | 2/2015 | Rotem et al. |
| 2015/0072899 A1 | 3/2015 | Ward et al. |
| 2015/0111256 A1 | 4/2015 | Church et al. |
| 2015/0111788 A1 | 4/2015 | Fernandez et al. |
| 2015/0119280 A1 | 4/2015 | Srinivas et al. |
| 2015/0211056 A1 | 7/2015 | Um et al. |
| 2015/0218633 A1 | 8/2015 | Hindson et al. |
| 2015/0224466 A1 | 8/2015 | Hindson et al. |
| 2015/0225777 A1 | 8/2015 | Hindson et al. |
| 2015/0225778 A1 | 8/2015 | Hindson et al. |
| 2015/0225786 A1 | 8/2015 | Litterst et al. |
| 2015/0247182 A1 | 9/2015 | Faham et al. |
| 2015/0259736 A1 | 9/2015 | Steemers et al. |
| 2015/0267191 A1 | 9/2015 | Steelman et al. |
| 2015/0291942 A1 | 10/2015 | Gloeckner et al. |
| 2015/0292988 A1 | 10/2015 | Bharadwaj et al. |
| 2015/0298091 A1 | 10/2015 | Weitz et al. |
| 2015/0299772 A1 | 10/2015 | Zhang |
| 2015/0299784 A1 | 10/2015 | Fan et al. |
| 2015/0329617 A1 | 11/2015 | Winther et al. |
| 2015/0329852 A1 | 11/2015 | Nolan |
| 2015/0329891 A1 | 11/2015 | Tan et al. |
| 2015/0337298 A1 | 11/2015 | Xi et al. |
| 2015/0353999 A1 | 12/2015 | Agresti et al. |
| 2015/0361418 A1 | 12/2015 | Reed |
| 2015/0368638 A1 | 12/2015 | Steemers et al. |
| 2015/0368694 A1 | 12/2015 | Pan et al. |
| 2015/0376605 A1 | 12/2015 | Jarosz et al. |
| 2015/0376608 A1 | 12/2015 | Kaper et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0024558 A1 | 1/2016 | Hardenbol et al. |
| 2016/0025726 A1 | 1/2016 | Altin et al. |
| 2016/0032282 A1 | 2/2016 | Vigneault et al. |
| 2016/0053253 A1 | 2/2016 | Salathia et al. |
| 2016/0060621 A1 | 3/2016 | Agresti et al. |
| 2016/0060691 A1 | 3/2016 | Giresi et al. |
| 2016/0115474 A1 | 4/2016 | Jelinek et al. |
| 2016/0122753 A1 | 5/2016 | Mikkelsen et al. |
| 2016/0122817 A1 | 5/2016 | Jarosz et al. |
| 2016/0145683 A1 | 5/2016 | Fan et al. |
| 2016/0153005 A1 | 6/2016 | Zhang et al. |
| 2016/0160235 A1 | 6/2016 | Solodushko et al. |
| 2016/0177359 A1 | 6/2016 | Ukanis et al. |
| 2016/0201125 A1 | 7/2016 | Samuels et al. |
| 2016/0208323 A1 | 7/2016 | Bernstein et al. |
| 2016/0231324 A1 | 8/2016 | Zhao et al. |
| 2016/0244742 A1 | 8/2016 | Linnarsson et al. |
| 2016/0244811 A1 | 8/2016 | Edwards |
| 2016/0244825 A1 | 8/2016 | Vigneault et al. |
| 2016/0251697 A1 | 9/2016 | Nolan |
| 2016/0257984 A1 | 9/2016 | Hardenbol et al. |
| 2016/0281160 A1 | 9/2016 | Jarosz et al. |
| 2016/0289769 A1 | 10/2016 | Schwartz et al. |
| 2016/0298107 A1 | 10/2016 | O'Farrell et al. |
| 2016/0304860 A1 | 10/2016 | Hindson et al. |
| 2016/0326583 A1 | 11/2016 | Johnson et al. |
| 2016/0348093 A1 | 12/2016 | Price et al. |
| 2016/0376663 A1 | 12/2016 | Brown |
| 2017/0009274 A1 | 1/2017 | Abate et al. |
| 2017/0016041 A1 | 1/2017 | Greenfield et al. |
| 2017/0114390 A1 | 4/2017 | Hindson et al. |
| 2017/0145476 A1 | 5/2017 | Ryvkin et al. |
| 2017/0183701 A1 | 6/2017 | Agresti et al. |
| 2017/0211127 A1 | 7/2017 | Mikkelsen et al. |
| 2017/0260584 A1 | 9/2017 | Zheng et al. |
| 2017/0268056 A1 | 9/2017 | Vigneault et al. |
| 2017/0321252 A1 | 11/2017 | Hindson et al. |
| 2017/0343545 A1 | 11/2017 | Hadrup et al. |
| 2017/0348691 A1 | 12/2017 | Bharadwaj et al. |
| 2017/0356027 A1 | 12/2017 | Hindson et al. |
| 2018/0015473 A1 | 1/2018 | Bharadwaj et al. |
| 2018/0030515 A1 | 2/2018 | Regev et al. |
| 2018/0057868 A1 | 3/2018 | Walder et al. |
| 2018/0080021 A1 | 3/2018 | Reuter et al. |
| 2018/0087050 A1 | 3/2018 | Zheng et al. |
| 2018/0088112 A1 | 3/2018 | Fan et al. |
| 2018/0112253 A1 | 4/2018 | Hindson et al. |
| 2018/0179580 A1 | 6/2018 | Hindson et al. |
| 2018/0179591 A1 | 6/2018 | Belgrader et al. |
| 2018/0180601 A1 | 6/2018 | Pedersen et al. |
| 2018/0195060 A1 | 7/2018 | Wang et al. |
| 2018/0195112 A1 | 7/2018 | Lebofsky et al. |
| 2018/0216162 A1 | 8/2018 | Belhocine et al. |
| 2018/0237951 A1 | 8/2018 | Bock et al. |
| 2018/0258466 A1 | 9/2018 | Hindson et al. |
| 2018/0258482 A1 | 9/2018 | Hindson et al. |
| 2018/0265928 A1 | 9/2018 | Schnall-Levin et al. |
| 2018/0267036 A1 | 9/2018 | Fan et al. |
| 2018/0273933 A1 | 9/2018 | Gunderson et al. |
| 2018/0274027 A1 | 9/2018 | Hindson et al. |
| 2018/0282804 A1 | 10/2018 | Hindson et al. |
| 2018/0305685 A1 | 10/2018 | Li et al. |
| 2018/0327839 A1 | 11/2018 | Hindson et al. |
| 2018/0335424 A1 | 11/2018 | Chen et al. |
| 2018/0340169 A1 | 11/2018 | Belhocine et al. |
| 2018/0340170 A1 | 11/2018 | Belhocine et al. |
| 2018/0340171 A1 | 11/2018 | Belhocine et al. |
| 2018/0340172 A1 | 11/2018 | Belhocine et al. |
| 2018/0340939 A1 | 11/2018 | Gaublomme et al. |
| 2018/0346979 A1 | 12/2018 | Hindson et al. |
| 2018/0363029 A1 | 12/2018 | Hindson et al. |
| 2018/0371538 A1 | 12/2018 | Blauwkamp et al. |
| 2018/0371540 A1 | 12/2018 | Hindson et al. |
| 2018/0376609 A1 | 12/2018 | Ju et al. |
| 2019/0002967 A1 | 1/2019 | Chen et al. |
| 2019/0024166 A1 | 1/2019 | Hindson et al. |
| 2019/0032129 A1 | 1/2019 | Hindson et al. |
| 2019/0032130 A1 | 1/2019 | Giresi et al. |
| 2019/0040382 A1 | 2/2019 | Steemers et al. |
| 2019/0040464 A1 | 2/2019 | Giresi et al. |
| 2019/0071656 A1 | 3/2019 | Chang et al. |
| 2019/0078150 A1 | 3/2019 | Chen et al. |
| 2019/0085391 A1 | 3/2019 | Hindson et al. |
| 2019/0127731 A1 | 5/2019 | McDermott |
| 2019/0136316 A1 | 5/2019 | Hindson et al. |
| 2019/0136317 A1 | 5/2019 | Hindson et al. |
| 2019/0136319 A1 | 5/2019 | Hindson et al. |

(56) References Cited

U.S. PATENT DOCUMENTS

| | | | |
|---|---|---|---|
| 2019/0153436 A1 | 5/2019 | Belhocine et al. | |
| 2019/0153532 A1 | 5/2019 | Bharadwaj et al. | |

FOREIGN PATENT DOCUMENTS

| | | | |
|---|---|---|---|
| EP | 1594980 B1 | 11/2009 | |
| EP | 1967592 B1 | 4/2010 | |
| EP | 2258846 A2 | 12/2010 | |
| EP | 2145955 B1 | 2/2012 | |
| EP | 1905828 B1 | 8/2012 | |
| EP | 2136786 B1 | 10/2012 | |
| EP | 1908832 B1 | 12/2012 | |
| EP | 2540389 A1 | 1/2013 | |
| EP | 2635679 A1 | 9/2013 | |
| EP | 2752664 A1 | 7/2014 | |
| GB | 2097692 B | 5/1985 | |
| GB | 2485850 A | 5/2012 | |
| JP | S5949832 A | 3/1984 | |
| JP | S60227826 A | 11/1985 | |
| JP | 2006-507921 A | 3/2006 | |
| JP | 2006-289250 A | 10/2006 | |
| JP | 2007-015990 A | 1/2007 | |
| JP | 2007-268350 A | 10/2007 | |
| JP | 2009-513948 A | 4/2009 | |
| JP | 2009-208074 A | 9/2009 | |
| JP | 2012-131798 A | 7/2012 | |
| JP | 2012522517 A | 9/2012 | |
| WO | WO-8402000 A1 | 5/1984 | |
| WO | WO-9301498 A1 | 1/1993 | |
| WO | WO-9418218 A1 | 8/1994 | |
| WO | WO-9419101 A1 | 9/1994 | |
| WO | WO-94/23699 A1 | 10/1994 | |
| WO | WO-95/30782 A1 | 11/1995 | |
| WO | WO-96/29629 A2 | 9/1996 | |
| WO | WO-96/41011 A1 | 12/1996 | |
| WO | WO-98/02237 A1 | 1/1998 | |
| WO | WO-9852691 A1 | 11/1998 | |
| WO | WO-99/09217 A1 | 2/1999 | |
| WO | WO-9942597 A1 | 8/1999 | |
| WO | WO-99/52708 A1 | 10/1999 | |
| WO | WO-2000/008212 A1 | 2/2000 | |
| WO | WO-0023181 A1 | 4/2000 | |
| WO | WO-00/26412 A1 | 5/2000 | |
| WO | WO-0034527 A2 | 6/2000 | |
| WO | WO-00/43766 A1 | 7/2000 | |
| WO | WO-00/70095 A2 | 11/2000 | |
| WO | WO-01/02850 A1 | 1/2001 | |
| WO | WO-01/14589 A2 | 3/2001 | |
| WO | WO-01/89787 A2 | 11/2001 | |
| WO | WO-01/90418 A1 | 11/2001 | |
| WO | WO-01/27610 A3 | 3/2002 | |
| WO | WO-02/31203 A2 | 4/2002 | |
| WO | WO-02/086148 A1 | 10/2002 | |
| WO | WO-02/18949 A3 | 1/2003 | |
| WO | WO-03/062462 A2 | 7/2003 | |
| WO | WO-2004/002627 A2 | 1/2004 | |
| WO | WO-2004/010106 A2 | 1/2004 | |
| WO | WO-2004/061083 A2 | 7/2004 | |
| WO | WO-2004/065617 A2 | 8/2004 | |
| WO | WO-2004/069849 A2 | 8/2004 | |
| WO | WO-2004/091763 A2 | 10/2004 | |
| WO | WO-2004/102204 A1 | 11/2004 | |
| WO | WO-2004/103565 A2 | 12/2004 | |
| WO | WO-2004/105734 A1 | 12/2004 | |
| WO | WO-2005/002730 A1 | 1/2005 | |
| WO | WO-2005/021151 A1 | 3/2005 | |
| WO | WO-2005/023331 A2 | 3/2005 | |
| WO | WO-2005/040406 A1 | 5/2005 | |
| WO | WO-2005/049787 A9 | 6/2005 | |
| WO | WO-2005/082098 A2 | 9/2005 | |
| WO | WO-2006/030993 A1 | 3/2006 | |
| WO | WO-2006/078841 A1 | 7/2006 | |
| WO | WO-2006071770 A2 | 7/2006 | |
| WO | WO-2006086210 A2 | 8/2006 | |
| WO | WO-2006/096571 A2 | 9/2006 | |
| WO | WO-2007/001448 A2 | 1/2007 | |
| WO | WO-2007/002490 A2 | 1/2007 | |
| WO | WO-2007/012638 A1 | 2/2007 | |
| WO | WO-2007/018601 A1 | 2/2007 | |
| WO | WO-2007/024840 A2 | 3/2007 | |
| WO | WO-2007/081387 A1 | 7/2007 | |
| WO | WO-2007/084192 A2 | 7/2007 | |
| WO | WO-2007/089541 A2 | 8/2007 | |
| WO | WO-2007/093819 A2 | 8/2007 | |
| WO | WO-2007/111937 A1 | 10/2007 | |
| WO | WO-2007/114794 A1 | 10/2007 | |
| WO | WO-2007/121489 A2 | 10/2007 | |
| WO | WO-2007/133710 A2 | 11/2007 | |
| WO | WO-2007/138178 A2 | 12/2007 | |
| WO | WO-2007/139766 A2 | 12/2007 | |
| WO | WO-2007/140015 A2 | 12/2007 | |
| WO | WO-2007/147079 A2 | 12/2007 | |
| WO | WO-2007/149432 A2 | 12/2007 | |
| WO | WO-2008/021123 A1 | 2/2008 | |
| WO | WO-2008/091792 A2 | 7/2008 | |
| WO | WO-2008/102057 A1 | 8/2008 | |
| WO | WO-2008/121342 A2 | 10/2008 | |
| WO | WO-2007/081385 A8 | 11/2008 | |
| WO | WO-2008/061193 A3 | 11/2008 | |
| WO | WO-2008/109176 A8 | 11/2008 | |
| WO | WO-2008/134153 A1 | 11/2008 | |
| WO | WO-2008135512 A2 | 11/2008 | |
| WO | WO-2008/150432 A1 | 12/2008 | |
| WO | WO-2009/005680 A1 | 1/2009 | |
| WO | WO-2009/011808 A1 | 1/2009 | |
| WO | WO-2009/015296 A1 | 1/2009 | |
| WO | WO-2009/048532 A2 | 4/2009 | |
| WO | WO-2009/061372 A1 | 5/2009 | |
| WO | WO-2009/085215 A1 | 7/2009 | |
| WO | WO-2009/147386 A1 | 12/2009 | |
| WO | WO-2010/004018 A2 | 1/2010 | |
| WO | WO-2010009735 A2 | 1/2010 | |
| WO | WO-2010/033200 A2 | 3/2010 | |
| WO | WO-2010/048605 A2 | 4/2010 | |
| WO | WO-2010/104604 A1 | 9/2010 | |
| WO | WO-2010/115154 A1 | 10/2010 | |
| WO | WO-2010/148039 A2 | 12/2010 | |
| WO | WO-2010/151776 A2 | 12/2010 | |
| WO | WO-2010/117620 A3 | 2/2011 | |
| WO | WO-2011028539 A1 | 3/2011 | |
| WO | WO-2011/047870 A1 | 4/2011 | |
| WO | WO-2011/056546 A1 | 5/2011 | |
| WO | WO-2011/074960 A1 | 6/2011 | |
| WO | WO-2011106314 A2 | 9/2011 | |
| WO | WO-2011/140627 A1 | 11/2011 | |
| WO | WO-2011156529 A2 | 12/2011 | |
| WO | WO-2012/012037 A1 | 1/2012 | |
| WO | WO-2012/019765 A1 | 2/2012 | |
| WO | WO-2011140510 A3 | 3/2012 | |
| WO | WO-2012/047889 A2 | 4/2012 | |
| WO | WO-2012/048340 A2 | 4/2012 | |
| WO | WO-2012/048341 A1 | 4/2012 | |
| WO | WO-2012/061832 A1 | 5/2012 | |
| WO | WO-2012087736 A1 | 6/2012 | |
| WO | WO-2011/066476 A8 | 8/2012 | |
| WO | WO-2012/106546 A2 | 8/2012 | |
| WO | WO-2012/112804 A1 | 8/2012 | |
| WO | WO-2012/112970 A2 | 8/2012 | |
| WO | WO-2012/083225 A4 | 9/2012 | |
| WO | WO-2012/136734 A1 | 10/2012 | |
| WO | WO-2012/142611 A2 | 10/2012 | |
| WO | WO-2012/148497 A2 | 11/2012 | |
| WO | WO-2012/149042 A2 | 11/2012 | |
| WO | WO-2012150317 A | 11/2012 | |
| WO | WO-2012/166425 A2 | 12/2012 | |
| WO | WO-2013/019751 A1 | 2/2013 | |
| WO | WO-2013/036929 A1 | 3/2013 | |
| WO | WO-2013/055955 A1 | 4/2013 | |
| WO | WO-2013/096643 A1 | 6/2013 | |
| WO | WO-2013/122996 A1 | 8/2013 | |
| WO | WO-2013/123125 A1 | 8/2013 | |
| WO | WO-2013/126741 A1 | 8/2013 | |
| WO | WO-2013/134261 A1 | 9/2013 | |
| WO | WO-2013/150083 A1 | 10/2013 | |

(56) References Cited

FOREIGN PATENT DOCUMENTS

| WO | WO-2013/177220 A1 | 11/2013 |
|---|---|---|
| WO | WO-2013/188872 A1 | 12/2013 |
| WO | WO-2014018460 A1 | 1/2014 |
| WO | WO-2014/028537 A1 | 2/2014 |
| WO | WO-2014/053854 A1 | 4/2014 |
| WO | WO-2014/071361 A1 | 5/2014 |
| WO | WO-2014/074611 A1 | 5/2014 |
| WO | WO-2014072703 A1 | 5/2014 |
| WO | WO-2014/093676 A1 | 6/2014 |
| WO | WO-2014/108810 A2 | 7/2014 |
| WO | WO-2014/140309 A1 | 9/2014 |
| WO | WO-2014/144495 A1 | 9/2014 |
| WO | WO-2014/150931 A1 | 9/2014 |
| WO | WO-2014145047 A1 | 9/2014 |
| WO | WO-2014/182835 A1 | 11/2014 |
| WO | WO-2014/189957 A2 | 11/2014 |
| WO | WO-2014/210353 A2 | 12/2014 |
| WO | WO-2014200767 A1 | 12/2014 |
| WO | WO-2015/031691 A1 | 3/2015 |
| WO | WO-2015/044428 A1 | 4/2015 |
| WO | WO-2015/164212 A1 | 10/2015 |
| WO | WO-2015/188839 A2 | 12/2015 |
| WO | WO-2015/200893 A2 | 12/2015 |
| WO | WO-2015185067 A1 | 12/2015 |
| WO | WO-2016/040476 A1 | 3/2016 |
| WO | WO-2016/061517 A2 | 4/2016 |
| WO | WO-2016033251 A3 | 4/2016 |
| WO | WO-2016100976 A2 | 6/2016 |
| WO | WO-2016/126871 A2 | 8/2016 |
| WO | WO-2016138496 A1 | 9/2016 |
| WO | WO-2016149661 A1 | 9/2016 |
| WO | WO-2016/168584 A1 | 10/2016 |
| WO | WO-2016/187256 A2 | 11/2016 |
| WO | WO-2016/187717 A1 | 12/2016 |
| WO | WO-2016/191618 A1 | 12/2016 |
| WO | WO-2016/207647 A1 | 12/2016 |
| WO | WO-2016/207653 A1 | 12/2016 |
| WO | WO-2016/207661 A1 | 12/2016 |
| WO | WO-2017/015075 A1 | 1/2017 |
| WO | WO-2017/025594 A1 | 2/2017 |
| WO | WO-2017/053905 A1 | 3/2017 |
| WO | WO-2017034970 A1 | 3/2017 |
| WO | WO-2017/075265 A1 | 5/2017 |
| WO | WO-2017075294 A1 | 5/2017 |
| WO | WO-2017/079593 A1 | 5/2017 |
| WO | WO-2017/096158 A1 | 6/2017 |
| WO | WO-2017/117358 A1 | 7/2017 |
| WO | WO-2017/151828 A1 | 9/2017 |
| WO | WO-2017/156336 A1 | 9/2017 |
| WO | WO-2017180420 A1 | 10/2017 |
| WO | WO-2018031631 A1 | 2/2018 |
| WO | WO-2018/045186 A1 | 3/2018 |
| WO | WO-2018039969 A1 | 3/2018 |
| WO | WO-2018058073 A2 | 3/2018 |
| WO | WO-2018/119301 A1 | 6/2018 |
| WO | WO-2018103025 A1 | 6/2018 |
| WO | WO-2018119447 A2 | 6/2018 |
| WO | WO-2018125982 A1 | 7/2018 |
| WO | WO-2018129368 A2 | 7/2018 |
| WO | WO-2018132635 A1 | 7/2018 |
| WO | WO-2018172726 A1 | 9/2018 |
| WO | WO-2018174827 A1 | 9/2018 |
| WO | WO-2018/191701 A1 | 10/2018 |
| WO | WO-2019/028166 A1 | 2/2019 |
| WO | WO-2019084328 A1 | 5/2019 |
| WO | WO-2019099751 A1 | 5/2019 |

OTHER PUBLICATIONS

"BD Rhapsody™ Single-Cell Analysis System: Analyze hundreds of genes across tens of thousands of single cells in parallel," BD, Becton, Dickinson and Company. BDGM1012 Rev. 1 (2017) (8 pages).

"Determining the elastic modulus of biological samples using atomic force microscopy," Broker JPK BIOAFM, <https://www.jpk.com/ app-technotes-img/AFM/pdf/jpk-app-elastic-modulus.14-1.pdf> (2009) (9 pages).

"Droplet Based Sequencing," slides dated Mar. 12, 2008.

"EZ-Tn5 Transposase," Epicenter. 1-5 (2012).

"EZ-Tn5TM Custom Transposome Construction Kits," Epicentre. 1-17 (2012).

"How many species of bacteria are there?" WiseGeek, retrieved Jan. 21, 2014.

"List of sequenced bacterial genomes" (Wikipedia.com; accessed Jan. 24, 2014).

"Oligo(dT)25 cellulose beads," NEB, <https://www.neb.com/~/media/Catalog/All-Products/286CA51268E24DE1B06F1CB288698B54/Datacards%20or%Manuals/S1408Datasheet-Lot0011205.pdf>, dated 2012.

"Oligotex Handbook," Qiagen XP055314680, <URL:http://www.qiagen.com/de/resources/download.apsx?id=f9fald98-d54d-47e7-a20b-8b0cb8975009&lang=en>, dated 2012.

"Portable Water Filters" (http://www.portablewaterfilters.org/water-filter-quide/particle-contaminant-size-chart-microns/) 2015, accessed Oct. 19, 2017.

"Protocols, M-270 Streptavidin," ThermoFisherScientific. (2007) (5 pages).

"U.S. Appl. No. 61/982,001, filed Apr. 21, 2014 (Year:2014)".

"Spormann Laboratory, Polymerase Chain Reaction (PCR)," Alfred Spormann Laboratory. 1-3 (2009).

"Streptavidin-agarose (S1638) product information sheet," Sigma, <www.sigma-aldrich.com>.

"TCEP=HCI," Thermo Scientific, XP055508461, <https://assets.thermofisher.com/TFS-Assets/LSG/manuals/MAN0011306_TCEP_HCI_UG.pdf>, dated Dec. 31, 2013.

"Three Ways to Get Intimate with Epigenetic Marks," Epigenie, <https://epigenie.com/three-ways-to-get-intimate-with-epigenetic-marks/>, dated Oct. 24, 2012.

"Viscosity-Basic concepts," EPFL, XP055314117, <http://lhtc.epfl.ch/webdav/site/lhtc/shared/import/migration/2 VISCOSITY.pdf>, dated 2004.

10X Genomics. "10x Genomics Chromium™ Single Cell 3' Solution Utilized for Perturb-seq Approach," Press Release, <https://www.10xgenomics.com/news/10x-genomics-chromium-single-cell-3-solution-utilized- perturb-seq-approach/>, dated_Dec. 19, 2016.

Abate et al., "Beating Poisson encapsulation statistics using close-packed ordering," Lab Chip. 9(18):2628-31 (2009).

Abate et al., "Valve-based flow focusing for drop formation," Appl Phys Lett. 94 (2009) (3 pages).

Abate, et al. High-throughput injection with microfluidics using picoinjectors. Proc Natl Acad Sci US A. Nov. 9, 2010;107(45):19163-6. doi: 10.1073/pNas.1006888107. Epub Oct. 20, 2010.

Adamson et al., "Production of arrays of chemically distinct nanolitre plugs via repeated splitting in microfluidic devices," Lab Chip. 6(9): 1178-1186 (2006).

Adamson, et al. A Multiplexed Single-Cell CRISPR Screening Platform Enables Systematic Dissection of the Unfolded Protein Response. Cell. Dec. 15, 2016;167(7):1867-1882.e21. doi:10.1016/j.cell.2016.11.048.

Adey et al. "Rapid, low-input, low-bias construction of shotgun fragment libraries by high-density in vitro transposition," Genome Biology. 11:R119 (2010).

Adey et al., "Ultra-low-input, tagmentation-based whole-genome bisulfite sequencing," Genome Research. 22(6): 1139-1143 (2012).

Agasti et al. "Photocleavable DNA barcode-antibody conjugates allow sensitive and multiplexed protein analysis in single cells," J Amer Chem Soc. 134(45): 18499-18502 (2012).

Agresti, et al. Selection of ribozymes that catalyse multiple-turnover Diels-Alder cycloadditions by using in vitro compartmentalization. Proc Natl Acad Sci US A. Nov. 8, 2005;102(45):16170-5. Epub Oct. 31, 2005.

AH006633.3 (*Homo sapiens* clone P1 and PAC max interactor 1 (MXI1) gene, complete cds, NCBI Reference Sequence, priority to Jun. 10, 2016, 5 pages) (Year:2016).

Ahern, "Biochemical, Reagents Kits Offer Scientists Good Return on Investment," The Scientist.9(15):1-7 (1995).

(56) References Cited

OTHER PUBLICATIONS

Ahern, The Scientist. 20: 20, 22 (1995).
Ailenberg et al., "Controlled Hot Start and Improved Specificity in Carrying Out PCR Utilizing Touch-Up and Loop Incorporated Primers (TULIPS)," BioTechniques. 29:1018-1024 (2000).
Aitman et al., "Copy number polymorphism in Fcgr3 predisposes to glomerulonephritis in rats and humans," Nature. 439(7078):851-5 (2006).
Akselband, "Enrichment of slow-growing marine microorganisms from mixed cultures using gel microdrop (GMD) growth assay and fluorescence-activated cell sorting," J Exp Marine Biol. 329:196-205 (2006).
Akselband, "Rapid mycobacteria drug susceptibility testing using gel microdrop (GMD) growth assay and flow cytometry," J Microbiol Methods. 62: 181-197 (2005).
Altemose et al., "Genomic Characterization of Large Heterochromatic Gaps in the Human Genome Assembly," PLOS Computational PLoS Comput Biol. 10(5) (2014) (14 pages).
Amini et al. "Haplotype-resolved whole-genome sequencing by contiguity-preserving transposition and combinatorial indexing" Nat Genet. 46(12):1343-1349 (2014).
Anna et al., "Formation of dispersions using 'flow focusing' in microchannels," Appln Phys Letts. 82(3): 364 (2003).
Anonymous: "Dynal MPC(TM)-S", Oct. 13, 2008 (Oct. 13, 2008), XP055603532, Retrieved from the Internet on Jul. 9, 2019; URL:<https://www.veritastk.co.jp/products/pdf/120%2020D.Dynal_MPC-S%28rev005%29.pdf>.
Ason et al. "DNA sequence bias during Tn5 transposition. Journal of molecular biology" J Mol Biol. 335(5):12-13-25 (2004).
Attia et al., "Micro-injection moulding of polymer microfluidic devices," Microfluidics and Nanofluidics. 7(1):1-28 (2009).
Balikova et al. "Autosomal-dominant microtia linked to five tandem copies of a copy-number-variable region at chromosome 4p16," Am J Hum Genet. 82(1):181-7 (2008).
Banchelli et al., "Phospholipid membranes decorated by cholesterol-based oligonucleotides as soft hybrid nanostructures," J Phys Chem B. 112(35): 10942-52 (2008).
Baret et al., "Fluorescence-activated droplet sorting (FADS): efficient microfluidic cell sorting based on enzymatic activity," Lab Chip. 9(13):1850-8 (2009).
Garstecki, P. et al. "Formation of monodisperse bubbles in a microfluidic flow-focusing device" Appl. Phys. Lett (2004) 85(13):2659-2651. DOI: 10.1063/1.1796526.
Bentley et al., "Supplementary Information," Nature. 456(7218): 53-9 (2008) (55 pages).
Bentolila et al., "Single-step multicolor fluorescence in situ hybridization using semiconductor quantum dot-DNA conjugates," Cell Biochem Biophys. 45(1): 59-70 (2006).
Bentzen et al., "Large-scale detection of antigen-specific T cells using peptide-MHC-I multimers labeled with DNA barcodes," Nat Biotechnol. 34(10):1037-1045 (2016).
Berkum et al. "Hi-C: a method to study the three-dimensional architecture of genomes," J Vis Exp. (39):1869 (2010).
Biles et al., "Low-fidelity Pyrococcus furiosis DNA polymerase mutants useful in error-prone PCR," Nucleic Acids Res. 32(22):e176 (2004).
Bjornsson et al., "Intra-individual change over time in DNA methylation with familial clustering," JAMA. 299(24):2877-83 (2008).
Bodi et al., "Comparison of Commercially Available Target Enrichment Methods for Next-Generation Sequencing," J Biomol Tech. 24(2): 73-86 (2013).
Boone et al., "Plastic advances microfluidic devices. The devices debuted in silicon and glass, but plastic fabrication may make them hugely successful in biotechnology application," Analytical Chemistry. 78A-86A (2002).
Boulanger et al., "Massively parallel haplotyping on microscopic beads for the high- throughput phase analysis of single molecules," PLoS One.7(4):1-10 (2012).

Boyle et al., "High-resolution genome-wide in vivo footprinting of diverse transcription factors in human cells," Genome Res. 21 (3):456-64 (2011).
Braeckmans et al., "Scanning the Code," Modern Drug Discovery. 28-32 (2003).
Bransky et al., "A microfluidic droplet generator based on a piezoelectric actuator," Lab Chip. 9(4):516-20 (2009).
Brenner et al., "In vitro cloning of complex mixtures of DNA on microbeads: physical separation of differentially expressed cDNAs," Proc Natl Acad Sci USA. 97(4):1665-70 (2000).
Briggs et al., "Tumor-infiltrating immune repertoires captures by single-cell barcoding in emulsion," with Supplementary material, bioRxiv. 134841 (2017).
Brouzes et al., "Droplet microfluidic technology for single-cell high-throughput screening," Proc Natl Acad Sci U S A. 106(34):14195-200 (2009).
Brown, "Targeted Sequencing Using Droplet-Based Microfluidics," RainDance Technologies. 1-18 (2009).
Browning et al., "Haplotype phasing: existing methods and new developments," Nat Rev Genet. 12(10):703-14 (2011).
Buchman et al., "Selective RNA amplification: a novel method using dUMP-containing primers and uracil DNA glycosylase," PCR Methods Appl. 3(1):28-31 (1993).
Buenrostro et al., "ATAC-seq: A Method for Assaying Chromatin Accessibility Genome- Wide," Curr Protoc Mol Biol. 109: 21.29.1-21.29.9. (2015).
Buenrostro et al., "Single-cell chromatin accessibility reveals principles of regulatory variation," Nature. 523(7561):486-90 (2015).
Buenrostro et al., "Transposition of native chromatin for fast and sensitive epigenomic profiling of open chromatin, DNA-binding proteins and nucleosome position," Nat Methods. 10(12):1213-8 (2013).
Buenrostro, et al., "Tranposition of native chromatin for fast and sensitive epigenomic profiling of open chromatin, DNA-binding proteins and nucleosome position", Nature Methods, 2013, 10(12): 1213-1218.
Burns et al., "An Integrated Nanoliter DNA Analysis Device," Science. 282(5388):484-7 (1998).
Burns et al., "The intensification of rapid reactions in multiphase systems using slug flow in capillaries," Lab Chip. 1(1): 10-5 (2001).
Burns, et al. Microfabricated structures for integrated DNA analysis. Proc Natl Acad Sci U S A. May 28, 1996; 93(11): 5556-5561.
Bystrykh et al., "Generalized DNA barcode design based on Hamming codes," PLoS One. 7(5):e36852 (2012).
Cappuzzo et al., "Increased HER2 gene copy number is associated with response to gefitinib therapy in epidermal growth factor receptor-positive non-small-cell lung cancer patients," J Clin Oncol. 23(22):5007-18 (2005).
Carroll, "The selection of high-producing cell lines using flow cytometry and cell sorting," Exp Op Biol. Therp. 4(11): 1821-1829 (2004).
Caruccio et al. "Preparation of Next-Generation Sequencing Libraries Using Nextera Technology: Simultaneous DNA Fragmentation and Adaptor Tagging by In Vitro Transposition," Methods Mol Biol. 733:241-55 (2011).
Caruccio, et al., "Nextera Technology for NGS DNA Library Preparation: Simultaneous Fragmentation and Tagging by In Vitro Transposition," Nextera Technology. 16-3: 1-3 (2009).
Casbon et al., "Reflex: intramolecular barcoding of long-range PCR products for sequencing multiple pooled DNAs," Nucleic Acids Res. 41(10) 1-6 (2013).
Cejas et al., "Chromatin immunoprecipitation from fixed clinical tissues reveals tumor-specific enhancer profiles," Nature Med. 22(6):685-691 (2016).
Chang et al., "Droplet-based microfluidic platform platform for heterogeneous enzymatic assays," Lab Chip. 13: 1817-1822 (2013).
Chaudhary, "A rapid method of cloning functioNal variable-region antibody genese in *Escherichia coli* as single-chain imrnunotoxins," Proc Nat! Acad Sci USA. 87: 1066-1070 (1990).
Chechetkin et al., "Sequencing by hybridization with the generic 6-mer oligonucleotide microarray: an advanced scheme for data processing," J Biomol Struct Dyn. 8(1):83-101 (2000).

(56) References Cited

OTHER PUBLICATIONS

Chen et al., "Chemical transfection of cells in picoliter aqueous droplets in fluorocarbon oil," Anal Chem. 83(22): 8816-20 (2011).
Chinese Office Action and search report dated May 23, 2013 for Application No. CN 200880127116.4 (H0498.70311CN00).
Choi et al., "Identification of novel isoforms of the EML4-ALK transforming gene in non-small cell lung cancer," Cancer Res. 68(13):4971-6 (2008).
Chokkalingam et al., "Probing cellular heterogeneity in cytokine-secreting immune cells using droplet-based microfluidics," Lab Chip. 13(24):4740-4 (2013).
Chou, H-P. et al. "Disposable Microdevices for DNA Analysis and Cell Sorting" Proc. Solid-State Sensor and Actuator Workshop Hilton Head, SC Jun. 8-11, 1998, pp. 11-14.
Christian, et al. Targeting DNA double-strand breaks with TAL effector nucleases. Genetics. 2010;186:757-761.
Christiansen et al., "The Covalent Eukaryotic Topoisomerase I-DNA Intermediate Catalyzes pH-dependent Hydrolysis and Alcoholysis," J Biol Chem. 269(15):11367-11373 (1994).
Chu et al., "Controllable monodisperse multiple emulsions," Angew Chem Int Ed Engl. 46(47):8970-4 (2007).
Chung et al., "Structural and molecular interrogation of intact biological systems," Nature. 497(7449):332-7 (2013).
Clark et al., "Single-cell epigenomics: powerful new methods for understanding gene regulation and cell identity," Genome Biol. 17:72 (2016).
Clausell-Tormos et al., "Droplet-based microfluidic platforms for the encapsulation and screening of mammalian cells and multicellular organisms," Chem Biol. 15:427-437 (2008).
Co-pending U.S. Appl. No. 15/440,772, filed Feb. 23, 2017.
Co-pending U.S. Appl. No. 15/449,741, filed Mar. 3, 2017.
Co-pending U.S. Appl. No. 15/596,754, filed May 16, 2017.
Co-pending U.S. Appl. No. 15/717,847, filed Sep. 27, 2017.
Co-pending U.S. Appl. No. 15/825,740, filed Nov. 29, 2017.
Co-pending U.S. Appl. No. 15/831,726, filed Dec. 5, 2017.
Co-pending U.S. Appl. No. 15/831,847, filed Dec. 5, 2017.
Co-pending U.S. Appl. No. 15/832,183, filed Dec. 5, 2017.
Co-pending U.S. Appl. No. 15/832,547, filed Dec. 5, 2017.
Co-pending U.S. Appl. No. 15/842,550, filed Dec. 14, 2017.
Co-pending U.S. Appl. No. 15/842,687, filed Dec. 14, 2017.
Co-pending U.S. Appl. No. 15/842,713, filed Dec. 14, 2017.
Co-pending U.S. Appl. No. 15/847,659, filed Dec. 19, 2017.
Co-pending U.S. Appl. No. 15/847,752, filed Dec. 19, 2017.
Co-pending U.S. Appl. No. 15/848,714, filed Dec. 20, 2017.
Co-pending U.S. Appl. No. 15/850,241, filed Dec. 21, 2017.
Co-pending U.S. Appl. No. 15/872,499, filed Jan. 16, 2018.
Co-pending U.S. Appl. No. 15/875,899, filed Jan. 19, 2018.
Co-pending U.S. Appl. No. 15/887,711, filed Feb. 2, 2018.
Co-pending U.S. Appl. No. 15/887,947, filed Feb. 2, 2018.
Co-pending U.S. Appl. No. 15/933,299, filed Mar. 22, 2018.
Co-pending U.S. Appl. No. 15/975,468, filed May 9, 2018.
Co-pending U.S. Appl. No. 15/980,473, filed May 15, 2018.
Co-pending U.S. Appl. No. 15/985,388, filed May 21, 2018.
Co-pending U.S. Appl. No. 16/000,803, filed Jun. 5, 2018.
Co-pending U.S. Appl. No. 16/033,065, filed Jul. 11, 2018.
Co-pending U.S. Appl. No. 16/044,374, filed Jul. 24, 2018.
Co-pending U.S. Appl. No. 16/045,474, filed Jul. 25, 2018.
Co-pending U.S. Appl. No. 16/052,431, filed Aug. 1, 2018.
Co-pending U.S. Appl. No. 16/052,486, filed Aug. 1, 2018.
Co-pending U.S. Appl. No. 16/056,231, filed Aug. 6, 2018.
Co-pending U.S. Appl. No. 16/107,685, filed Aug. 21, 2018.
Co-pending U.S. Appl. No. 16/138,448, filed Sep. 21, 2018.
Co-pending U.S. Appl. No. 16/144,832, filed Sep. 27, 2018.
Co-pending U.S. Appl. No. 16/160,576, filed Oct. 15, 2018.
Co-pending U.S. Appl. No. 16/160,719, filed Oct. 15, 2018.
Co-pending U.S. Appl. No. 16/165,389, filed Oct. 19, 2018.
Co-pending U.S. Appl. No. 16/170,980, filed Oct. 25, 2018.
Co-pending U.S. Appl. No. 16/196,684, filed Nov. 20, 2018.
Co-pending U.S. Appl. No. 16/206,168, filed Nov. 30, 2018.
Co-pending U.S. Appl. No. 16/212,441, filed Dec. 6, 2018.
Co-pending U.S. Appl. No. 16/228,261, filed Dec. 20, 2018.
Co-pending U.S. Appl. No. 16/228,362, filed Dec. 20, 2018.
Co-pending U.S. Appl. No. 16/230,936, filed Dec. 21, 2018.
Co-pending U.S. Appl. No. 16/231,142, filed Dec. 21, 2018.
Co-pending U.S. Appl. No. 16/231,185, filed Dec. 21, 2018.
Co-pending U.S. Appl. No. 16/242,962, filed Jan. 8, 2019.
Co-pending U.S. Appl. No. 16/246,322, filed Jan. 11, 2019.
Co-pending U.S. Appl. No. 16/249,688, filed Jan. 16, 2019.
Co-pending U.S. Appl. No. 16/294,769, filed Mar. 6, 2019.
Co-pending U.S. Appl. No. 16/395,090, filed Apr. 25, 2019.
Co-pending U.S. Appl. No. 16/419,428, filed May 22, 2019.
Co-pending U.S. Appl. No. 16/419,461, filed May 22, 2019.
Co-pending U.S. Appl. No. 16/419,555, filed May 22, 2019.
Co-pending U.S. Appl. No. 16/419,630, filed May 22, 2019.
Co-pending U.S. Appl. No. 16/419,820, filed May 22, 2019.
Co-pending U.S. Appl. No. 16/435,362, filed Jun. 7, 2019.
Co-pending U.S. Appl. No. 16/435,417, filed Jun. 7, 2019.
Cong et al., "Multiplex genome engineering using CRISPR/Cas systems," Science. 339(6121):819-23 (2013).
Cook et al., "Copy-number variations associated with neuropsychiatric conditions," Nature. 455(7215):919-23 (2008).
Coufal et al., "L1 retrotransposition in human neural progenitor cells," Nature. 460(7259):1127-31 (2009).
Curcio, Mario, Thesis: "Improved Techniques for High-Throughput Molecular Diagnostics," Doctor in Philosophy of Chemistry, Royal Institute of Technology, 2002 (131 pages).
Cusanovich et al., "Multiplex single-cell profiling of chromatin accessibility by combinatorial cellular indexing," Science. (6237): 910-4 (2015).
Cusanovich et al., "Supplementary materials for Multiplex single-cell profiling of chromatin accessibility by combinatorial cellular indexing," Science. 348(6237):910-4 (2015).
Damean et al., "Simultaneous measurement of reactions in microdroplets filled by concentration gradients," Lab Chip. 9(12): 1707-13 (2009).
De Bruin et al., "UBS Investment Research. Q-Series®: DNA Sequencing," UBS Securities LLC (2007) (15 pages).
Definition of "corresponding", Merriam-Webster Online, downloaded from http://www.merriam-webster.com/dictionary/corresponding (Year: 2019).
Dekker et al., "Capturing chromosome conformation," Science. 295(5558):1306-11 (2002).
Delehanty et al., "Peptides for specific intracellular delivery and targeting of nanoparticles: implications for developing nanoparticle-mediated drug delivery," Ther Deliv. 1 (3): 411-33 (2010).
Demirci et al., "Single cell epitaxy by acoustic picolitre droplets," Lab Chip. 7(9): 1139-45 (2007).
DePristo et al., "A framework for variation discovery and genotyping using next-generation DNA sequencing data," Nature Genet. 43(5):491-8 (2011).
Dey et al., "Integrated genome and transcriptome sequencing of the same cell," available in PMC Dec. 18, 2017, published in final edited form as: Nature Biotechnology. 33(3): 285-289 (2015).
Dhingra et al., "A complete solution for high throughput single cell targeted multiomic DNA and RNA sequencing for cancer research," Poster. AACR 2019.
Dixit et al., "Perturb-Seq: Dissecting Molecular Circuits with Scalable Single-Cell RNA Profiling of Pooled Genetic Screens," Cell. 167(7):1853-1866.e17 (2016).
Doerr, "The smallest bioreactor," Nature Methods. 2(5): 326 (2005).
Doshi et al., "Red blood cell-mimicking synthetic biomaterial particles," Proc Natl Acad Sci U S A. 106(51):21495-21499 (2009).
Dowding et al., "Oil core/polymer shell microcapsules by internal phase separation from emulsion droplets. II: controlling the release profile of active molecules," Langmuir. 21(12): 5278-84 (2005).
Draper et al., "Compartmentalization of electrophoretically separated analytes in a multiphase microfluidic platform," Anal Chem. 84(13): 5801-8 (2012).
Dressier et al., "Droplet-based microfluidics enabling impact on drug discovery," J Biomol Screen. 19(4): 483-96 (2014).
Dressman et al., "Supplementary Information pp. 1-2 of article published," PNAS. 100(15): 8817-22 (2003).

(56) References Cited

OTHER PUBLICATIONS

Dressman et al., "Transforming single DNA molecules into fluorescent magnetic particles for detection and enumeration of genetic variations," Proc Natl Acad Sci U S A. 100(15):8817-22 (2003).
Drmanac et al., "Sequencing by hybridization (SBH): advantages, achievements, and opportunities," Adv Biochem Eng Biotechnol. 77: 75-101 (2002).
Eastburn et al., "Ultrahigh-throughput mammalian single-cell reverse-transcriptase polymerase chain reaction in microfluidic droplets," Anal Chem. 85(16): 8016-21 (2013).
Esser-Kahn et al., "Triggered release from polymer capsules," Macromolecules. 44: 5539-5553 (2011).
Fabi et al., "Correlation of efficacy between EGFR gene copy number and lapatinib/capecitabine therapy in HER2-positive metastatic breast cancer," J Clin Oncol, ASCO Meeting abstract, Jun. 14, 2010. 1059(28):15S (2010).
Fan et al., "Noninvasive diagnosis of fetal aneuploidy by shotgun sequencing DNA from maternal blood," Proc Natl Acad Sci U S A. 105(42): 16266-71 (2008).
Fan et al., "Whole-genome molecular haplotyping of single cells," Nat Biotechnol. 29(1):51-7 (2011).
Fang et al., "Fluoride-cleavable biotinylation phosphoramidite for 5'-end-labeling and affinity purification of synthetic oligonucleotides," Nucleic Acids Res. 31(2):708-15 (2003).
Fanielli et al., "Pathology tissue-chromatin immunoprecipitation, coupled with high-throughput sequencing, allows the epigenetic profiling of patient samples," PNAS. 107(50): 21535-21540 (2010).
Flisher et al., "A scalable, fully automated process for construction of sequence-ready human exome targeted capture libraries," Genome Biol. 12(1):R1 (2011).
Frampton et al., "Development and validation of a clinical cancer genomic profiling test based on massively parallel DNA sequencing" Nat Biotechnol. 31(11):1023-1031 (2013).
Fredrickson et al., "Macro-to-micro interfaces for microfluidic devices," Lab Chip. 4(6): 526-33 (2004).
Freiberg et al., "Polymer microspheres for controlled drug release," Int J Pharm. 282(1-2): 1-18 (2004).
Fu et al., "A microfabricated fluorescence-activated cell sorter," Nat Biotech. 17(11): 1109-1111 (1999).
Fu. A.Y et al. "A microfabricated fluorescence-activated cell sorter" Nature Biotech (Nov. 1999) 17:1109-1111.
Fulton et al., "Advanced multiplexed analysis with the FlowMetrix system," Clin Chem. 43(9): 1749-56(1997).
Gangadharan et al., "DNA transposon Hermes insert into DNA in nucleosome-free regions in vivo," Proc Natl Acad Sci U S A. 107(51):21966-72 (2010).
Gao et al., "Toehold of dsDNA Exchange Affects the Hydrogel Swelling Kinetic of a Polymer-dsDNA Hybrid Hydrogel," Royal Soc Chem. 7:1741-1746 (2010).
Gartner et al., "The Microfluidic Toolbox—examples for fluidic interfaces and standardization concepts," Proc SPIE 4982, Microfluidics, BioMEMS, and Medical Microsystems. (2003).
Gericke et al., "Functional cellulose beads: preparation, characterization, and applications," Chem Rev. 113(7) 4812-4836 (2013).
Ghadessy et al., "Directed evolution of polymerase function by compartmentalized self-replication," Proc Natl Acad Sci U S A. 98(8): 4552-7 (2001).
Gonzalez et al., "The influence of CCL3L1 gene-containing segmental duplications on HIV-1/AIDS susceptibility," Science. 307(5714):1434-40 (2005).
Granieri, Lucia, Thesis: "Droplet-based microfluidics and engineering of tissue plasminogen activator for biomedical applications," Doctor of Philosophy in Chemistry, L'Universite de Strasbourg, 2009 (131 pages).
Grasland-Mongrain et al., "Droplet coalescence in microfluidic devices," <http://www.eleves.ens.fr/home/grasland/rapports/stage4.pdf>, dated Jan.-Jul. 2003 (31 pages).
Green et al., "Insertion site preference of Mu, Tn5, and Tn7 transposons," Mob DNA 3(1):3 (2012).

Greenleaf, "Assaying the epigenome in limited numbers of cells," Methods. 72:51-6 (2015).
Guo et al., "Droplet microfluidics for high-throughput biological assays," Lab Chip. 12(12):2146-55 (2012).
Gyarmati et al., "Reversible disulphide formation in polymer networks: a versatile functional group from synthesis to applications," European Polymer Journal. 49:1268-1286 (2013).
Hamilton, "microRNA in erythrocytes," Biochem Soc Trans. 38 (Pt 1): 229-231.(2010).
Han et al., "Targeted Sequencing of Cancer-Related Genes in Colorectal Cancer Using Next-Generation Sequencing," PLOS One. 8(5):e64271 (2013).
Han et al.,"CRISPR-Cas9 delivery to hard-to-transfect cells via membrane deformation" Science Advances. 1(7): E1500454 (2015) (8 pages).
Haring et al., "Chromatin immunoprecipitation: optimization, quantitative analysis and data normalization.,"Plant Methods. 3:11 (2007).
Hashimshony, T et al. "CEL-Seq: Single-Cell RNa-Seq by Multiplexed Linear Amplification" Cell Rep. Sep. 27, 2012;2(3):666-73. doi: 10.1016/j.celrep.2012.08.003. Epub Aug. 30, 2012.
He et al., "Genotyping-by-sequencing (GBS), an ultimate marker-assisted selections (MAS) tool to accelerate plant breeding," Frontiers Plant Sci. 5:1-8 (2014).
He, "Selective Encapsulation of Single Cells and Subcellular Organelles into Picoliter- and Femtoliter-Volume Droplets," Anal Chem. 77: 1539-1544 (2005).
Hebenstreit, "Methods, Challenges and Potentials of Single Cell RNA-seq," Biology (Basel). 1(3): 658-67 (2012).
Hiatt et al., "Parallel, tag-directed assembly of locally derived short sequence reads," Nat Methods. 7(2): 119-22 (2010).
Hirsch et al., "Easily reversible desthiobiotin binding to streptavidin, avidin, and other biotin-binding proteins: uses for protein labeling, detection, and isolation." Anal Biochem. 308(2):343-357 (2002).
Hjerten et al., "General methods to render macroporous stationary phases nonporous and deformable, exemplified with agarose and silica beads and their use in high-performance ion-exchange and hydrophobic-interaction chromatography of proteins," Chromatographia. 31.1-2: 85-94 (1991).
Holmberg et al., "The biotin-streptavidin interaction can be reversibly broken using water at elevated temperatures," Electrophoresis. 26(3):501-10 (2005).
Holtze, C. et al. Biocompatible surfactants for water-in-fluorocarbon emulsions. Lab Chip. Oct. 2008;8(10):1632-9. doi: 10.1039/b806706f. Epub Sep. 2, 2008.
Hosokawa et al., "Massively parallel whole genome amplification for single-cell sequencing using droplet microfluidics," Scientific Reports. 7: No. 5199 (2017).
Hosono et al., "Unbiased whole-genome amplification directly from clinical samples," Genome Res. 13(5):954-64 (2003).
Hu et al., "Shape Controllable Microgel Particles Prepared by Microfluidic Combining External Crosslinking," Biomicrofluidics. 6(2):26502-265029 (2012).
Huebner et al., "Quantitative detection of protein expression in single cells using droplet microfluidics," Chern Commun (Camb). (12):1218-1220 (2007).
Hug, H. et al. "Measurement of the No. of molecules of a single mRNA species in a complex mRNA preparation" J Theor Biol. Apr. 21, 2003;221(4):615-24.
Illumina Nextera Enrichment Sample Preparation Guide. Feb. 2013.
Illumina TruSeq Custom Enrichment Kit Data Sheet, (c) 2014.
Imburgio et al., "Studies of promoter recognition and start site selection by T7 Rna polymerase using a comprehensive collection of promoter variants," Biochemistry. 39(34):10419-30 (2000).
Invitrogen Dynal, Product Sheet for "Dynabeads® M-280 Streptavidin," (2006) (2 pages).
Loannidis, Nicolas, Thesis: "Manufacturing of agarose-based chromatographic adsorbents with controlled pore and particle sizes," Doctor of Philosophy in Chemical Engineering, The University of Birmingham, 2009.
Jena et al., "Cyclic olefin copolymer based microfluidic devices for biochip applications: Ultraviolet surface grafting using 2-methacryloyloxyethyl phosphorylcholine," Biomicrofluidics. 6(1): 12822-1282212 (2012).

(56) References Cited

OTHER PUBLICATIONS

Jin et al., "Genome-wide detection of DNase I hypersensitive sites in single cells and FFPE tissue samples," Nature. 528(7580): 142-6 (2015).
Joneja et al., "Linear nicking endonuclease-mediated strand-displacement DNA amplification," Anal Biochem. 414(1):58-69 (2011).
Jung et al., "Micro machining of injection mold inserts for fluidic channel of polymeric biochips," Sensors. 7(8): 1643-1654 (2007).
Kamperman et al., "Centering Single Cells in Microgels via Delayed Crosslinking Supports Long-Term 3D Culture by Preventing Cell Escape," Small. 13(22) (2017).
Kaper et al., "Supporting Information for Whole-genome haplotyping by dilution, amplification, and sequencing," Proc Natl Acad Sci U S A. 110(14):5552-7 (2013).
Kaper et al., "Whole-genome haplotyping by dilution, amplification, and sequencing," Proc Natl Acad Sci U S A. 110(14):5552-7 (2013),.
Karmakar et al., "Organocatalytic removal of formaldehyde adducts from RNA and DNA bases," Nat Chem. 7(9):752-8 (2015).
Katsura et al., "Indirect micromanipulation of single molecules in water-in-oil emulsion," Electrophoresis. 22(2): 289-93 (2001).
Kebschull et al., "High-Throughput Mapping of Single-Neuron Projections by Sequencing of Barcoded RNA," Neuron. 91(5):975-87 (2016).
Kenis et al., "Microfabrication Inside Capillaries Using Multiphase Laminar Flow Patterning," Science. 285(5424): 83-5 (1999).
Khomiakava et al., "Analysis of perfect and mismatched DNA duplexes by a generic hexanucleotide microchip," Mol Biol (Mosk). 37(4):726-41 (2003) (Abstract only).
Kim et al., "Albumin loaded microsphere of amphiphilic poly(ethylene glycol)/poly(a-ester) multiblock copolymer," Eu J Pharm Sci. 23: 245-51 (2004).
Kim et al., "Fabrication of monodisperse gel shells and functional microgels in microfluidic devices," Angew Chem Int Ed Engl. 46(11): 1819-22 (2007).
Kim et al., "Rapid prototyping of microfluidic systems using a PDMS/polymer tape composite," Lab Chip. 9(9): 1290-3 (2009).
Kirkness et al., "Sequencing of isolated sperm cells for direct haplotyping of a human genome," Genome Res. 23:826-83 (2013).
Kitzman et al., "Haplotype-resolved genome sequencing of a Gujarati Indian individual." Nat Biotechnol. 29:59-63 (2011).
Kitzman et al., "Noninvasive whole-genome sequencing of a human fetus," Sci Transl Med. 4(137):137ra76 (2016).
Kivioj, et al., "Counting Absolute Numbers of Molecules Using Unique Molecular Identifiers", Nature Methods 9, 72-74 (2012).
Klein et al., "Droplet barcoding for single-cell transcriptomics applied to embryonic stem cells," Cell. 161(5): 1187-201 (2015).
Knapp et al., "Generating barcoded libraries for multiplex high-throughput sequencing," Methods Mol Biol. 840:155-70 (2012).
Knight et al., "Subtle chromosomal rearrangements in children with unexplained mental retardation," Lancet. 354(9191):1676-81 (1999).
Kolodeziejczyk et al., "The technology and biology of single-cell RNA sequencing," Molecular Cell. 58(4): 610-20 (2015).
Korlach et al., "Methods in Enzymology, Real-Time DNA Sequencing from Single Polymerase Molecules," 472:431-455 (2010).
Koster et al., "Drop-based microfluidic devices for encapsulation of single cells", Lab on a Chip The Royal Soc. of Chem. 8:1110-1115 (2008).
Kozarewa et al., "96-plex molecular barcoding for the Illumina Genome Analyzer," Methods Mol Biol. 733:279-98 (2011).
Kozarewa et al., "Amplification-free Illumina sequencing-library preparation facilitates improved mapping and assembly of GC-biased genomes," Nat Methods. 6: 291-5 (2009).
Kutyavin, et al., "Oligonucleotides containing 2-aminoadenine and 2-thiothymine act as selectively binding complementary agents," Biochemistry. 35(34):11170-6 (1996).
Kwok et al., "Single-molecule analysis for molecular haplotyping," Hum Mutat. 23:442-6 (2004).
Lagally et al., "Single-Molecular DNA Amplification and Analysis in an Integrated Microfluidic Device," Anal Chem. 73(3): 565-70 (2001).
Lagus et al., "A review of the theory, methods and recent applications of high-throughput single-cell droplet microfluidics," J Phys D Appl Phys. 46:114005 (2013) (21 pages).
Lai et al., "Characterization and Use of Laser-Based Lysis for Cell Analysis On-Chip," Journal of the Royal Society. 5(2): S113-S121 (2008).
Laird et al., "Hairpin-bisulfite PCR: Assessing epigenetic methylation patterns on complementary strands of individual DNA molecules," PNAS.101, 204-209 (2004).
Lake et al., "Integrative Single-Cell Analysis By Transcriptional and Epigenetic States in Human Adult Brain," Apr. 19, 2017. doi: https://doi.org/10.1101/128520.
Lan et al. "Single-cell genome sequencing at ultra-high-throughput with microfluidic droplet barcoding" Nat Biotechnol. 35(7):640-646(2017).
Lander et al., "Initial sequencing and analysis of the human genome," Nature. 409: 860-921 (2001).
Lasken et al., "Archaebacterial DNA Polymerases Tightly Bind Uracil-containing DNA," J Biol Chem. 271 (30):17692-17696 (1996).
Lebedev et al.,. "Hot Start PCR with heat-activatable primers: a novel approach for improved PCR performance," NAR. 36(20):E131-1 (2008).
Lee et al., "Alginate: Properties and biomedical applications," Prog Polym Sci. 37(1 ):106-126 (2012).
Lee et al., "ACT-PRESTO: Rapid and consistent tissue clearing and labeling method for 3-dimensional (3D) imaging," Sci Rep. 6:18631 (2016).
Lee et al., "Fluorescent in situ sequencing (FISSEQ) of RNA for gene expression profiling in intact cells and tissues," Nature Protocols. 10(3):442-458 (2015).
Lee et al., "Highly multiplexed subcellular RNA sequencing in situ," Science. 343(6177): 1360-3 (2014).
Lennon et al., "A scalable, fully automated process for construction of sequence-ready barcoded libraries for 454," Genome Biol. 11(2):R15 (2010).
Li et al., "A single-cell-based platform for copy number variation profiling through digital counting of amplified genomic DNA fragments," ACS Appl Mater Interfaces, doi: 10.1021/acsami. 7b03146 (2017).
Li et al., "PEGylated PLGA Nanoparticles as protein carriers: synthesis, preparation and biodistribution in rats," Journal of Controlled Release. 71: 203-211 (2001).
Lienemann et al., "Single cell-laden protease-sensitive microniches for long-term culture in 3,". Lab Chip. 17(4):727-737(2017).
Linch et al., "Bone marrow processing and cryopreservation," Journal of Clinical Pathology. 35(2): 186-190(1982).
Liu et al., "Preparation of uniform-sized PLA microcapsules by combining Shirasu porous glass membrane emulsification technique and multiple emulsion-solvent evaporation method," J Control Release. 103(1): 31-43 (2005).
Liu et al., "Smart thermo-triggered squirting capsules for Nanoparticle delivery," Soft Matter. 6(16):3759-3763 (2010).
Lo et al., "On the design of clone-based haplotyping," Genome Biol. 14(9):R100 (2013).
Loscertales et al., "Micro/Nano Encapsulation via Electrified Coaxial Liquid Jets," Science. 295: 1695-1698 (2002).
Love, "A microengraving method for rapid selection of single cells producing antigen-specific antibodies," Nature Biotech. 24(6): 703 (2006).
Lowe, Adam James, Thesis: "Norbornenes and [n]polynorbornanes as molecular scaffolds for anion recognition," Doctor of Philosophy, Deakin University, 2010 (361 pages).
Lundin et al., "Hierarchical molecular tagging to resolve long continuous sequences by massively parallel sequencing," Sci Rep. 3:1186 (2003).
Lupski et al., "Genomic rearrangements and sporadic disease," Nat Genet. 39(7 Suppl):S43- 7 (2007).
Macaulay et al., "G&T-seq: parallel sequencing of single-cell genomes and transcriptomes," Nature Methods, p. 1-7 (2005).

(56) References Cited

OTHER PUBLICATIONS

Macaulay et al., "Single-Cell Multiomics: Multiple Measurements from Single Cells," available in PMS Dec. 18, 2017, published in final edited form as: Trends in Genetics. 33(2): 155-168 (2017).
Macosko et al., "Highly Parallel Genome-wide Expression Profiling of Individual Cells Using Nanoliter Droplets," Cell. 161(5): 1202-14 (2015).
Maeda et al., "Development of a DNA barcode tagging method for monitoring dynamic changes in gene expression by using an ultra high-throughput sequencer," Biotechniques. 45(1): 95-7 (2008).
Mair et al., "Injection molded microfluidic chips featuring integrated interconnects," Lab Chip. 6(10): 1346-54 (2006).
Makino et al., "Preparation of hydrogel microcapsules: Effects of preparation conditions upon membrane properties," Colloids and Surfaces B: Biointerfaces. 12(2): 97-104 (1998).
Mali et al., "Barcoding cells using cell-surface programmable DNA-binding domains," Nat Methods. 10(5): 403-6 (2013).
Mamedov et al., "Preparing unbiased T-cell receptor and antibody cDNA libraries for the deep next generation sequencing profiling," Front Immunol. 4: 456 (2013).
Man, Piu Francis, Thesis: "Monolithic Structures for Integrated Microfluidic Analysis," Doctor of Philosophy in Electrical Engineering, University of Michigan, 2001 (145 pages).
Marcus, "Gene method offers diagnostic hope," The Wall Street Journal, <https://www.wsj.com/articles/SB10001424052702303644004577520851224339844>, dated Jul. 11, 2012.
Margulies et al. "Genome sequencing in microfabricated high-density picoliter reactors", Nature (2005) 437:376-380.
Margulies, "Supplementary methods," (2005).
Maricic et al., "Optimization of 454 sequencing library preparation from small amounts of DNA permits sequence determination of both DNA strands," Biotechniques. 46(1 ):51-2, 54-7 (2009).
Matochko et al., "Uniform amplification of phage display libraries in monodisperse emulsions," Methods. 58(1): 18-27 (2012).
Mazutis et al., "Selective droplet coalescence using microfluidic systems," Lab Chip. 12(10): 1800-6 (2012).
McGinnis et al., "MULTI-seq: Scalable sample multiplexing for single-cell RNA sequencing using lipid-tagged indices," bioRxiv 387241; doi: https://doi.org/10.1101/387241.
Merriman et al., "Progress in ion torrent semiconductor chip based sequencing," Electrophoresis. 33(23): 3397-417 (2012).
Meyer et al., "From micrograms to picograms: quantitative PCR reduces the material demands of high-throughput sequencing," Nucleic Acids Research. 36(1): e5 (2008) (6 pages).
Meyer et al., "Targeted high-throughput sequencing of tagged nucleic acid samples," Nucleic Acids Res. 35(15): e97 (2007).
Microfluidic ChipShop, Microfluidic product catalogue, dated Mar. 2005.
Microfluidic ChipShop, Microfluidic product catalogue, dated Oct. 2009.
Mignardi et al., "Oligonucleotide gap-fill ligation for mutation detection and sequencing in situ," Nucl Acids Res. 43(22): e151 (2015).
Miller et al., "An improved zinc-finger nuclease architecture for highly specific genome editing," Nat Biotechnol. 25:778-785 (2007).
Miller-Stephenson Chemicals 157 FS Series catalog, www.miller-stephenon.com.
MiRNA (http://www.exiqon.com/what-are-microRNAs) accessed Oct. 19, 2017.
Mirzabekov, "DNA Sequencing by Hybridization—a Megasequencing Method and a Diagnostic Tool?" Trends in Biotechnology. 12(1): 27-32 (1994).
Moore et al., "Behavior of capillary valves in centrifugal microfluidic devices prepared by three-dimensional printing," Microfluidics and Nanofluidics. 10(4):877-888 (2011).
Morgan et al., "Chapter 12: Human microbiome analysis," PLoS Comput Biol. 8(12):e1002808 (2012).
Morimoto et al., "Monodisperse semi-permeable microcapsules for continuous observation of cells," Lab Chip 9(15):2217-2223 (2009).

Morton, "Parameters of the human genome," Proc Natl Acad Sci U S A. 88(17):7474-6 (1991).
Mouritzen et al., "Single nucleotide polymorphism genotyping using locked nucleic acid (LNa)," Expert Rev Mol Diagn. 3(1): 27-38 (2003).
Mozhanova et al., "Local elastic properties of biological materials studied by SFM," XP055314108, <http://www.ntmdt.com/data/media/files/publications/2003/08.08_a.a.mozhanova_n.i.n_english.pd f>, dated 2003.
Muotri et al., "L1 retrotransposition in neurons is modulated by MeCP2," Nature. 468(7322):443-6 (2010).
Myllykangas et al., "Targeted Sequencing Library Preparation By Genomic DNA Circularization," BMC Biotechnology. 11(122), 1-12 (2011).
Nagano et al., "Single-cell Hi-C reveals cell-to-cell variability in chromosome structure," Nature. 502(7469):59-64 (2013).
Nagashima et al., "Preparation of monodisperse poly (acrylamide-co-acrylic acid) hydrogel microspheres by a membrane emulsification technique and their size-dependent surface properties," Colloids and Surfaces B: Biointerfaces. 11(1-2): 47-56 (1998).
Narayanan et al., "Determination of agarose gel pore size: Absorbance measurements vis a vis other techniques," Journal of Physics: Conference Series 28. 83-86 (2006).
National Human Genome Research Institute (NHGRI), "The Human Genome Project Completion: Frequently Asked Questions," retrieved from <https://www.genome.gov/11006943/human-genome-project-completion-frequently-asked-questions/> on May 10, 2018, last updated Oct. 30, 2010 (8 pages).
Navin, "The first five years of single-cell cancer genomics and beyond," Genome Res. 25(10):1499-507 (2015).
Nguyen et al., "In situ hybridization to chromosomes stabilized in gel microdrops," Cytometry. 21(2):111-9 (1995).
Nisisako et al., "Droplet formation in a microchannel network," Lab Chip. 2(1):24-6 (2002).
Nisisako et al., "Droplet Formation in a Microchannel on PMMA Plate," *Micro Total Analysis Systems 2001*. J.M. Ramsey and A. van den Berg, 137-138 (2001).
Novak et al., "Single cell multiplex gene detection and sequencing using microfluidically-generated agarose emulsions," available in PMC Jan. 10, 2012, published in final edited form as: Angew Chem Int Ed Engl. 50(2):390-5 (2011) (10 pages).
Oberholzer et al., "Polymerase chain reaction in liposomes," Chem Biol. 2(10):677-82 (1995).
Ogawa et al., "Production and characterization of O/W emulsions containing cationic droplets stabilized by lecithin-chitosan membranes," J Agric Food Chem. 51(9):2806-12 (2003).
Okushima et al., "Controlled Production of Monodisperse Double Emulsions by Two-Step Droplet Breakup in Microfluidic Devices," Langmuir. 20(23):9905-8 (2004).
Oligotex Handbook. For purification of poly A+ RNA from total RNA and directly from cultured cells or tissues as well as purification of polyadenylated in vitro transcripts. Jun. 2012.
Orakdogen et al., "Novel responsive poly(N,N-dimethylaminoethyl methacrylate) gel beads: preparation, mechanical properties and pH-dependent swelling behavior," J Polym Res. 19:9914 (2012).
Oyola et al., "Optimizing Illumina next-generation sequencing library preparation for extremely AT-biased genomes," BMC Genomics. 13:1 (2012).
Pantel et al., "Detection methods of circulating tumor cells," J Thorac Dis. 4(5):446-7 (2012).
Park et al.,"ChIP-seq: advantages and challenges of a maturing technology," Nature Reviews Genetics. 10:669-680 (2009).
Patel et al., "Single-cell RNA-seq highlights intratumoral heterogeneity in primary glioblastoma," Science. 344(6190):1396-401 (2014).
PCT/IB2010/002243, International Search Report and Written Opinion, dated Feb. 9, 2011, 13pgs.
Perez et al., "Poly(lactic acid)-poly(ethylene glycol) Nanoparticles as new carriers for the delivery ofplasmid DNA," Journal of Controlled Release. 75: 211-224 (2001).
Perrott, "Optimization and Improvement of Emulsion PCR for the Ion Torrent Next- Generation Sequencing Platform," PhD Thesis(2011).

(56) References Cited

OTHER PUBLICATIONS

Peters et al., "Accurate whole-genome sequencing and haplotyping from 10 to 20 human cells," Nature. 487(7406):190-5 (2012).
Pfeifer et al., "Bivalent cholesterol-based coupling of oligonucleotides to lipid membrane assemblies," J Am Chem Soc. 126(33): 10224-5 (2004).
Picot et al., "A biomimetic microfluidic chip to study the circulation and mechanical retention of red blood cells in the spleen" Am J Hematology. 90(4):339-345 (2015).
Pinto et al., "Functional impact of global rare copy number variation in autism spectrum disorders," Nature. 466(7304):368-72 (2015).
Plunkett et al., "Chymotrypsin responsive hydrogel: application of a disulfide exchange protocol for the preparation of methacrylamide containing peptides," Biomacromolecules. 6(2):632-7 (2005).
Porteus et al., "Chimeric nucleases stimulate gene targeting in human cells," Science. 300(5620):763 (2003).
Pott et al., "Single-cell ATAC-seq: strength in numbers," Genome Biol.16(1):172 (2015).
Preissl et al., "Single nucleus analysis of the chromatin landscape in mouse forebrain development," bioRxiv 159137 (2017).
Qiagen, "Omniscript® Reverse Transcription Handbook," Oct. 2010 (32 pages).
Rakszewska et al., "One drop at a time: toward droplet microfluidics as a versatile tool for single-cell analysis," NPG Asia Materials. 6(10):e133 (2014) (12 pages).
Ram et al., "Strategy for microbiome analysis using 16S rRNA gene sequence analysis on the Illumina sequencing platform," Syst Biol Reprod Med. 57(3):162-70 (2011).
Ramsey, "The burgeoning power of the shrinking laboratory" Nat Biotechnol. 17(11):1061-2 (1999).
Ramskold et al., "Full-length mRNA-Seq from single-cell levels of RNA and individual circulating tumor cells" Nat Biotechnol. 30(8):777-782 (2012).
Ran et al., "Genome Engineering Using the CRISPR-Cas9 System," Nature Protocol. 8(11):2281-2308 (2013).
Reis et al., "CRISPR/Cas9 and Targeted Genome Editing: A New Era in Molecular Biology," XP002766825: URL:https://ww.neb.com/tools-and-resources/feabture-articles/crispr- cas9-and-targeted-genome-editing-a-new-era-in-molecular-biology (2014).
Reisner et al., "Single-molecule denaturation mapping of DNA in nanofluidic channels," Proc Natl Acad Sci U S.A., 107: 13294-9,(2010).
Repp et al., "Genotyping by Multiplex Polymerase Chain Reaction for Detection of Endemic Hepatitis B Virus Transmission," J Clinical Microbiology. 31:1095-1102 (1993).
Richardson et al., "Novel inhibition of archaeal family-D DNA polymerase by uracil," Nucleic Acids Res. 41(7):4207-18 (2013).
Roche, "Using Multiplex Identifier (MID) Adaptors for the GS FLX Titanium Chemistry Basic MID Set Genome Sequencer FLX System," Technical Bulletin 004-2009, <http://454.com/downloads/my454/documentation/technical-bulletins/TCB-09004 Using Multi plexIdentifierAdaptorsForTheGSFLXTitaniumSeriesChemistry-BasicMIDSet.pdf>, dated Apr. 1, 2009 (7 pages).
Roche, "Using Multiplex Identifier (MID) Adaptors for the GS FLX Titanium Chemistry Extended MID Set Genome Sequencer FLX System," Technical Bulletin 005-2009, <http://454.com/downloads/my454/documentation/technical-bulletins/TCB-09005UsingMultipl exIdentifierAdaptorsForTheGSFLXTitaniumChemistry-ExtendedMIDSet.pdf>, dated Apr. 1, 2009 (7 pages).
Rodrigue et al., "Whole genome amplification and de novo assembly of single bacterial cells," PLoS One. 4(9):e6864 (2009).
Rogozin et al., "A highly conserved family of inactivated archaeal B family DNA polymerases," Biol Direct. 3:32 (2008).
Ropers, "New perspectives for the elucidation of genetic disorders," Am J Hum Genet. 81(2):199-207 (2007).
Rotem et al., "High-Throughput Single-Cell Labeling (Hi-SCL) for RNA-Seq Using Drop-Based Microfluidics," PLoS One. 10(5):e0116328 (2015).
Rotem et al., "Single Cell Chip-Seq Using Drop-Based Microfluidics," Frontiers of Single Cell Analysis, September 5-7, Stanford University. Abstract #50 (2013).
Rotem et al., "Single-cell ChIP-seq reveals cell subpopulations defined by chromatin state," Nat Biotechnol. 33(11):1165-72 (2015).
Ryan et al., "Rapid assay for mycobacterial growth and antibiotic susceptibility using gel microdrop and encapsulation," J Clin Microbiol. 33(7):1720-6 (1995).
Sakaguchi et al., "Cautionary Note on the Use of dUMP-Containing PCR Primers with Pfu and VentR®," BioTechniques. 21(3): 369-370 (1996).
Sander et al., "Selection-free zinc-finger-nuclease engineering by context-dependent assembly (CoDA)," Nat Methods. 8(1):67-9 (2011).
Savva et al., "The structural basis of specific base-excision repair by uracil-DNA glycosylase," Nature. 373(6514):487-93 (1995).
Schirinzi et al., "Combinatorial sequencing-by-hybridization: aNalysis of the NFI gene," Genet Test. 10(1):8-17(2006).
Schmeider et al., "Fast identification and removal of sequence contamination from genomic and metagenomic datasets," PLoS One. 6(3):e17288 (2011).
Schmitt et al., "Bead-based multiplex genotyping of human papillomaviruses," J Clin Microbiol. 44(2):504-12(2006).
Schubert et al., "Microemulsifying fluorinated oils with mixtures of fluorinated and hydrogenated surfactants," Colloids and Surfaces A: Physicochemical and Engineering Aspects. 84(1):97-106 (1994).
Schwartz et al., "Capturing native long-range contiguity by in situ library construction and optical sequencing," Proc Natl Acad Sci U S A. 109(46):18749-54 (2012).
Sebat et al., "Strong association of de novo copy number mutations with autism," Science. 316(5823):445-9 (2007).
Seiffert et al., "Microfluidic fabrication of smart microgels from macromolecular precursors," Polymer. 51(25):5883-9 (2010).
Seiffert et al., "Smart microgel capsules from macromolecular precursors," J Am Chem Soc. 132(18):6606-9 (2010).
Shah, "Fabrication of mono disperse thermosensitive microgels and gel capsules in micro fluidic devices", Soil Matter 4:2303-2309 (2008).
Shahi et al., "Abseq: Ultrahigh-throughput single cell protein profiling with droplet microfluidic barcoding," Sci Rep. 7:44447 (2017).
Shaikh et al., "A modular microfluidic architecture for integrated biochemical analysis," Proc Natl Acad Sci U S A. 102(28) :9745-9750 (2005).
Shimkus et al., "A chemically cleavable biotinylated nucleotide: usefulness in the recovery of protein-DNA complexes from avidin affinity columns," Proc Natl Acad Sci U S A. 82(9):2593-7 (1985).
Shlien et al., "Copy number variations and cancer," Genome Med. 1(6):62 (2009).
Shlien et al., "Excessive genomic DNA copy number variation in the Li-Fraumeni cancer predisposition syndrome," Proc Natl Acad Sci U S A. 105(32):11264-9 (2008).
Shuttleworth et al., "Recognition of the pro-mutagenic base uracil by family B DNA polymerases from archaea," J Mol Biol. 337(3):621-34 (2004).
Simeonov et al., "Single nucleotide polymorphism genotyping using short, fluorescently labeled locked nucleic acid (LNA) probes and fluorescence polarization detection," Nucleic Acids Res. 30(17):e91 (2002).
Simon et al., "Using formaldehyde-assisted isolation of regulatory elements (FAIRE) to isolate active regulatory DNA," Nat Protoc. 7(2):256-67 (2012).
Skerra, "Phosphorothioate primers improve the amplification of DNA sequences by DNA polymerases with proofreading activity," Nucleic Acids Res. 20(14):3551-4 (1992).
Smith et al., "Highly-multiplexed barcode sequencing: an efficient method for parallel analysis of pooled samples," Nucleic Acids Res. 38(13):e142 (2010).
Song et al., "DNase-seq: A High-Resolution Technique for Mapping Active Gene Regulatory Elements across the Genome from Mammalian Cells," Cold Spring Harb Protoc. 2 (2010) (13 pages).
Song et al., "Reactions in droplets in microfluidic channels," Angew Chem Int Ed Engl. 45(44):7336-56 (2006).

(56) References Cited

OTHER PUBLICATIONS

Sorokin et al., "Discrimination between perfect and mismatched duplexes with oligonucleotide gel microchips: role of thermodynamic and kinetic effects during hybridization," J Biomol Struct Dyn. 22(6):725-34 (2005).
Stoeckius et al., "Large-scale simultaneous measurement of epitopes and transcriptomes in single cells," available in PMC Jan. 31, 2018, published in final edited form as: Nat Methods. 14(9):865-868 (2017).
Stoeckius et al., "Simultaneous epitope and transcriptome measurement in single cells," Nat Methods. 14: 865-868 (2017) (Supplemental Materials).
Su et al., "Microfluidics-Based Biochips: Technology Issues, Implementation Platforms, and Design-Automation Challenges," IEEE Transactions on Computer-Aided Design of Integrated Circuits and Systems. 25(2):211-23 (2006).
Sun et al., "Progress in research and application of liquid-phase chip technology," Chin J Exp Surg. 22(5):639-40 (2005) (7 pages).
Susaki et al., "Whole-brain imaging with single-cell resolution using chemical cocktails and computational analysis," Cell. 157(3):726-39 (2014).
Syed, et al. Nature Methods 2 pgs (Nov. 2009).
Tawfik, D.S. et al. "Man-made cell-like compartments for molecular evolution" Nature Biotech (Jul. 1998) 16:652-656.
Tayyab et al., "Size exclusion chromatography and size exclusion HPLC of proteins," Biochem Ed, Pergamon. 19(3):149-152 (1991).
Tewhey et al., "Microdroplet-based PCR amplification for large-scale targeted sequencing," available in PMC May 1, 2010, published in final edited form as: Nat Biotechnol. 27(11):1025-31 (2009) (22 pages).
Tewhey et al., "Supplementary Materials," Nature Biotechnology. 27(11): 1-22 (2009).
Thaxton et al., "A Bio-Bar-Code Assay Based Upon Dithiothreitol Oligonucleotide Release" Anal Chem. 77:8174-8178 (2005).
Theberge, A.B, et al. Microdropelts in microfluidics: an evolving platform for discoveries in chemistry and biology. Angew Chem Int Ed Engl. Aug. 9, 2010;49(34):5846-68. doi: 10.1002/anie.200906653.
Thorsen et al., "Dynamic pattern formation in a vesicle-generating microfluidic device," Phys Rev Lett. 86(18):4163-4166 (2001).
Tomer et al., "Advanced CLARITY for rapid and high-resolution imaging of intact tissues," Nat Protoc. 9(7):1682-97 (2014).
Tonelli et al., "Perfluoropolyether functional oligomers: unusual reactivity in organic chemistry" Journal of Fluorine Chemistry. 118(1-2):107-21 (2002).
Tubeleviciute et al., "Compartmentalized self-replication (CSR) selection of *Thermococcus litoralis* Sh1B DNA polymerase for diminished uracil binding," Protein Eng Des Sel. 23(8):589-97 (2010).
Turner et al., "Assaying chromosomal inversions by single-molecule haplotyping," Nat Methods. 3(6):439-45 (2006).
Turner et al., "High-throughput haplotype determination over long distances by haplotype fusion PCR and ligation haplotyping," Nat Protoc. 4(12):1771-83 (2009).
Turner et al., "Methods for genomic partitioning," Annu Rev Genomics Hum Genet. 10:263-84 (2009).
Ullal et al., "Cancer Cell Profiling by Barcoding Allows Multiplexed Protein Analysis in Fine-Needle Aspirates," Sci Transl Med. 6(219): 219ra9 (2014).
Ushijima et al., "Detection and interpretation of altered methylation patterns in cancer cells," Nat Rev Cancer. 5: 223-231 (2005).
Van Nieuwerburgh et al., "Illumina mate-paired DNA sequencing-library preparation using Cre-Lox recombination," Nucleic Acids Res. 40(3): e24 (2012).
Wagner et al., "Biocompatible fluorinated polyglycerols for droplet microfluidics as an alternative to PEG-based copolymer surfactants," Lab Chip. 16(1):65-9 (2016).
Wang et al., "A novel thermo-induced self-bursting microcapsule with magnetic-targeting property," Chemphyschem. 10(14):2405-9 (2009).
Wang et al., "Digital karyotyping," Proc Natl Acad Sci U S A. 99(25):16156-61 (2002).
Wang et al., "Self-Formed Adaptor PCR: a Simple and Efficient Method for Chromosome Walking," Appl Environ Microbiol. 73(15):5048-51 (2007).
Wang et al., "Single nucleotide polymorphism discrimination assisted by improved base stacking hybridization using oligonucleotide microarrays," Biotechniques. 35(2):300-8 (2003).
Ward et al., "Microfluidic flow focusing: drop size and scaling in pressure versus flow-rate-driven pumping," Electrophoresis. 26(19):3716-24 (2005).
Weaver, J.C. et al. "Rapid clonal growth measurements at the single-cell level: gel microdroplets and flow cytometry", Biotechnology, 9:873-877 (1991).
Weigl et al., "Microfluidic Diffusion-Based Separation and Detection," Science. 283(5400):346-7 (1999).
Wesolowska et al., "Cost-effective multiplexing before capture allows screening of 25 000 clinically relevant SNPs in childhood acute lymphoblastic leukemia," Leukemia. 25(6):1001-6 (2011).
Whitesides et al., "Soft lithography in biology and biochemistry," Annu Rev Biomed Eng. 3:335-73 (2001).
Williams, R. et al. "Amplification of complex gene libraries by emulsion PCR" Nature Methods (Jul. 2006) 3(7):545-550.
Wiseman et al., "Major histocompatibility complex genotyping with massively parallel pyrosequencing," Nat Med. 15(11):1322-6 (2009).
Wong et al., "Multiplexed Barcoded CRISPR-Cas9 Screening Enabled By CombiGEM," Proc Natl Acad Sci U S A. 113(9):2544-9 (2016).
Woo et al., "G/C-modified oligodeoxynucleotides with selective complementarity: synthesis and hybridization properties," Nucleic Acids Res. 24(13):2470-5 (1996).
Wood et al., "Targeted genome editing across species using ZFNs and TALENs," Science. 333(6040):307 (2011).
Xi et al., "New library construction method for single-cell genomes," PLoS One. 12(7):e0181163 (2017).
Xia et al., "Soft Lithography," Angew Chem Int Ed Engl. 37(5):550-575 (1998).
Xia et al., "Soft Lithography," Ann Rev Mat Sci. 28:153-184 (1998).
Xiao et al., "Determination of haplotypes from single DNA molecules: a method for single-molecule barcoding," Hum Mutat. 28(9):913-21 (2007).
Yamamoto et al., "Chemical modification of Ce(IV)/EDTA-based artificial restriction DNA cutter for versatile manipulation of double-stranded DNA," Nucleic Acids Res. 35(7):e53 (2007).
Yan et al., "Rapid one-step construction of hairpin RNA," Biochem Biophys Res Commun. 383(4):464-8 (2009).
Zeng et al., "High-performance single cell genetic analysis using microfluidic emulsion generator arrays," Anal Chem. 82(8):3183-90 (2010).
Zentner et al., "Surveying the epigenomic landscape, one base at a time," Genome Biol. 13(10):250 (2012).
Zhang et al., "Combinatorial marking of cells and organelles with reconstituted fluorescent proteins," Cell. 119(1):137-144 (2004).
Zhang et al., "Degradable disulfide core-cross-linked micelles as a drug delivery system prepared from vinyl functionalized nucleosides via the RAFT process," Biomacromolecules. 9(11):3321-31 (2008).
Zhang et al., "Efficient construction of sequence-specific TAL effectors for modulating mammalian transcription," Nat Biotechnol. 29(2):149-53 (2011).
Zhang et al., "One-step fabrication of supramolecular microcapsules from microfluidic droplets," Science. 335(6069):690-4 (2012).
Zhang et al., "Reconstruction of DNA sequencing by hybridization," Bioinformatics. 19(1):14-21 (2003).
Zhang, Michael Yu, Thesis: "Genomics of inherited bone marrow failure and myelodysplasia," Doctor of Philosophy in Molecular and Cellular Biology, University of Washington, 2015 (142 pages).
Zhao et al., "Preparation of hemoglobin-loaded Nano-sized particles with porous structure as oxygen carriers," Biomaterials. 28(7):1414-1422 (2007).
Zheng et al., "Haplotyping germline and cancer genomes with high-throughput linked-read sequencing," Nat Biotechnol. 34(3):303-11 (2016).

(56) References Cited

OTHER PUBLICATIONS

Zheng et al., "Massively parallel digital transcriptional profiling of single cells," Nat Commun. 8:14049 (2017).
Zhou et al., "Development of an enzyme activity screening system for beta-glucosidase-displaying yeasts using calcium alginate microbeads and flow sorting," Appl Microbiol Biotechnol. 84: 375-382 (2009).
Zhu et al., "Hydrogel Droplet Microfluidics for High-Throughput Single Molecule/Cell Analysis," Accounts of Chemical Research. 50(1): 22-31 (2016).
Zhu et al., "Reverse transcriptase template switching: a SMART approach for full-length cDNA library construction," Biotechniques. 30(4):892-7 (2001).
Zhu et al., "Synthesis and self-assembly of highly incompatible polybutadiene-poly(hexafluoropropylene oxide) diblock copolymers," J Polymer Sci Part B: Polymer Phys. 43(24):3685-3694 (2005).
Zimmermann et al., "Microscale production of hybridomas by hypo-osmolar electrofusion," Hum Antibodies Hybridomas. 3(1):14-8 (1992).
Zong et al., "Genome-wide detection of single-nucleotide and copy-number variations of a single human cell," Science. 338(6114):1622-6 (2012).

\* cited by examiner

Fig. 1G

| Sample Description | Depth Positional CV Deduped on Confident Regions | Effective Amplification Rate | Chimera Rate from Distant Reads | Q35 or Greater Error Rate | Effective Barcode Diversity | Mean Reads Per Fragment on N50 Barcodes | Mean Depth | Mean Dup Rate using barcodes | Unmapped Fraction |
|---|---|---|---|---|---|---|---|---|---|
| All | < 0.55 | > 5.0 | < 0.05 | < 0.0004 | > 150000.0 | 3 | 2 | 2 | < 0.05 |
| Priority | 3 | 3 | 3 | 3 | 3 | | | | 2 |
| 2 step purification | 0.47 | 7.97 | 0.083 | 0.0011 | 162445 | 2.70 | 9.86 | 1.00 | 0.036 |
| 1 step purification | 0.48 | 10.04 | 0.094 | 0.0011 | 183076 | 2.31 | 9.43 | 1.00 | 0.052 |

| Sample Description | Median insert Size | Mean Quality Read 1 | Mean Quality Read 2 | Mean Quality Barcode Read | Read 1 Start Site Relative Entropy | Read 2 Start Site Relative Entropy | Fraction Observed Barcodes on Whitelist | CV of Barcode Count | Fraction of SNPs phased (Universal Mode) |
|---|---|---|---|---|---|---|---|---|---|
| All | | > 36.0 | > 36.0 | > 35.0 | < 2.0 | < 2.0 | > 0.95 | | |
| Priority | 2 | 2 | 2 | 2 | 2 | 2 | 2 | 2 | 2 |
| 2 step purification | 181 | 36.22 | 33.41 | 33.95 | 1.01 | 0.26 | 0.77 | 1.35 | 0.64 |
| 1 step purification | 181 | 36.11 | 33.25 | 33.79 | 1.01 | 0.27 | 0.76 | 1.37 | 0.59 |

Fig. 4B

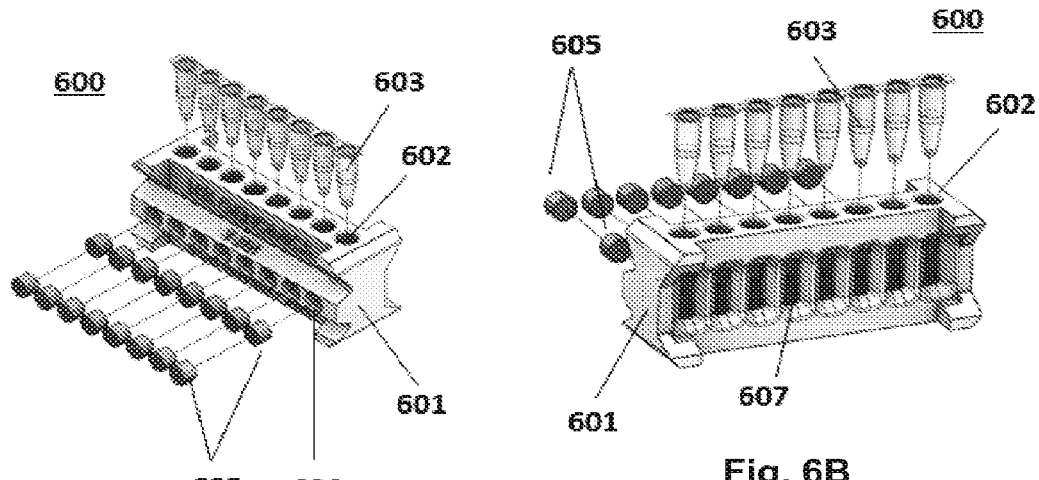
Fig. 6A
Fig. 6B
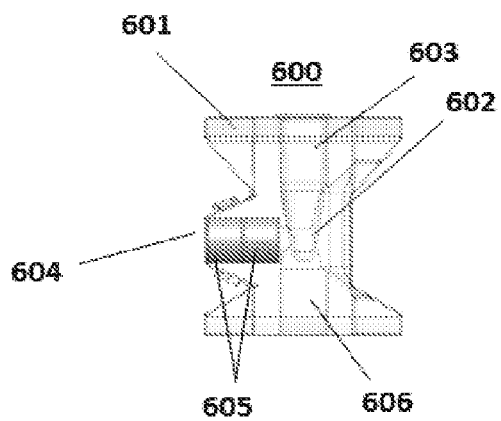
Fig. 6C

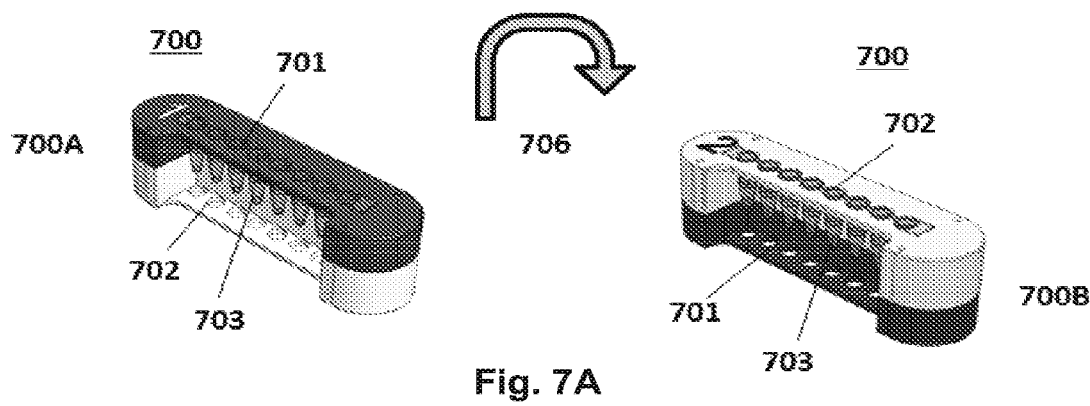
Fig. 7A
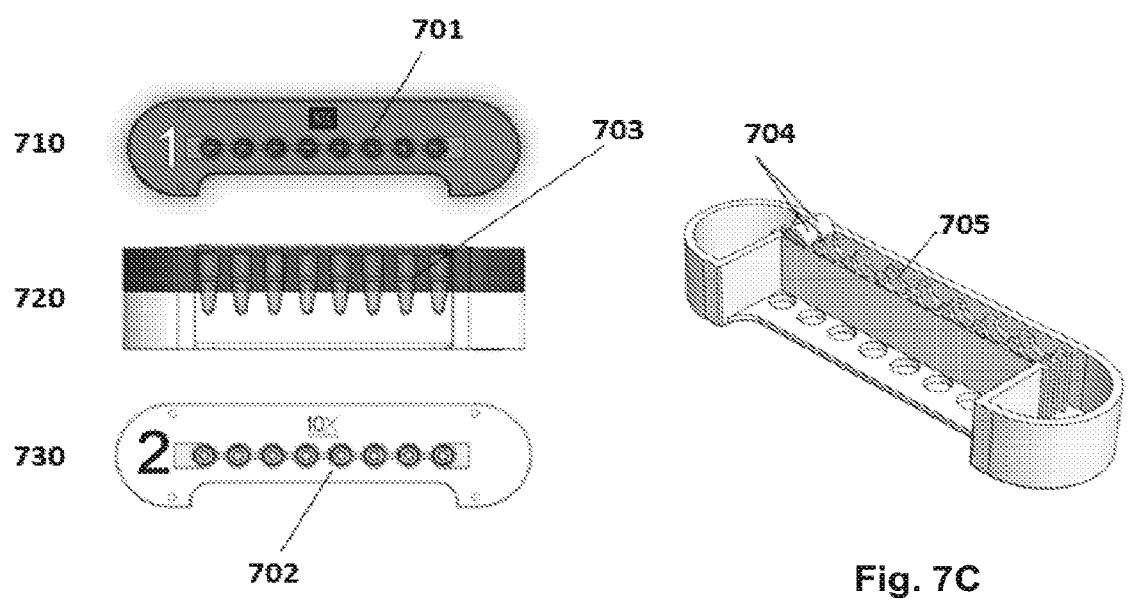
Fig. 7B
Fig. 7C

PARTITION PROCESSING METHODS AND SYSTEMS

CROSS REFERENCE TO RELATED APPLICATIONS

This application claims priority to U.S. Provisional Patent Application No. 62/119,930 filed Feb. 24, 2015 the full disclosure of which is incorporated herein by reference in its entirety for all purposes.

BACKGROUND

Nucleic acid sequencing technology has experienced rapid and massive advances over recent years. As compared to gel based separation methods where nested sets of terminated sequence extension products were interpreted visually by scientists, today's sequencing technologies produce enormous amounts of sequence data, allow illumination of never before sequenced genomes and genome regions, and provide throughput and costs that allow the widespread adoption of sequencing into routine biological research and diagnostics.

Droplet-based microfluidic techniques are becoming a popular method of preparing molecules for sequencing due to massive high-throughput, low reagent cost, and ease of preparation. However, droplet chemistry generates a complex mixture of chemicals and biological products that can impact the outcome of downstream applications. Therefore, there exists a need for improved methods of purifying molecules from droplets.

SUMMARY

An aspect of the disclosure provides a method for recovering target molecules from a plurality of droplets, comprising: a) providing a plurality of droplets having contents that comprise a plurality of target molecules; b) releasing the contents from the plurality of droplets to provide released target molecules; c) contacting the released target molecules with one or more supports, wherein the one or more supports bind the released target molecules to provide bound target molecules, and wherein the one or more supports comprises at least one component responsive to a magnetic force; and d) applying the magnetic force to the one or more supports.

In some cases, releasing the contents from the plurality of droplets to provide released target molecules further comprises destabilizing the plurality of droplets, thereby releasing the contents from the plurality of droplets. In some cases, the plurality of droplets comprise droplets in an emulsion and releasing the contents from the plurality of droplets to provide released target molecules further comprises contacting the emulsion with a destabilization agent that destabilizes the emulsion, thereby releasing the contents from the plurality of droplets. In some cases, the destabilization agent comprises perfluorooctanol.

In some cases, releasing the contents from the plurality of droplets to provide released target molecules further comprises releasing the contents from the plurality of droplets into a pooled mixture, wherein the pooled mixture comprises the released target molecules.

In some cases, the contacting step further comprises contacting the released molecules with the one or more supports by providing the one or more supports to the pooled mixture. In some cases, the contacting step further comprises contacting the released target molecules with the one or more supports in the presence of a chaotrope that aids in the one or more supports binding the released target molecules. In some cases, the chaotrope comprises guanadine thiocyanate or guanidine hydrochloride.

In some cases, the method provides for, after applying the magnetic force, releasing the bound target molecules from the one or more supports to provide re-released target molecules. In some cases, releasing is completed with the aid of an elution agent. The elution agent may comprise one or more of the following, without limitation: water, Tris buffer, phosphate buffer, and sodium hydroxide. Moreover, in some cases, prior to releasing the bound target molecules from the one or more supports, the method further comprises washing the one or more supports in one or more wash cycles by contacting the one or more supports with a washing agent. In some cases, the washing agent comprises ethanol, isopropanol and/or acetone. In some cases, the method comprises, after releasing the bound target molecules from the one or more supports, subjecting the re-released target molecules to a solid phase reversible immobilization process.

In some cases, the target molecules comprise target nucleic acid molecules. In some cases, the method further comprises, after the contacting step, determining sequences of the target nucleic acid molecules. In some cases, the method comprises, after the contacting step, appending one or more additional nucleotides to the target nucleic acid molecules to provide larger target nucleic acid molecules. In some cases, the method further comprises determining sequences of the larger target nucleic acid molecules.

In some cases, the target molecules comprise one or more of a small molecule, a protein, or a peptide.

In some cases, the at least one component comprises a magnetic particle.

In some instances, the one or more supports are functionalized with a silanol that aids in the one or more supports binding the target molecules. In some cases, the one or more supports are functionalized with a carboxylate that aids in the one or more supports binding the target molecules.

Further, the contents of the plurality of droplets may comprise one or more nucleic acid molecules. The contents may further comprise a polymerase. The contents may further comprise a primer. In some cases, the primer comprises a barcode sequence. Further, the primer may comprise a random N-mer.

In some cases, the contents of the plurality of droplets further comprise one or more polymeric species. The polymeric species may comprise polyacrylamide. The polyacrylamide may comprise a linear polyacrylamide. In some cases, the polyacrylamide may comprise agarose. In some instances, the contents of the plurality of droplets may further comprise a reducing agent.

In some cases, the plurality of droplets comprises aqueous droplets. Further, the plurality of droplets may comprise at least about 1,000 droplets, at least about 10,000 droplets, at least about 100,000 droplets, at least about 1,000,000 droplets or at least about 10,000,000 droplets.

In some aspects, the disclosure provides a method for purifying a target molecule, comprising: a) in a vessel, providing a support to a liquid mixture comprising contents of a destabilized droplet that comprise a target molecule, wherein the support binds the target molecule to provide a bound target molecule; b) immobilizing the support at a first location of the vessel, thereby separating the support from the liquid mixture; c) removing the liquid mixture from the vessel; d) providing a suspension fluid to the vessel, thereby suspending the support in the suspension fluid; and e) immobilizing the support at a second location of the vessel, thereby separating the support from the suspension fluid, wherein the second location of the vessel is different than the first location of the vessel.

In some cases, in a), the liquid mixture further comprises a chaotrope that aids in the support binding the target molecule. The chaotrope may comprise guanadine thiocyanate or guanidine hydrochloride. In some cases, in a), the liquid mixture further comprises a polymeric species. The polymeric species may comprise polyacrylamide. Furthermore, the polyacrylamide may comprise a linear polyacrylamide. In some cases, the polymeric species may comprise agarose.

In some cases, in a), the droplet is an aqueous droplet. Further, in some cases, in a), the liquid mixture further comprises a destabilization agent capable of destabilizing an emulsion. The destabilization agent may comprise PFO. Moreover, in some cases, in a), the liquid mixture further comprises a primer. The primer may comprise a barcode sequence. In some cases, the primer comprises a random N-mer. Furthermore, in a), the liquid mixture may further comprise a reducing agent.

In some cases, the immobilizing step further comprises magnetically immobilizing the support at the first location of the vessel. In some examples, the removing step further comprises removing the liquid mixture from the vessel via suction. In some cases, the removing step further comprises removing the liquid mixture from the vessel via decanting. In some cases, in d), the suspension fluid comprises ethanol, isopropanol or acetone.

In some cases, the second immobilizing step further comprises magnetically immobilizing the support at the second location of the vessel.

In some cases, the method further comprises, after e), releasing the bound target molecule from the support, to provide a released target molecule. In some cases, releasing is completed with the aid of an elution agent. The elution agent may comprise one or more of the following, without limitation: water, Tris buffer, phosphate buffer, and sodium hydroxide.

In some cases, prior to releasing the bound target molecule from the support, the method can further comprise washing the support in one or more wash cycles by contacting the support with a washing agent. The washing agent may comprise one or more of the following, without limitation: ethanol, isopropanol, and acetone.

In some cases, after releasing the bound target molecule from the support, the method can further comprise subjecting the released target molecule to a solid phase reversible immobilization process. In some cases, the target molecule comprises a target nucleic acid molecule. Furthermore, after e), the method can further comprise determining a sequence of the target nucleic acid molecule. In some cases, after e), the method may further comprise appending one or more additional nucleotides to the target nucleic acid molecule to provide a larger target nucleic acid molecule. In some cases, the method may further comprise determining a sequence of the larger target nucleic acid molecule. The target molecule may comprise a small molecule, a protein, a peptide.

In some cases, the support comprises a magnetic material. In some cases, the support comprises a particle. Furthermore, the support may be functionalized with a silanol that aids the support in binding the target molecule. In some cases, the support is functionalized with a carboxylate that aids the support in binding the target molecule.

In some cases, the vessel may be a tube, a well, a dish and/or a container.

Another aspect of the disclosure provides a method for purifying a target molecule, comprising: a) in a vessel, providing a liquid mixture comprising: a target molecule; a support configured to bind the target molecule; a fluorinated oil; and a chaotrope; b) binding the target molecule to the support to provide a bound target molecule, wherein the chaotrope aids in binding the target molecule to the support; and c) separating the support from the liquid mixture under conditions that immobilize the support to a surface of the vessel.

In some cases, the fluorinated oil comprises a fluorocarbon oil. The fluorinated oil may comprise hexafluoropropylene epoxide or a polymer thereof. The liquid mixture may further comprise a fluorosurfactant. In some cases, the chaotrope comprises guanadine thiocyanate or guanidine hydrochloride.

In some cases, the liquid mixture further comprises a polymeric species. The polymeric species may comprise polyacrylamide. The polyacrylamide may comprise a linear polyacrylamide. In some cases, the polymeric species may comprise agarose. The liquid mixture may further comprise a destabilization agent capable of destabilizing an emulsion. The destabilization agent may comprise perfluorooctanol. In some cases, the liquid mixture further comprises a primer. The primer may comprise a barcode sequence. The primer may comprise a random N-mer. Furthermore, the liquid mixture may further comprise a polymerase. The liquid mixture may further comprise a reducing agent.

In some cases, the separating step further comprises separating the support from the liquid mixture under conditions that magnetically immobilize the support to the surface of the vessel. In some cases, after c), the method may further comprise releasing the bound target molecule from the support to provide a released target molecule. The releasing step may be completed with the aid of an elution agent. The elution agent may comprise one or more of the following, without limitation: water, Tris buffer, phosphate buffer, and sodium hydroxide.

The method may further comprise, prior to releasing the bound target molecule from the support, washing the support in one or more wash cycles by contacting the magnetic support with a washing agent. The washing agent may comprise one or more of the following, without limitation: ethanol, isopropanol, and acetone. Furthermore, after releasing the bound target molecule from the support, the method can further comprise subjecting the released target molecule to a solid phase reversible immobilization process. The target molecule may comprise a target nucleic acid molecule. The method may further comprise, after the separating step, determining a sequence of the target nucleic acid molecule.

In some cases, after the separating step, the method may further comprise appending one or more additional nucleotides to the target nucleic acid molecule to provide a larger target nucleic acid molecule. Furthermore, the method may comprise determining a sequence of the larger target nucleic acid molecule. The target molecule comprises a small molecule, a protein, a peptide.

In some cases, the support comprises a magnetic material. In some cases, the support comprises a particle. In some instances, the support is functionalized with a silanol that aids in binding the target molecule to the support. In other instances, the support is functionalized with a carboxylate that aids in binding the target molecule to the support.

In some examples, the vessel may be a tube, a well, a dish and/or a container.

Another aspect of the disclosure provides for a method for sequencing a nucleic acid library, comprising: a) generating a library of nucleic acid molecules, wherein the library comprises a plurality of droplets comprising the nucleic acid molecules; b) destabilizing the plurality of droplets, thereby releasing the nucleic acid molecules from the plurality of droplets into a common pool; c) recovering the nucleic acid molecules from the common pool to provide recovered nucleic acid molecules, wherein recovering comprises: i) in the common pool, immobilizing the nucleic acid molecules to a plurality of supports; and ii) isolating the plurality of supports; and d) determining sequences of at least a subset of the recovered nucleic acid molecules.

In some cases, the nucleic acid molecules comprise a barcode sequence. In some cases, the nucleic acid molecules comprise a random N-mer.

In some instances, the plurality of droplets comprises droplets in an emulsion. Furthermore, the destabilizing step may comprise destabilizing the emulsion.

In some cases, the plurality of supports comprises particles.

Furthermore, the generating step may comprise barcoding sample nucleic acid molecules in the plurality of droplets. Moreover, the immobilizing step may comprise, binding the nucleic acid molecules to the plurality of supports via one or more ionic interactions. Furthermore, the isolating step of c) may comprise subjecting the plurality of supports to one or more cycles of magnetic separation. The isolating step of c) may further comprise subjecting the plurality of supports to one or more cycles of centrifugation. In some cases, the method further comprises, prior to d), releasing the recovered nucleic acid molecules from the plurality of supports. In some cases, the method can further comprise appending one or more additional nucleotides to each of the recovered nucleic acid molecules to provide larger nucleic acid molecules. Furthermore, in d), determining sequences of at least the subset of the recovered nucleic acid molecules may comprise determining sequences of at least a subset of larger nucleic acid molecules.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 1A-1G provide a schematic illustration of an example method for barcoding and amplification of nucleic acid fragments;

FIG. 4B graphically illustrates sequencing data obtained from experiments described in Example 3;

FIGS. 6A-6C schematically illustrate an example magnetic separation device; FIG. 7A schematically illustrates an example magnetic separation device and its use;

FIGS. 7B and 7C provide additional view of the example magnetic separation device of FIG. 7A.

DETAILED DESCRIPTION

Figure 1A:
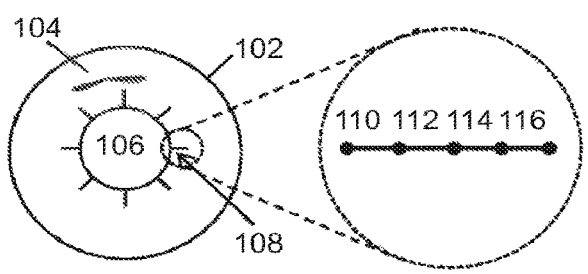

Described herein are methods for isolating the content(s) of a partition, such as a droplet. The methods described herein are useful for isolating target molecule(s) from a mixture that can comprise the contents of one or more partitions. Moreover, the methods described herein may also be useful in the generation of nucleic acid libraries for sequencing. For example, a nucleic acid molecule library (e.g., a sequencing library) may be generated in a plurality of droplets in an emulsion. The contents of the droplets can be released from the droplets, by, for example, destabilizing or breaking the emulsion such that the contents are pooled in a common mixture that includes the nucleic acid molecule library. The nucleic acid molecules in the common mixture can be bound to a plurality of supports. Upon isolating the supports, the nucleic acid molecules can be isolated from the mixture. The nucleic acid molecules can then be washed and the supports isolated in one or more additional cycles, followed by elution of the nucleic acid molecules from the supports. The released nucleic acid molecules can then be further processed and analyzed, such as, for example, sequenced in a nucleic acid sequencing reaction.

Droplets and Emulsions

In one aspect, the methods herein provide for recovering target molecules from a plurality of droplets. In some examples, the methods provide for providing a plurality of droplets having contents that comprise a plurality of target molecules. As used herein, droplets generally refer to small globules of one liquid suspended in a second liquid. Droplets can be formed when two or more immiscible liquids are mixed such as, for example, water and oil. An example of a mixture comprising two or more immiscible liquids is an emulsion, such as a water-in-oil emulsion. The first liquid, which is dispersed in globules, can be referred to as a discontinuous phase, whereas the second liquid, in which the globules are dispersed, can be referred to as a continuous phase or dispersion medium. In some examples, the continuous phase can be a hydrophobic fluid, such as an oil, and the discontinuous phase can be an aqueous phase solution. Such a mixture can be considered a water-in-oil emulsion, wherein aqueous droplets are dispersed in an oil continuous phase. In other cases, an emulsion may be an oil-in-water emulsion. In such an emulsion, the discontinuous phase is a hydrophobic solution (e.g., oil) and the continuous phase is an aqueous solution, wherein droplets of oil are dispersed in an aqueous phase. In some examples, the emulsion may comprise a multiple emulsion. Multiple emulsions can comprise larger fluidic droplets that encompass one or more smaller droplets (i.e., a droplet within a droplet). Multiple emulsions can contain one, two, three, four, or more nested fluids generating increasingly complex droplets within droplets.

An oil of an emulsion may be selected based upon chemical properties, such as, among others molecular structure, content, solvating strength, viscosity, boiling point, thermal expansion coefficient, oil-in-water solubility, water-in-oil solubility, dielectric constant, polarity, water-in-oil surface tension, and/or oil-in-water surface tension. Examples of oils useful in an emulsion (e.g., a water-in-oil emulsion) include, without limitation, fluorinated oils, non-fluorinated oils, alkanes (e.g., hexane, decane, octane, and the like), mineral oils, plant oils, vegetable oils, comestible oils, mineral oil, oleic acid, embryo-tested mineral oil, light mineral oil, heavy mineral oil, PCR mineral oil, AS4 silicone oil, AS 100 silicone oil, AR20 silicone oil, AR 200 silicone oil, AR 1000 silicone oil, AP 100 silicone oil, AP 1000 silicone oil, AP 150 silicone oil, AP 200 silicone oil, CR 200 Silicone oil, DC 200 silicone oil, DC702 silicone oil, DC 710 silicone oil, octanol, decanol, acetophenone, perfluoro-oils, perfluorononane, perfluorodecane, perfluorodimethyl-cylcohexane, perfluoro-1-butanesulfonyl fluoride, perfluoro-1-octanesulfonyl fluoride, perfluoro-1-octanesulfonyl fluoride, nonafluoro-1-butanesulfonyl chloride, nonafluoro-tert-butyl alcohol, perfluorodecanol, perfluorohexane, perfluorooctanol, perfluorodecene, perfluorohexene, perfluorooctene, fuel oil, halocarbon oil 28, halocarbon oil 700, hydrocarbon oil, glycerol, 3M Fluorinert™ fluids (FC-40, FC-43, FC-70, FC-72, FC-77, FC-84. FC-87, FC-3283), oils comprising trifluoroacetic acid, oils comprising hexafluoroisopropanol, Krytox oils (e.g., oils comprising hexafluoropropylene epoxide and/or polymers thereof), oil comprising polyhexafluoropropylene oxide and/or polymers thereof, Krytox GPL oils, oils comprising perfluoropolyether, oils comprising perfluoroalkylether, oils comprising perfluoropolyalkylether, Solvay Galden oils, oils including oils include hydrofluoroethers (e.g., HFE-7500, HFE-7100, HFE-7200, HFE-7600), oils comprising perfluoroalkylamines (e.g., Fluorinert FC-3283 and Fluorinert FC-40), soybean oil, castor oil, coconut oil, cedar oil, clove bud oil, fir oil, linseed oil, safflower oil, sunflower oil, almond seed oil, anise oil, clove oil, cottonseed oil, corn oil, croton oil, olive oil, palm oil, peanut oil, bay oil, borage oil, bergamot oil, cod liver oil, macadamia nut oil, camada oil, chamomile oil, citronella oil, eucalyptus oil, fennel oil, lavender oil, lemon oil, nutmeg oil orange oil, petitgrain oil, rose oil, tarragon oil, tung oil, basil oil, birch oil, black pepper oil, birch tar oil, carrot seed oil, cardamom oil, cassia oil, sage oil, cognac oil, copaiba balsam oil, cypress oil, eucalyptus oil, dillweed oil, grape fruit oil, ginger oil, juniper oil, lavender oil, lovage oil, majoram oil, mandarin oil, myrrh oil, neroli oil, olibanum oil, onion oil, paraffin oil, origanum oil, parsley oil, peppermint oil, pimenta leaf oil, sage oil, rosemary oil, rose oil, sandalwood oil, sassafras oil, spearmint oil, thyme oil, transformer oil, verbena oil, and rapeseed oil. In some examples, a water-in-oil emulsion may comprise one or more of the oils described herein, wherein aqueous droplets are dispersed in the oil(s).

An emulsion may further comprise a surfactant. The surfactant may be a fluorosurfactant. Surfactants are known to stabilize droplets in a continuous phase. Examples of fluorosurfactants useful for stabilizing droplets are described in detail in U.S. Patent Publication 2010-0105112, which is hereby incorporated by reference in its entirety. In some examples, a water-in-oil emulsion may comprise one or more of the oils described herein having one or more surfactants (e.g., fluorosurfactants), wherein aqueous droplets are dispersed in the oil(s).

Droplets may be formed by a variety of methods. Emulsion systems for creating stable droplets in non-aqueous or oil continuous phases are described in detail in, e.g., Published U.S. Patent Publication No. 2010-0105112. In some cases, microfluidic channel networks are particularly suited for generating droplets as described herein. Examples of such microfluidic devices include those described in detail in Provisional U.S. Patent Application No. 61/977,804, filed Apr. 4, 2014, the full disclosure of which is incorporated herein by reference in its entirety for all purposes. Droplets may be formed with a regular periodicity or may be formed with an irregular periodicity. In some aspects, the size and/or shape of the droplet may be determined by the size and shape of a channel in which the droplet is formed.

In some examples, droplets may generally be generated by flowing an aqueous stream into a junction of two or more channels of a microfluidic system into which is also flowing a non-aqueous stream of fluid, e.g., a fluorinated oil, such that aqueous droplets are created within the flowing stream non-aqueous fluid. The aqueous stream can include one or more species such that upon droplet formation, the droplet contents comprise aqueous interiors comprising the one or more species. Additional examples of such species are provided elsewhere herein. The relative amount of species within a droplet may be adjusted by controlling a variety of different parameters of the system, including, for example, the concentration of species in the aqueous stream, the flow rate of the aqueous stream and/or the non-aqueous stream, and the like.

Droplets may have overall volumes that are less than 1000 pL, less than 900 pL, less than 800 pL, less than 700 pL, less than 600 pL, less than 500 pL, less than 400 pL, less than 300 pL, less than 200 pL, less than 100 pL, less than 50 pL, less than 20 pL, less than 10 pL, or even less than 1 pL. Droplets may be monodisperse (i.e., substantially uniform in size) or polydisperse (i.e., substantially non-uniform in size). A plurality of droplets may be generated.

An emulsion may comprise a varied number of droplets depending upon the particular emulsion. For example, an emulsion may comprise at least 10 droplets, at least 50 droplets, at least 100 droplets, at least 500 droplets, at least 1000 droplets, at least 5000 droplets, at least 10,000 droplets, at least 50,000 droplets, at least 100,000 droplets, at least 500,000 droplets, at least 1,000,000 droplets, at least 5,000,000 droplets, at least 10,000,000 droplets, at least 50,000,000 droplets, at least 100,000,000 droplets and upwards.

Contents of Droplets

Droplets can encapsulate one or more species, such as one or more target molecules and/or particles. Put another way, a droplet can be a discrete partition, isolating one or more target molecules and/or particles. Generally, a discontinuous phase can be selected to be compatible with the target molecule(s) and/or particle(s) that are encapsulated. For example, a nucleic acid can be encapsulated in an aqueous droplet (e.g., a buffer). A target molecule can generally refer to a species of particular interest in which further analysis or sequestration of the species is desired. For example a target molecule may be a target nucleic acid molecule. A target nucleic acid molecule may be, for example, single-stranded, partially single-stranded, partially double-stranded, or double-stranded. A target nucleic acid molecule may be any type of nucleic acid with non-limiting examples that include oligonucleotides, nucleotides, DNA, RNA, peptide polynucleotides, complementary DNA (cDNA), double stranded DNA (dsDNA), single stranded DNA (ssDNA), plasmid DNA, cosmid DNA, chromosomal DNA, genomic DNA, viral DNA, bacterial DNA, mtDNA (mitochondrial DNA), mRNA, rRNA, tRNA, nRNA, siRNA, snRNA, snoRNA, scaRNA, microRNA, dsRNA, ribozyme, riboswitch and viral RNA, a locked nucleic acid (LNA) in whole or part, locked nucleic acid nucleotides and any other type of nucleic acid analogue Other non-limiting examples of target molecules include peptides, proteins, small molecules and the like. In some cases a plurality of droplets may comprise a plurality of target molecules, such as a plurality of target nucleic acid molecules. In such cases, the plurality of droplets may be a nucleic acid library, wherein the droplets comprise nucleic acids for sequencing (e.g., a sequencing library).

A droplet may comprise a single target molecule or may comprise e a plurality of target molecules (e.g., target molecules). In some examples, one or more target molecules may be bound to a solid support. For examples, target molecules may be nucleic acids bound to a bead (e.g., polyacrylamide bead). In other examples, a target molecule may be a protein expressed on the surface of a biological cell. Target molecules may be the product of a chemical or biological reaction as described elsewhere herein.

Droplets may comprise any suitable type and/or number of species that can include, but are not limited to, nucleic acids (DNA), proteins, small molecules, peptides, biological cells (e.g., mammalian cells, bacterial cells), and the like. The contents of droplets may also comprise one or more particles, such as, for example beads. A particle may be any form of minute matter, natural or synthetic, that is small enough in size to be encapsulated by a droplet. In further examples, droplets may encapsulate a combination of particles and other species described herein. For example, a droplet may encapsulate a particle coated or bound with one or more additional species, such as, for example, a bead coated with nucleic acids.

In some examples, a droplet may comprise a particle such as bead, including gel beads and other types of beads. In particular, these particles may provide a surface to which reagents are releasably attached, or a volume in which reagents are entrained or otherwise releasably partitioned. These reagents may then be delivered in accordance with a desired method, for example, in the controlled delivery of reagents into droplets. A wide variety of different reagents or reagent types may be associated with the particles, where one may desire to deliver such reagents to a droplet. Non-limiting examples of such reagents include, e.g., enzymes, polypeptides, antibodies or antibody fragments, labeling reagents, e.g., dyes, fluorophores, chromophores, etc., nucleic acids, polynucleotides, oligonucleotides, and any combination of two or more of the foregoing. In some cases, the particles may provide a surface upon which to synthesize or attach oligonucleotide sequences. Various entities including oligonucleotides, barcode sequences, primers, cross-linkers and the like may be associated with the outer surface of a particle. In the case of porous particles, an entity may be associated with both the outer and inner surfaces of a particle. The entities may be attached directly to the surface of a particle (e.g., via a covalent bond, ionic bond, van der Waals interactions, etc.), may be attached to other oligonucleotide sequences attached to the surface of a particle (e.g. adaptor or primers), may be diffused throughout the interior of a particle and/or may be combined with a particle in a partition (e.g. fluidic droplet). In some cases, an entity such as a cell or nucleic acid is encapsulated within a particle. Other entities including amplification reagents (e.g., PCR reagents, primers) may also be diffused throughout the particle or chemically-linked within the interior (e.g., via pores, covalent attachment to polymeric matrix) of a particle. Additional examples of particles that may be useful are described in U.S. Patent Publication 2014-0378345, the full disclosure of which is hereby incorporated by reference in its entirety for all purposes.

A particle may comprise natural and/or synthetic materials, including natural and synthetic polymers. Examples of natural polymers include proteins and sugars such as deoxyribonucleic acid, rubber, cellulose, starch (e.g. amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, Corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly(vinyl acetate), poly(vinyl alcohol), poly(vinyl chloride), poly(vinylidene dichloride), poly(vinylidene difluoride), poly(vinyl fluoride) and combinations (e.g., co-polymers) thereof. Particles may also be formed from materials other than polymers, including lipids, micelles, ceramics, glass-ceramics, material composites, metals, other inorganic materials, and others. In exemplary cases, the particle may comprise polyacrylamide. The polyacrylamide particle may comprise linear polyacrylamide (LPA). In other examples, the particle may comprise agarose.

In certain examples, reagents for one or more chemical or biological reaction can be encapsulated such that a droplet functions as a small reaction chamber in which a chemical or biological reaction(s) may take place. In these examples, the discontinuous phase can be selected to be compatible with the desired chemical or biological reaction(s) (i.e., can provide suitable conditions for the reaction to occur). In the case of a chemical or biological reaction, a droplet may include suitable components for the chemical or biological reaction to take place, such as, for example an enzyme, reactants, any necessary co-factors, etc. Once the reaction(s) takes place, the droplet can also comprise any products/by-products of the reaction(s). The biological reaction can be any number of enzymatic reactions that can be carried out in a droplet.

An example of a biological reaction that may take place in a droplet includes a primer extension reaction that may be useful in a nucleic acid amplification reaction, such as, for example a polymerase chain reaction (PCR). In cases where a primer extension reaction takes place in a droplet, the droplet may comprise components for a primer extension reaction (i.e., template nucleic acid, primers, a polymerase, dNTPs, and the like). In some cases, the contents of the droplets may comprise a polymerase and/or any other enzyme for use in an amplification reaction. In other cases, the contents of the droplets may comprise a primer. In some cases, the primer may comprise a barcode sequence. In some cases, the primers may comprise a random N-mer. Examples of barcoding nucleic acid molecules in droplets are described below. As described elsewhere herein, a target molecule can be a target nucleic acid molecule. The target nucleic acid molecule may act as a template for an amplification reaction. Additional examples of amplification reactions that may be completed in droplets are provided by U.S. patent application Ser. No. 14/316,383, filed Jun. 26, 2014, the full disclosure of which is incorporated herein by reference in its entirety for all purposes.

An example of a chemical reaction that can be conducted within a droplet is the dissolution or degradation of a particle in the droplet, such as a bead. A degradable particle may comprise one or more species with a labile bond such that when the particle/species is exposed to the appropriate stimuli, the bond is broken and the particle degrades. The labile bond may be a chemical bond (e.g., covalent bond, ionic bond) or may be another type of physical interaction (e.g., van der Waals interactions, dipole-dipole interactions, etc.). In some cases, a crosslinker used to generate a particle may comprise a labile bond. Upon exposure to the appropriate conditions, the labile bond is broken and the particle is degraded. For example, a polyacrylamide gel particle may comprise cystamine crosslinkers. Upon exposure of the particle to a reducing agent, the disulfide bonds of the cystamine are broken and the particle is degraded. Accordingly, a droplet may comprise a reducing agent that is capable of dissolving or degrading a particle having one or more disulfide bonds. Moreover, in the case of a polymeric particle, a droplet may comprise polymeric by-products (e.g., polymeric species) of a degraded particle. For example, in the case of a polyacrylamide particle, the droplet may comprise one or more polyacrylamide species, such as linear polyacrylamide (LPA), resulting from degradation of the particle.

Particles may also be degradable, disruptable, or dissolvable spontaneously or upon exposure to one or more stimuli (e.g., temperature changes, pH changes, exposure to chemical species or phase, exposure to light, reducing agent, etc.). In some cases, a particle may be dissolvable, such that material components of the particles are solubilized when exposed to a particular chemical species or an environmental change, such as, for example, temperature, or pH. For example, a gel bead may be degraded or dissolved at elevated temperature and/or in basic conditions. In some cases, a particle may be thermally degradable such that when the bead is exposed to an appropriate change in temperature (e.g., heat), the particle degrades. Degradation or dissolution of a particle bound to a species (e.g., a nucleic acid species) may result in release of the species from the particle.

FIGS. 1A-1G show an example of an amplification reaction that can be performed in a droplet and can be useful for generating a nucleic acid sequencing library in a plurality of droplets. In this example, oligonucleotides that include a barcode sequence are co-partitioned in, e.g., a droplet 102 in an emulsion, along with a sample nucleic acid 104 (e.g., a target nucleic acid molecule). As noted elsewhere herein, the oligonucleotides 108 may be provided on a bead 106 that is co-partitioned with the sample nucleic acid 104, which oligonucleotides can be releasable from the bead 106 (e.g., via degradation of one or more labile bonds of the bead), as shown in FIG. 1A. The oligonucleotides 108 include a barcode sequence 112, in addition to one or more functional sequences, e.g., sequences 110, 114 and 116. For example, oligonucleotide 108 is shown as comprising barcode sequence 112, as well as sequence 110 that may function as an attachment or immobilization sequence for a given sequencing system, e.g., a P5 sequence used for attachment in flow cells of an Illumina Hiseq or Miseq system. As shown, the oligonucleotides also include a primer sequence 116, which may include a random or targeted N-mer for priming replication of portions of the sample nucleic acid 104. Also included within oligonucleotide 108 is a sequence 114 which may provide a sequencing priming region, such as a "read1" or R1 priming region, that is used to prime polymerase mediated, template directed sequencing by synthesis reactions in sequencing systems. In many cases, the barcode sequence 112, immobilization sequence 110 and R1 sequence 114 may be common to all of the oligonucleotides attached to a given bead. The primer sequence 116 may vary for random N-mer primers, or may be common to the oligonucleotides on a given bead for certain targeted applications.

Figure 1B:
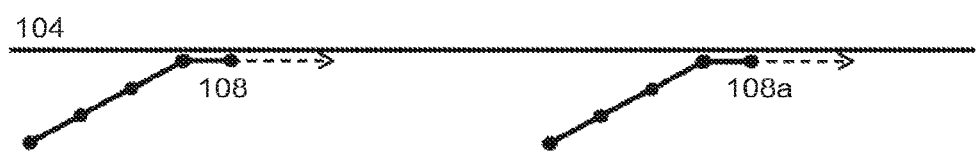
Figure 1C:
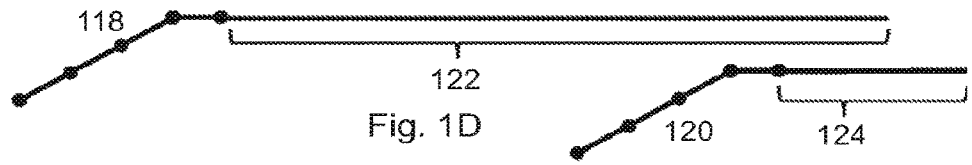

Based upon the presence of primer sequence 116, the oligonucleotides are able to prime the sample nucleic acid as shown in FIG. 1B, which allows for extension of the oligonucleotides 108 and 108a using polymerase enzymes and other extension reagents also co-portioned with the bead 106 and sample nucleic acid 104. As shown in FIG. 1C, following extension of the oligonucleotides that, for random N-mer primers, would anneal to multiple different regions of the sample nucleic acid 104; multiple overlapping complements or fragments of the nucleic acid are created, e.g., fragments 118 and 120. Although including sequence portions that are complementary to portions of sample nucleic acid, e.g., sequences 122 and 124, these constructs are generally referred to herein as comprising fragments of the sample nucleic acid 104, having the attached barcode sequences. As can be appreciated, the replicated portions of the template sequences as described above are often referred to herein as "fragments" of that template sequence. Notwithstanding the foregoing, however, the term "fragment" encompasses any representation of a portion of the originating nucleic acid sequence, e.g., a template or sample nucleic acid, including those created by other mechanisms of providing portions of the template sequence, such as actual fragmentation of a given molecule of sequence, e.g., through enzymatic, chemical or mechanical fragmentation. In some cases, however, fragments of a template or sample nucleic acid sequence can denote replicated portions of the underlying sequence or complements thereof.

Figure 1D:
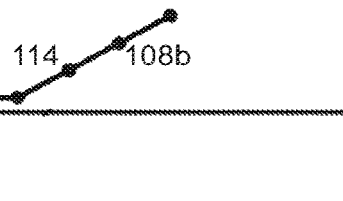
Figure 1E:
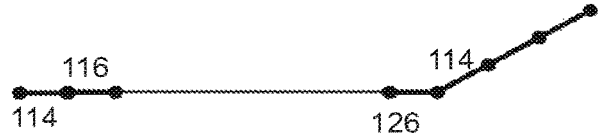
Figure 1F:
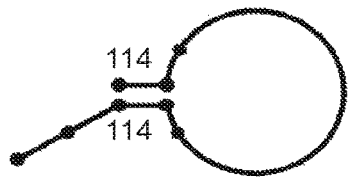

The barcoded nucleic acid fragments may then be subjected to characterization, e.g., through sequence analysis, or they may be further amplified in the process, as shown in FIG. 1D. For example, additional oligonucleotides, e.g., oligonucleotide 108b, also released from bead 106, may prime the fragments 118 and 120. In particular, again, based upon the presence of the random N-mer primer 116b in oligonucleotide 108b (which in many cases may be different from other random N-mers in a given droplet, e.g., primer sequence 116), the oligonucleotide anneals with the fragment 118, and is extended to create a complement 126 to at least a portion of fragment 118 which includes sequence 128, that comprises a duplicate of a portion of the sample nucleic acid sequence. Extension of the oligonucleotide 108b continues until it has replicated through the oligonucleotide portion 108 of fragment 118. As noted elsewhere herein, and as illustrated in FIG. 1D, the oligonucleotides may be configured to prompt a stop in the replication by the polymerase at a desired point, e.g., after replicating through sequences 116 and 114 of oligonucleotide 108 that is included within fragment 118. This may be accomplished by different methods, including, for example, the incorporation of different nucleotides and/or nucleotide analogues that are not capable of being processed by the polymerase enzyme used. For example, this may include the inclusion of uracil containing nucleotides within the sequence region 112 to prevent a non-uracil tolerant polymerase to cease replication of that region. As a result a fragment 126 is created that includes the full-length oligonucleotide 108b at one end, including the barcode sequence 112, the attachment sequence 110, the R1 primer region 114, and the random N-mer sequence 116b. At the other end of the sequence may be included the complement 116' to the random N-mer of the first oligonucleotide 108, as well as a complement to all or a portion of the R1 sequence, shown as sequence 114'. The R1 sequence 114 and its complement 114' are then able to hybridize together to form a partial hairpin structure 128. As can be appreciated because the random N-mers differ among different oligonucleotides, these sequences and their complements would not be expected to participate in hairpin formation, e.g., sequence 116', which is the complement to random N-mer 116, would not be expected to be complementary to random N-mer sequence 116b. This would not be the case for other applications, e.g., targeted primers, where the N-mers would be common among oligonucleotides within a given droplet. By forming these partial hairpin structures, it allows for the removal of first level duplicates of the sample sequence from further replication, e.g., preventing iterative copying of copies. The partial hairpin structure also provides a useful structure for subsequent processing of the created fragments, e.g., fragment 126.

All of the fragments from multiple different droplets may then be pooled (e.g., by collecting droplets and destabilizing the emulsion as described elsewhere herein) for sequencing on high throughput sequencers. Because each fragment is coded as to its droplet of origin, the sequence of that fragment may be attributed back to its origin based upon the presence of the barcode.

As can be appreciated, the example amplification scheme depicted in FIGS. 1A-1G may be completed in any suitable type of partition, including non-droplet partitions, such as microcapsules, wells (e.g., microwells), polymeric capsules, microreactors, micelles, etc.

Additional examples of amplification reactions that can be performed in droplets or other types of partitions, including amplification reactions that can be used to generate nucleic acid libraries for sequencing, are provided in U.S. Provisional Patent Application No. 62/102,420, filed Jan. 12, 2015, which is incorporated herein by reference in its entirety for all purposes.

Releasing Contents of Droplets to Form a Pooled Mixture

Methods described herein provide for releasing the contents of a droplet or a plurality of droplets, such as, for example releasing one or more target molecules from a droplet or plurality of droplets. Generally, the contents of a droplet or a plurality of droplets can contain one or more target molecules and it may be desirable to recover the target molecule(s). A target molecule or target molecules that have been released from a droplet or plurality of droplets are herein referred to as a "released target molecule" or "released target molecules." Releasing can encompass any method by which the contents of a droplet are liberated. Examples of releasing can include breaking the surface of the droplet, making the droplet porous such that the contents can diffuse out of the droplet, or any other method in which the contents of the droplet would be liberated.

In some cases, a droplet or a plurality of droplets can be destabilized (broken) to release the contents of the droplet(s) into a pooled mixture. For example, destabilizing a droplet or plurality of droplets in an emulsion may comprise destabilizing the emulsion. The terms "destabilize," "break," "burst," and "de-emulsify" may be used interchangeably herein. Methods of destabilizing droplets are known to those of skill in the art. Briefly, droplets in an emulsion can be mixed with a destabilization agent that causes the droplet to destabilize and to coalesce. Coalescence of the droplets can result in the generation of a pooled mixture (e.g., a common pool) comprising the contents of the droplets, including target molecules and any other contents of the droplets (e.g., non-target molecules such as enzymes, additional reaction products, reaction by-products reactants, co-factors, buffers, etc.). In general, the pooled mixture is a liquid mixture. Where the droplets are aqueous droplets, the pooled mixture may comprise an aqueous mixture. The pooled mixture may also comprise any amount of continuous phase (e.g., oil) material in which the droplets were originally dispersed surfactants in the continuous phase, and/or the destabilization agent where applicable. For example, in the case of an aqueous droplet or aqueous droplets comprising a degraded polyacrylamide bead and target molecules and originally dispersed in a fluorinated oil, the pooled mixture may comprise one or more of linear polyacrylamide from the degraded beads, the target molecules and the fluorinated oil.

In some examples, a droplet or plurality of droplets may be collected into a vessel and the destabilization agent may be added to the vessel to form the pooled mixture in the vessel. The term "vessel" as used herein means any container that can hold a liquid mixture. A vessel may include, without limitation, a droplet, a tube, a well, a container, a dish, a flask, a beaker, and the like.

The destabilization agent can be any agent that induces droplets of the emulsion to coalesce with one another. The destabilization agent may be present at an amount effective to induce coalescence, which may be selected based, for example, on the volume of the emulsion, the volume of carrier fluid in the emulsion, and/or the total volume of droplets, among others. The amount also or alternatively may be selected, based, for example, on the type of carrier fluid, amount and type of surfactant in each phase, etc. In exemplary embodiments, the destabilization agent can be added to an emulsion, or vice versa, such that the destabilization agent is present in excess over the continuous phase of the emulsion. The ratio of destabilization agent to continuous phase, by volume, may be at least about 1, 2, 3, 4, or 5, among others. In some embodiments, the destabilization agent may be a fluid.

The destabilization agent may be a weak surfactant. Without wishing to be bound by theory, a weak surfactant can compete with droplet surfactant at the oil/aqueous interface causing an emulsion to collapse. In some cases, the destabilization agent is perfluorooctanol (PFO), however, other fluorous compounds with a small hydrophilic group may be used. Other examples of destabilization agents include one or more halogen-substituted hydrocarbons. In some cases, the destabilization agent may be predominantly or at least substantially composed of one or more halogen-substituted hydrocarbons. Each halogen-substituted hydrocarbon may be substituted with one or more halogen substituents provided by the same halogen element (i.e., one or more fluorine, chlorine, bromine, iodine, or astatine substituents) and/or two or more different halogen elements (e.g., at least one fluorine substituent and at least one chlorine substituent, at least one fluorine substituent and at least one bromine substituent, at least one chlorine substituent and at least one bromine substituent, and so on). The halogen-substituted hydrocarbon also optionally may include other non-halogen substituents. In some cases, the halogen-substituted hydrocarbon may have a formula weight of less than about 1000, 500, or 200 daltons, among others. Also or alternatively, the halogen-substituted hydrocarbon may be composed of no more than ten, five, or two carbons. Exemplary halogen-substituted hydrocarbons that may be included in the destabilization agent include chloroform, dichloromethane (methylene chloride), iodomethane, bromochloropropane, or dichlorofluoroethane, among others. The destabilization agent may have a low viscosity and may be capable of denaturing proteins present in the droplets and/or at an interface between the droplets and the carrier fluid. Additional examples of destabilization agents are provided in U.S. Patent Publication No. 2013-018970, the full disclosure of which is incorporated herein by reference for all purposes.

Purifying Target Molecules from a Pooled Mixture

A target molecule(s) partitioned into a droplet(s) may be recovered for use in downstream applications (e.g., target nucleic acid molecules for sequencing). However, the success of downstream applications can be affected by one or more non-target molecules present in the droplets or emulsion comprising the droplets and, thus, a pooled mixture as described above. In some cases, the presence of one or more contaminants in a pooled mixture can negatively impact the success of downstream applications. Therefore, it may be desirable to purify the target molecule(s) from one or more non-target molecule(s) or "contaminants". A "contaminant" as used herein can generally refer to any non-target substance (i.e., chemical, biological, or otherwise) derived from the contents of a droplet or droplets and present in a pooled mixture generated as described elsewhere herein. Contaminants can include, without limitation, one or more oils (e.g., fluorinated oils), salts, biological materials (e.g., nucleic acids, proteins, lipids, etc), surfactants, polymers (e.g., polymers from degraded polymeric particles, such as linear polyacrylamide from a degraded polymeric particle), reactants, destabilization agents, reaction by-products, additional reaction products, enzymes (e.g., polymerases), primers, co-factors and the like. Contaminants can be components of the droplets, components of the partitioning fluids, components of an enzymatic reaction (e.g., PCR reagents, for example, enzymes, primers, dNTPs, and the like), etc.

Target molecules may be purified from contaminants in a pooled mixture by contacting the target molecules with one or more supports and isolating the supports from the pooled mixture. For example, the one or more supports can be provided to the pooled mixture or a vessel (as described elsewhere herein) comprising the pooled mixture. In such cases, the pooled mixture may comprise the contents of one or more droplets and one or more supports. A support generally refers to any species (e.g., a scaffolding or platform) that can selectively bind one or more target molecules in a pooled mixture. In some cases, the support may be solid or, in other cases, the support may be liquid. Moreover, the support may be essentially of any shape, size or material. In some cases, a support may be a particle, such as, for example, a bead.

The support may have one or more surfaces on which target molecules can bind and is generally separable from the pooled mixture. For example, the support may bind a target molecule in a pooled mixture and then the support can be isolated or separated from the non-target molecules such that the target molecule is also separated from the pooled mixture. A target molecule that has been bound to a support can be referred to herein as a "bound target molecule".

Binding of target molecules to a support may be through any suitable means, including ionic interactions, hydrophilic/hydrophobic interactions, van der Waals forces, covalent bonds, non-covalent bonds, etc. Binding of a target molecule to the surface of a support may be specific or non-specific. Binding of a target molecule to a support may be specific for a class of target molecules (e.g., specific for nucleic acid molecules such as DNA). In this example, all or substantially all nucleic acid may be bound to the support. In other examples, the support may bind to a specific species of target molecule. In yet further examples, the support may selectively bind to target molecules of a particular size (e.g., the support may selectively bind to nucleic acids greater than 100 basepairs). The surface of the support may inherently bind to a class of target molecules or the surface of the support may be modified to bind to a class of target molecules.

In some examples, a support may be tailored such that particular target molecules can bind. For example, in the case where a target molecule is a nucleic acid (e.g., DNA, mRNA, etc) the surface of a support can tailored to bind nucleic acids by functionalizing the support with one or more species capable of binding nucleic acids. A variety of methods for modifying the surface of a support such that said surface can bind nucleic acids are known. For instance, the support may be modified by any number of polycations. The polycationic support can be selected from a wide variety of inorganic and organic materials including, but not limited to, metal oxides, glasses, polyamides, polyesters, polyolefins, polysaccharides, polyglycols, and polyaminoacids. In some cases, the support may be a silica bead or silica resin. In some cases, the binding of target nucleic acid molecules to one or more supports may be via one or more ionic interactions.

Supports may be modified with any number of polymers that bind nucleic acids. By way of example, without limitation, polymers that bind nucleic acids include dextran, polyethylene glycol (PEG), polyvinylpyrrolidone (PVP), polysaccharides (e.g., include dextran, ficoll, glycogen, gum arabic, xanthan gum, carageenan, amylose, agar, amylopectin, xylans, beta-glucans, and many others), chemical resins (isocyanate, glycerol, piperidino-methyl, polyDMAP (polymer-bound dimethyl 4-aminopyridine), DIPAM (Diisopropylaminomethyl), aminomethyl, polystyrene aldehyde, tris (2-aminomethyl) amine, morpholino-methyl, BOBA (3-Benzyloxybenzaldehyde), triphenyl-phosphine, and benzylthio-methyl, and others). It should be understood that surfaces modified with polymers or functional groups can, with some exceptions, bind target nucleic acid molecules without regard to nucleic acid sequence. However, methods in which nucleic acids specifically bind to the surface of a support (i.e., sequence-dependent binding) are also contemplated. In these examples, an oligonucleotide probe may be attached (i.e., via chemical modification) to a support. The oligonucleotide probe may contain a sequence of nucleotides that can selectively bind to a target nucleic acid molecule sequence present in the pooled mixture.

Additional examples of functional groups with which a support may be functionalized include, without limitation, alkanes, alkenes, alkynes, diene, alcohols, ethers, aldehydes, ketones, carboxylic acids, esters, amides, amines, nitriles, thiols, silanols, and the like. In some examples, a support may comprise a silica or silica-like (i.e., modified to incorporate silanol on the surface) functionalization. In some cases, the support can bind nucleic acids. In some cases, the surface of the support can be silica-like and the support can bind nucleic acids.

In some instances, it may be desirable to bind other target molecules to the surface of a support. For example, the target molecule may be a small molecule, a protein, a peptide, and the like. In some aspects, the target molecule may be a protein. Methods of binding proteins to solid supports are well known. For example, the surface of the support may be coated with antibodies and the antibodies may recognize a specific epitope of a protein. In another example, the support may be coated with streptavidin and the target protein molecule may contain a biotin molecule. Streptavidin has a high affinity for biotin and is a commonly used method for pulling down proteins modified with biotin moieties. Other suitable examples may include coating the support with a protein that interacts with the target protein, for example, a surface coated with a receptor protein to bind a ligand present in the pooled mixture.

It may be desirable to provide suitable binding conditions to promote binding of a target molecule to a support. A number of factors can affect the conditions suitable for binding a target molecule to a support. Non-limiting examples of such factors include the surface modification of the support, the type of target molecule, and the composition of the pooled mixture (i.e., chemicals, non-target molecules, etc., present in the pooled mixture). In some embodiments, the pooled mixture may comprise one or more additional agents that aid in binding target molecules to supports. Non-limiting examples of such agents include buffer salts, detergents, enzymes, nuclease inhibitors, chelators, organic solvents, and other organic or inorganic substances.

In some examples, an agent that aids in binding target molecules to one or more supports may comprise a chaotropic agent or chaotrope. "Chaotropic agent" and "chaotrope" are used interchangeably herein. Any suitable concentration of chaotropic agent may be used. For example, the concentration of chaotropic agent used may be from about 0.01 molar (M) to about 20 M. In some cases, the concentration of chaotropic agent used may be from about 0.1 M to about 10 M. In some cases, the concentration of chaotropic agent used may be from about 1 M to about 8 M. In some cases, the concentration of chaotropic agent used may be from about 1M to about 5M. In some cases, the concentration of chaotropic agent used may be about 0.01 M, 0.05M, 0.1M, 0.2 M, 0.3 M, 0.4 M, 0.5 M, 1.0 M, 1.5 M, 2.0 M, 2.5 M, 3.0 M, 3.5 M, 4.0 M, 4.5 M, 5.0 M, 5.5 M, 6.0 M, 6.5 M, 7.0 M, 7.5 M, 8.0 M, 8.5 M, 9.0 M, 9.5 M, 10.0 M, 10.5 M, 11.0 M, 11.5 M, 12.0 M, 12.5 M, 13.5 M, 14.0 M, 14.5 M, 15.0 M, 15.5 M, 16.0 M, 16.5 M, 17.0 M, 17.5 M, 18.0 M, 18.5 M, 19.0 M, 19.5 M, 20.0 M or more.

In some cases, the chaotropic agent may comprise a chaotropic salt. Binding of the nucleic acids on a substrate in the presence of chaotropic reagents may be that adsorption of nucleic acids to a substrate lie in disturbances of higher-order structures of the aqueous medium. Such disturbance can lead to adsorption or denaturation of dissolved nucleic acid on the surface of the glass or silica-gel particles. In the presence of chaotropic salts, such adsorption is enhanced. In some examples, binding of target molecules in a pooled mixture may be binding with a silica particle or silica-coated particle in the presence of a chaotropic salt. In such examples, the target molecule may be a nucleic acid. Moreover, in some cases, polyethylene glycol (PEG) may be present in a pooled mixture to aid in the binding of target molecules (e.g., target nucleic acid molecules) to one or more supports.

In some examples, the chaotropic agent is guanidine thiocyanate (GuSCN), however, essentially any chaotropic agent may be used. In other examples, the chaotropic agent is guanidine hydrochloride (GuHCl). Other non-limiting examples of chaotropic agents include, without limitation, urea, sodium perchlorate, lithium perchlorate, lithium acetate, lithium chloride, magnesium chloride, sodium acetate, potassium acetate, potassium chloride, sodium iodide, sodium chloride, ethanol, isopropanol and combinations thereof.

In some cases, a support may comprise at least one component, such as one or more magnetic materials, that is responsive to a magnetic force. In some cases, a support may be entirely magnetic. In some cases, a support may be a magnetic particle, such as a magnetic bead. In such cases, the magnetic particle may be entirely magnetic or may comprise one or more magnetic cores surrounded by one or more additional materials, such as, for example, one or more functional groups and/or modifications for binding one or more target molecules.

In some examples, a support may comprise a magnetic component and a surface modified with one or more silanol groups. Supports of this type may be used for binding target nucleic acid molecules. Silanol-modified magnetic beads are commercially available (AccuBead silica-coated magnetic beads available from Bioneer, silane-modified Dynabeads available from Life Technologies, MagSi beads available from AMSBIO, among others). In some examples, a support may be a magnetic bead or particle and the surface may be functionalized with a plurality of carboxyl groups. Such supports can make use of solid phase reverse immobilization (SPRI) technology. Carboxylated magnetic beads are available from commercial sources, for example, Agencourt AMPure XP SPRI beads available from Beckman-Coulter.

Magnetic materials may be classified according to their magnetic properties. Without wishing to be bound by theory, materials can generally be classified as diamagnetic, paramagnetic, or ferromagnetic. Diamagnetism is a property of all materials and can be a weak magnetic force. When diamagnetism is a magnetic property of a material, the material can be considered "diamagnetic." Diamagnetic materials can create an induced magnetic field in a direction opposite to an externally applied magnetic field. Paramagnetic materials can be attracted by an externally applied magnetic field and form induced magnetic fields in the direction of the applied magnetic field. Ferromagnetic materials are those that can be become permanently magnetized in the presence of a magnetic field. Examples of magnetic materials that may be included in a support include iron, nickel, cobalt, composites thereof and alloys thereof. In some cases, a magnetic material may include one or more iron-oxides, such as magnetite or maghemite.

One or more magnetic supports can be isolated and/or immobilized by applying a magnetic force to the one or more supports (e.g., magnetic separation). A magnetic force can be applied to one or more supports by exposing the one or more supports to an external magnetic field. Such an external magnetic field may be provided by one or more magnetic sources such as, for example, by one or more magnets (e.g., permanent magnetic, electromagnet, etc.). The magnetic responsiveness of a support to a magnetic force can be useful in isolating a support having bound target molecules from a pooled mixture. Application of a magnetic force to the support can result in separation of the support from other components in a pooled mixture. Accordingly, any molecule (e.g., one or more target molecules) that is also bound to the support, covalently or non-covalently, can also be separated from non-bound components in a pooled mixture. When an external magnetic field is applied to a support, the support can be attracted via magnetic force in the direction of the external magnetic field. The source of an external magnetic field, such as one or more magnets, can be positioned such that a support or a plurality of supports is attracted to one or more specific locations. For example, when one or more supports are provided to a pooled mixture in a vessel, the one or more supports may be positioned at one or more locations (e.g., surfaces) of the vessel. For example, a magnetic source can immobilize a support at the bottom of a vessel. In some cases, a magnetic source can immobilize a support on a wall of a vessel.

Magnetic immobilization/separation of one or more supports at multiple positions within a vessel may be used in purification. Magnetic separation at multiple positions within a vessel may occur simultaneously (e.g., one or more supports simultaneously positioned at a plurality of locations within a vessel) or sequentially (e.g., a first round of magnetic separation at a first location, a second round or magnetic separation at a second location, etc.). For example, one or more magnetic supports may be provided to a vessel comprising a liquid pooled mixture comprising contents of one or more destabilized droplets that comprise one or more target molecules. The one or more supports can bind the target molecule(s) to provide a bound target molecule(s). Following binding of target nucleic acid molecules to the one or more supports, the one or more supports can be immobilized at a first location of the vessel via an external magnetic field as described elsewhere herein, thereby separating or isolating the one or more supports (and associated target nucleic acid molecules) from the pooled mixture. For example, an external magnetic field may be applied to the vessel such that a magnetic support comprising a bound target molecule within the vessel is attracted or pulled towards the first location. The first location may be any portion of a wall of the vessel or the bottom of the vessel Immobilized supports may be in the form of a pellet at the bottom or on the wall of a vessel. Generally, an immobilized support can be segregated in a vessel and the movement of the immobilized support can be restricted (e.g., to the bottom of or the wall of a vessel).

Next, the remnant liquid pooled mixture can be removed from the vessel, without removing immobilized support(s) from the vessel. Removal of the liquid pooled mixture from the vessel may be by any method known of removing a liquid from a vessel, including, but not limited to, pipetting, suctioning, decanting, pouring, and the like. A suspension fluid may then be provided to the vessel and the external magnetic field may be removed from the supports, thereby suspending the support in the suspension fluid. A suspension fluid may be any fluid, aqueous or otherwise, that can be used to release the support from an immobilized state. Essentially any fluid may be used as a suspension fluid, although generally, the suspension fluid can be selected such that it is compatible with the support and the target molecule and such that it will not disrupt the binding of the target molecule to the support. In some cases, the suspension fluid may promote the binding of a target molecule to the support. In some examples, the target molecule may be a target nucleic acid molecule and the suspension fluid may comprise a chaotrope (e.g., guanidine thiocyanate or guanidine hydrochloride). In some cases, the suspension fluid may be a washing agent (e.g., ethanol, isopropanol, acetone, etc.) as described elsewhere herein. Suspending a support may involve the addition of a suspension fluid to the vessel and then physically agitating the support, such as by pipetting or vortexing.

The suspended support(s) comprising the bound target molecule(s) may then be immobilized at a second location of the vessel, thereby separating the support(s) and associated bound target molecule(s) from the suspension fluid. The second location of the vessel may be the same location as the first location of the vessel or may be a different than the first location of the vessel. For example, an external magnetic source may be applied to the vessel such that the magnetic support comprising a bound target molecule within the vessel is attracted or pulled towards the second location. The second location may be any portion of a wall of the vessel or may be at the bottom of the vessel Immobilizing a magnetic support at a first location and a different second location may be accomplished by adjusting the location of the applied external magnetic field (e.g., adjusting the positioning of one or more magnetic sources providing the applied external magnetic field). Devices described elsewhere herein may be useful in adjusting the positioning of one or more magnetic sources (and associated external magnetic fields).

One or more magnetic sources may be provided in a device that can receive one or more vessels such that the magnetic source(s) immobilize one or more supports to one or more surfaces of the one or more vessels. The device may comprise one or more holders or receptacles for receiving one or more vessels, where each holder or receptacle is associated with one or more magnetic sources that provide an external magnetic field to each respective vessel. In some cases, such a magnetic source may comprise one or more magnets. In such cases, the one or more magnetic sources may be positioned in such a way that the one or more magnetic supports are drawn towards a particular portion of the vessel (e.g., a surface of the vessel, a wall of the vessel, the bottom of the vessel, etc.). In some cases, a position of a magnetic source in a device may be adjustable such that the external magnetic field generated by the magnetic source can be adjusted to immobilize one or more supports at a variety of locations within a vessel. In some examples, one or more magnetic sources may be included in a sliding rack also a part of a device. In such a configuration, the position of the one or more magnetic sources may be adjusted by moving the sliding rack (e.g., moving the sliding rack up and down) to a desired position. A device may also include a latch or other component suitable for immobilizing a sliding rack at a desired position. A device having an adjustable magnetic source can be useful in cases where magnetic separation at different locations of a vessel, as described elsewhere herein, is desirable. In some cases, a device may comprise a plurality of magnetic sources associated with a receptacle for receiving a vessel, where each of the magnets is positioned at a different location with respect to the receptacle. In some cases, repositioning of a magnetic source and associated external magnetic field within a device may be achieved by repositioning the entire device, such as flipping the device over, rotating the device, etc. In some cases, repositioning of a vessel within a device may, with respect to the vessel, result in repositioning of an applied external magnetic field exerted by a magnetic source of the device. As can be appreciated any suitable combination of repositioning a magnetic source, repositioning of a device comprising a magnetic source, and repositioning a vessel within a device may be used to position supports at multiple locations of a vessel. Moreover, a device may comprise a plurality of receptacles and accompanying magnetic sources such that a plurality of vessels can be processed in parallel. Any suitable number of receptacles and accompanying magnetic sources may be included.

An example device suitable for performing magnetic separations, including those described herein, is schematically depicted in various views in FIGS. 6A-6C. FIGS. 6A and 6B show front (FIG. 6A) and back (FIG. 6B) views of an example magnetic separation device 600. As shown in FIGS. 6A and 6B, magnetic separation device 600 comprises a body 601 that comprises a series of eight receptacles 602 on its top side each capable of receiving a vessel 603. As shown in FIGS. 6A and 6B, a series of vessels 603 may be provided to the device in a single strip, such that each vessel in the strip is positioned to be received by an individual receptacle 602. The bottom side of device 600 also comprises a series of eight receptacles (not shown in FIGS. 6A or 6B) 606 that correspond to receptacles 602 on the top side of magnetic separation device 600. Moreover, as shown in FIG. 6A, the front side of magnetic separation device 600 comprises a series of receptacles 604 that each correspond to one of the receptacles 602. Each of these receptacles is capable of receiving and positioning one or more magnets 605 (e.g., two magnets positioned back-to-back for magnetic device 600). Moreover, as shown in FIG. 6B, magnetic separation device 600 comprises a viewing window 607 for each of the receptacles 602. Such viewing windows 607 can aid in observing a magnetic separation in a vessel placed in a receptacle 602.

FIG. 6C shows a side view of magnetic separation device 600, showing a vessel 603 placed in a receptacle 602. As shown in FIG. 6C, when vessel 603 is placed in receptacle 602, magnets 605 are positioned near or at the bottom of vessel 603. Magnets 605 can exert a magnetic field and apply a magnetic force to magnetic material (e.g., one or more magnetic supports) in vessel 603 such that the magnetic material is immobilized on a wall near or at the bottom of the vessel 603. Moreover, magnetic separation device 600 also comprises receptacles 606 at its bottom side, such that when the device 600 is flipped over (e.g., rotated approximately 180 degrees with respect to the view shown in FIG. 6C), receptacles 606 are then positioned to receive vessels 603. When a vessel 603 is placed in a receptacle 606, magnets 605 are positioned at a higher, different location of vessel 603 than when vessel 603 is placed into receptacle 602. Magnets 605 can exert a magnetic field and apply a magnetic force to magnetic material (e.g., one or more magnetic supports) in vessel 603 such that the magnetic material is immobilized at the higher location of vessel 603.

Figure 6D:
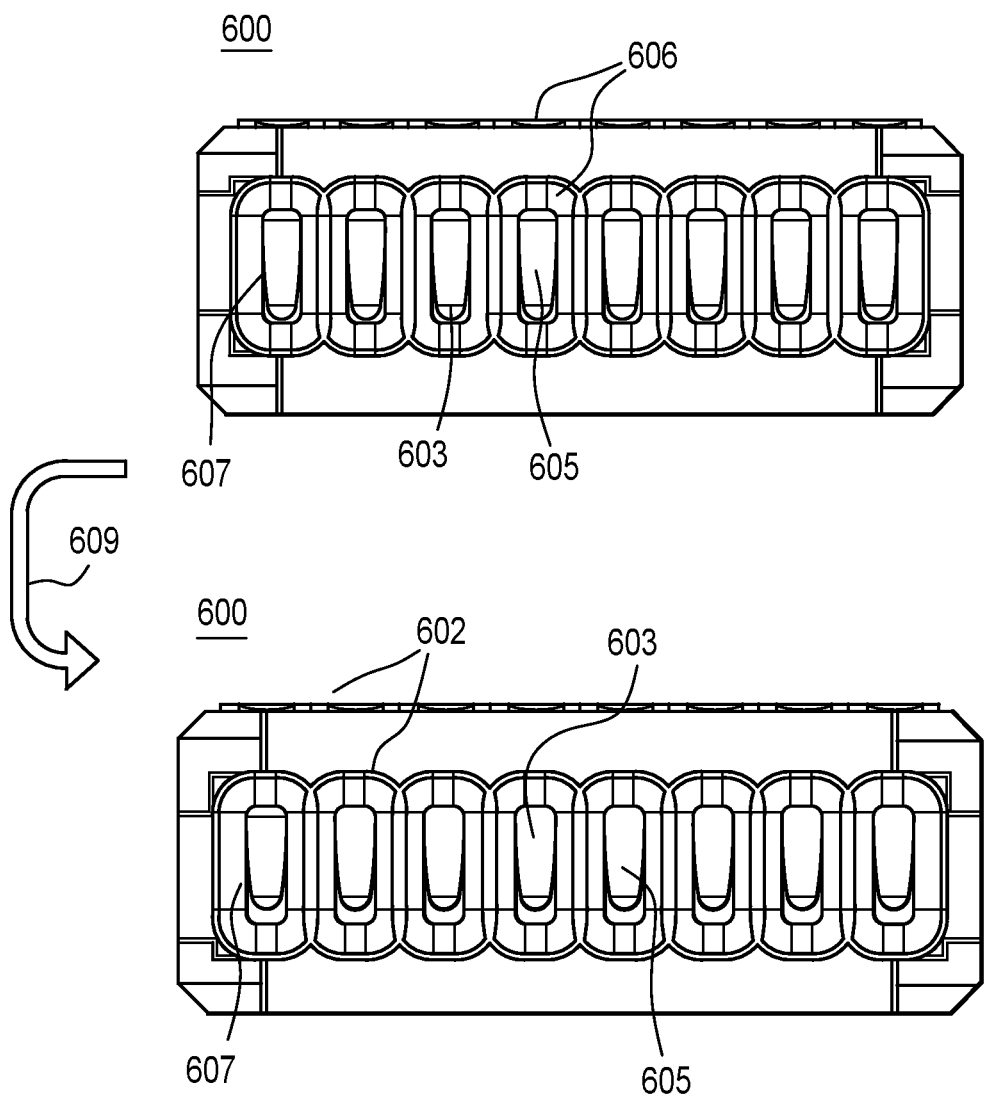
FIG. 6D schematically illustrates an example use of the example magnetic separation device of FIGS. 6A-6C.

FIG. 6D shows an example use of magnetic separation device 600. As shown in FIG. 6D (top panel), magnetic separation device 600 is positioned such that receptacles 606 receive vessels 603. In this orientation of magnetic separation device 600, magnets 605 are positioned at a "high" location of vessels 603. Magnets 605 can exert a magnetic force on magnetic material (e.g., one or more magnetic supports) in vessels 603 such that the magnetic material is immobilized at the "high" location of vessels 603. Magnetic separation in the windows can be observed through viewing windows 607.

The vessels 603 can then be removed from magnetic separation device 600 such that the immobilized magnetic material in vessels 603 is released. Release may be further facilitated by addition of a wash fluid and agitation (e.g., via vortexing or pipetting). Magnetic separation device 600 may be flipped over 609 (e.g., rotated approximately 180 degrees) such that receptacles 602 receive vessels 603, as shown in FIG. 6D (bottom panel). In this orientation of magnetic separation device 600, magnets 605 are positioned at a "low" location (e.g., a location lower than the "high" location of vessels 603, such as at or near the bottom of the vessels) of vessels 603. Magnets 605 can exert a magnetic force on magnetic material (e.g., one or more magnetic supports) in vessels 603 such that the magnetic material is immobilized at the "low" position of vessels 603. Magnetic separation in the windows can be observed through viewing windows 607.

While only magnetic separation device 600 is shown as capable of processing up to eight vessels in parallel, it can be appreciated that magnetic separation device 600 could include any suitable number of receptacles and accompanying magnets for parallel processing of vessels of fewer or greater numbers of vessels.

Another example device suitable for performing magnetic separations, including those described herein, is schematically depicted in FIG. 7. As shown in FIG. 7A, magnetic separation device 700 comprises a series of eight receptacles 701 and a series of eight corresponding receptacles 702 each series capable of receiving vessels 703. When magnetic separation device 700 is in position 700A, receptacles 701 are capable of receiving vessels 703. The vessels 703 are positioned such that they are each in proximity to a set of magnets (e.g., two magnets positioned back-to-back are shown for each set as in FIG. 7C), that are positioned to exert a magnetic force at a "high" position of the vessels 703. Such a force can immobilize magnetic material (e.g., one or more supports) in vessels 703 at the "high" position of the vessels 703. As shown in FIG. 7C, each magnet of a magnet set is housed in magnetic separation device 700 in a recess 705. Additional views (top 710, side 720 and bottom 730) of magnetic separation device 700 (when in position 700A) are shown in FIG. 7B.

Upon flipping magnetic separation device 700 over 706 (e.g., rotating magnetic separation device 700 approximately 180 degrees), magnetic separation device is in position 700B, as shown in FIG. 7A. When magnetic separation device 700 is in position 700B, receptacles 702 are capable of receiving vessels 703. The vessels 703 are positioned to their corresponding set of magnets now positioned to exert a magnetic force at a "low" position of the vessels 703 (e.g., near or at the bottom of vessels 703). Such a force can immobilize magnetic material (e.g., one or more supports) in vessels 703 at the "low" position of the vessels 703.

Figure 8A:
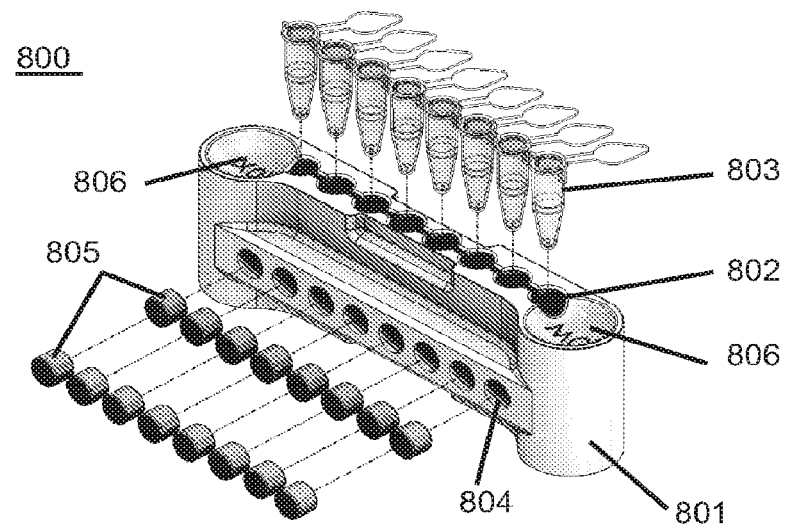
FIGS. 8A and 8B schematically illustrate an alternative example magnetic separation device.
Figure 8B:
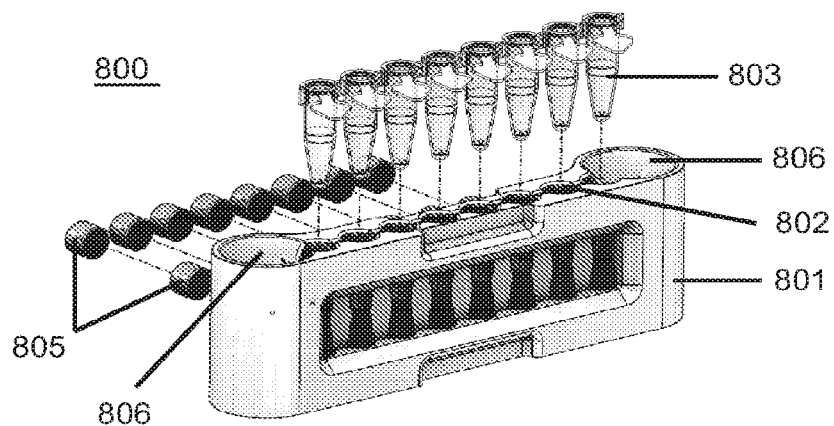

Another example device suitable for performing magnetic separations, including those described herein, is schematically depicted in FIG. 8. As shown in FIG. 8A, magnetic separation device 800 comprises a body 801 and a series of eight corresponding receptacles 802 each series capable of receiving vessels 803. Magnets 805 are included within receptacles 804 as shown in FIG. 8A. Magnetic separation device 800 includes the features and uses as described for the devices of FIGS. 6 and 7. In addition, the magnetic separation device 800 includes scoops 806 to facilitate access and physical manipulation of vessels 803 in use. As shown in FIGS. 8A and 8B, concave scoops 806 can be position at distal ends of body 801 and adjacent to receptacles 803.

Figure 9A:
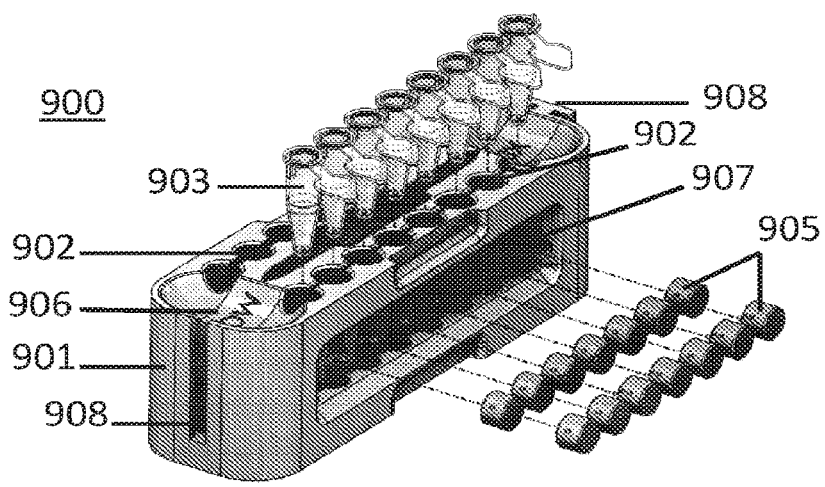
FIGS. 9A-9C schematically illustrate another alternative example magnetic separation device.

Another example device suitable for performing magnetic separations, including those described herein, is schematically depicted in FIG. 9. As shown in FIG. 9A, magnetic separation device 900 comprises two parallel series of eight receptacles 902, for a total of sixteen receptacles each capable of receiving up to sixteen vessels 903. Magnetic separation device 900 includes the features and uses as described for the devices of FIGS. 6, 7 and 8. FIG. 9A additionally shows interlocking ends 908 features for coupling multiple magnetic separation devices 900 in series.

Figure 9B:
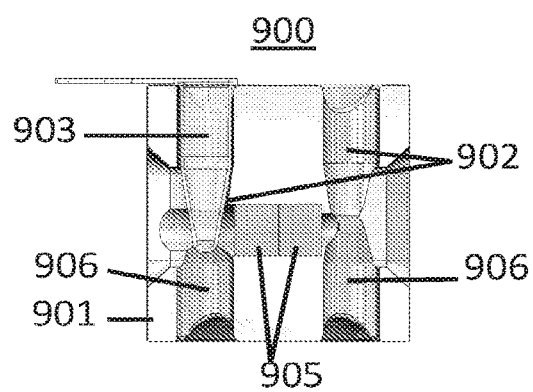

FIG. 9B is a detail schematic of magnetic separation device 900, showing the positioning of receptacles 902 and 906, in relation to vessels 903 and magnets 905 within base 901.

Figure 9C:
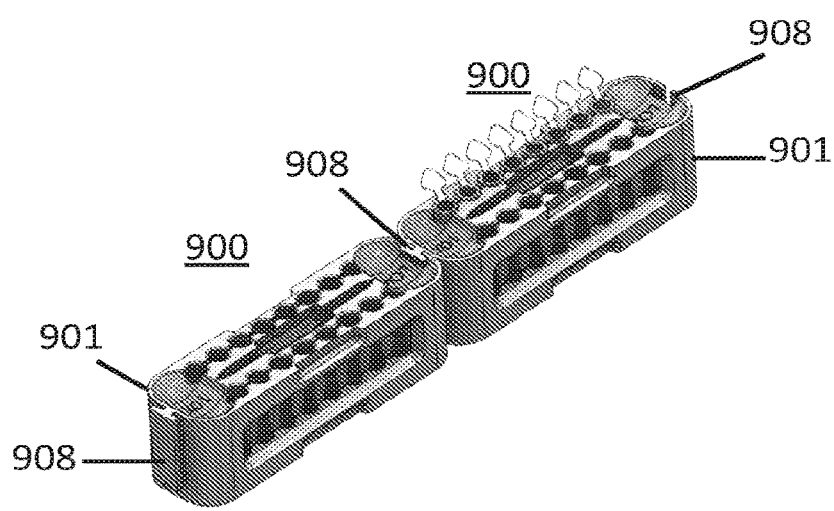

FIG. 9C shows how interlocking ends 908 features can be connected for coupling multiple magnetic separation devices 900 in series.

It should be understood that other methods of separating supports from a pooled mixture can be used. In some examples, one or more supports may be separated using centrifugation. In this case, one or more supports with bound target molecules can be centrifuged such that the supports are pelleted at the bottom of a vessel. Examples of support materials useful for centrifugation separation may include, without limitation, agarose beads, gel beads, glass beads, and the like. Essentially any support with a density greater than the mixture it is contained within can be separated using centrifugation.

After one more supports comprising one or more bound target molecules are separated from a pooled mixture, the non-separated components of the pooled mixture can be removed by, for example, removing the remnant mixture. Any method of removing the non-separated components of the pooled mixture may be used. Such methods of removing may include, without limitation, pipetting, decanting, pouring, suctioning (e.g., by a vacuum), evaporating, sublimating, vaporizing, and the like.

A support that is been separated from a pooled mixture may be washed in one or more cycles to further remove any remaining undesired components associated with the supports. For example, prior to releasing a bound target molecule(s) from one or more supports, the supports may be washed in one or more wash steps by contacting the supports with a washing agent. In general, the supports can be washed with a washing agent that is compatible with both the support and the bound target molecule. The washing agent can be selected such that it does not disrupt the binding of the target molecule(s) to the support(s). For example, washing target nucleic acids bound to a support may be carried out with an alcohol, for example, ethanol or isopropanol. Alternatively, the washing agent may be an organic solvent (e.g., acetone). A washing step may comprise a step of mixing the support with the washing agent (i.e., pipetting the support up and down, vortexing, etc.). In this case, another step of separating may be necessary to separate the support from the washing agent (e.g., reapplying a magnetic field to a vessel to separate magnetic supports from the washing agent, centrifugation, etc.). Any suitable separation method can be utilized including purification methods described herein. In some examples, the supports may not be washed. In some instances, more than one wash step may be desired, e.g., 2, 3, 4, 5, 6, 7, 8, 9, 10, or more wash steps.

Following purification, bound target molecules can be recovered from the one or more supports for downstream applications or for further processing. Recovery can be achieved by releasing or eluting the bound target molecules from the one or more supports. For example, releasing bound target molecules may be may include containing the one or more supports with an elution agent that aids in releasing bound target molecules from the supports. Contacting the one or more supports with elution agent may comprise mixing the supports with the elution agent (e.g., pipetting up and down, vortexing, etc.). An elution agent can be selected such that it can effectively release the bound target molecules from the supports. Non-limiting examples of elution agents include water, Tris buffer, phosphate buffer, and sodium hydroxide. In some cases, bound nucleic acid molecules can be eluted in a buffer of low ionic strength (e.g., TE buffer, or a similar buffer).

In some examples, release of target molecules from one or more supports may be achieved with heating of the supports. The supports may be heated to 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., or 100° C. In some examples, releasing target molecules from supports may comprise adding an elution agent to the supports and then heating the supports.

Target molecules released from supports may be further purified. For example, released target molecules (e.g., target nucleic acid molecules) and from the supports may be subjected to a solid phase reverse immobilization (SPRI) process. For example, released target molecules may be contacted with SPRI beads in a mixture under appropriate binding conditions such that the released target molecules bind to the SPRI beads. In a matter similar to that described elsewhere herein, the SPRI beads containing the bound target molecules may be subjected to an external magnetic field such that the SPRI beads are pulled towards the external magnetic field, thereby separating the SPRI beads from other components of the mixture. The SPRI beads may optionally undergo one or more washing steps as is discussed above. The target molecules can then be released from the SPRI beads via an elution agent and/or heating, as is discussed above.

It can be understood that further purification of one or more target molecules may be optional and can generally be based upon the level of purity desired for downstream applications. In some cases, a single round of purification may be sufficient. For example, a method may comprise binding target molecules to a single plurality of supports (e.g., magnetic particles such as Dynabeads), followed by separation/isolation and any washing of the supports. In some cases, it may be useful to combine a first round of purification and a second round of purification. For example, a method may comprise binding target molecules to a first plurality of supports (e.g., magnetic particles such as Dynabeads), followed by separation/isolation and any washing of the first supports; releasing the target molecules from the first supports; and subsequently binding the target molecules to a second plurality of supports (e.g., magnetic particles such as SPRI beads), followed by separation/isolation and any washing of the second supports. Additional rounds of purification need not be a SPRI process but may comprise any other steps that have been disclosed herein. Moreover, greater than two rounds of purification may be completed, including up to 2, 3, 4, 5, 6, 7, 8, 9, 10, 11, 12, 13, 14, 15, 16, 17, 18, 19 or 20 rounds of purification or more.

As can be appreciated, the purification methods described herein may be used to purify one or more target molecules from any suitable type of partition or plurality of partitions, including non-droplet partitions. A suitable partition can be any partition from which the contents of the partition can be released and/o recovered. Non-limiting examples of such partitions include wells (e.g., microwells), microcapsules, tubes, containers, spots, microreactors, micelles and polymeric capsules. Moreover, the contents of a partition or a plurality of partitions may be released from the partitions and pooled into a pooled mixture. One or more target molecules may be recovered from the pooled mixture using one or more purification methods as described herein.

Further Processing and Analysis of Purified Target Molecules

Target molecules that have been recovered from droplets and purified can subject to further processing and/or analysis. In some cases, purification of target molecules can aid in performing cleaner or more efficient further processing of target molecules. For example, a purified target nucleic acid molecule may function as a template for an amplification reaction, such as polymerase chain reaction or other type of amplification reaction. One or more amplification reactions may be completed using the purified target nucleic acid molecules in order to provide an amplified number of target nucleic acid molecules. Such further processing may be particularly useful where recovered, purified nucleic acid molecules are initially present in low amounts and greater copy numbers are needed for downstream analysis. Moreover, one or more amplification reactions of purified target nucleic acid molecules may be completed in bulk and may be used to add one or more additional sequences (e.g., append additional nucleotides) to the purified target nucleic acid molecules. Such additional sequences can result in the generation of larger nucleic acid molecules (e.g., larger target nucleic acid molecules) and the one or more added sequences may be one or more functional sequences. Non-limiting examples of such functional sequences include a tag, a barcode sequence, an adapter sequence for sequence compatibility with a sequencing instrument/protocol (e.g., P5, P7 Illumina adaptor sequences), a primer (e.g., a random N-mer), a sequencing primer binding site, a sample index sequence, etc. Examples of adding additional sequences to nucleic acid molecules via an amplification reaction (including a bulk amplification reactions) are provided in U.S. patent application Ser. No. 14/316,383, filed Jun. 26, 2014 and U.S. Provisional Patent Application No. 62/102,420, filed Jan. 12, 2015, the full disclosure of which is incorporated herein by reference in its entirety for all purposes.

In some cases, one or more additional sequences may be added to target nucleic acid molecules (or amplified target nucleic acid molecules) via a ligation process to generate larger target nucleic acid molecules. In some cases, the target nucleic acid molecules may be subject to a shearing process in order to generate one or more ends of the target nucleic acid molecules that are suitable for ligation with an additional nucleic acid sequence. The additional nucleic acid sequence may comprise one or more of any of the functional sequences described herein. Examples of shearing and ligation methods that can be used for adding additional sequences to nucleic acid molecules are provided in detail in U.S. Provisional Patent Application No. 62/102,420, filed Jan. 12, 2015, the full disclosure of which is incorporated by reference in its entirety for all purposes. Upon addition of the additional sequence(s) to the target nucleic acid molecules, the larger sequences that are generated can be amplified to provide greater copy numbers. Shearing, ligation and any subsequent amplification can be performed in bulk.

Purified target nucleic acid molecules (that may or may not be further processed) or purified nucleic acid molecules to which one or more additional sequences have been appended (e.g., larger target nucleic acid molecules) may be subject to nucleic acid sequencing, whereby a sequence of the purified target nucleic acid molecules or larger target nucleic acid molecules is determined. The addition of additional functional sequences to purified target nucleic acid molecules may be useful in preparing target nucleic acid molecules for sequencing. Purified target nucleic acid molecules may be prepared for any suitable sequencing platform and sequenced, with appropriate functional sequences added to purified target nucleic acid molecules where needed. Sequencing may be performed via any suitable type of sequencing platform, with non-limiting examples that include Illumina, Ion Torrent, Pacific Biosciences SMRT, Roche 454 sequencing, SOLiD sequencing, etc. As can be appreciated, sequences obtained from nucleic acid molecules can be assembled into larger sequences from which the sequence of the nucleic acid molecules originated. In general, sequencing platforms make use of one or more algorithms to interpret sequencing data and reconstruct larger sequences.

Methods described herein can be used to prepare and sequence a nucleic acid molecule library. In some cases, a library of nucleic acid molecules can be generated, wherein the library comprises a plurality of droplets or other type of partitions comprising the nucleic acid molecules. Examples of preparing a library of nucleic acid molecules in partitions are provided in detail in e.g., U.S. patent application Ser. No. 14/316,383, filed Jun. 26, 2014, U.S. Provisional Patent Application No. 62/017,808, filed Jun. 26, 2014 and U.S. Provisional Patent Application 62/102,420, filed Jan. 12, 2015 (the full disclosures of which are incorporated by reference in their entireties for all purposes). Where the library of nucleic acid molecules comprises a plurality of droplets having the nucleic acid molecules, the plurality of droplets can be destabilized, thereby releasing the nucleic acid molecules from the plurality of droplets into a common pool. The nucleic acid molecules (e.g., target nucleic acid molecules) can be recovered/purified from the common pool using one or more of any of the purification methods described herein. The purified nucleic acid molecules can optionally be subject to further processing as described elsewhere herein and subject to sequencing, whereby the sequences of at least a subset of the purified nucleic acid molecules (or further processed purified nucleic acid molecules) can be determined. Sequencing may be performed via any suitable type of sequencing platform including example platforms described elsewhere herein.

Kits

The disclosure further provides for one or more kits. The one or more kits may comprise the reagents and/or devices sufficient for performing the methods provided in this disclosure. For example, the one or more kits may comprise the reagents and/or devices sufficient for purifying a target nucleic acid molecule from a droplet or other type of partition. Accordingly, the one or more kits may include one or more of the following reagents, without limitation: a destabilization agent, a chaotrope, a washing agent, an elution agent, and a support (e.g., a magnetic support). In some instances, the one or more kits may comprise a device (e.g., a magnetic device) for separating supports from a pooled mixture. In some cases, a kit may comprise reagents suitable for generating an emulsion. Non-limiting examples of such reagents include a continuous phase (e.g., oil) and an aqueous phase (e.g., a buffer). The one or more kits may further comprise packaging (i.e., a box). The reagents and the device may be packaged into a single kit. Alternatively, the reagents and the device may be packaged separately. The kits may further comprise instructions for usage of the kit. These instructions may be in the form of a paper document or booklet contained within the packaging of the kit. Alternatively, the instructions may be provided electronically (i.e., on the Internet).

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Example Workflow

Figure 2:
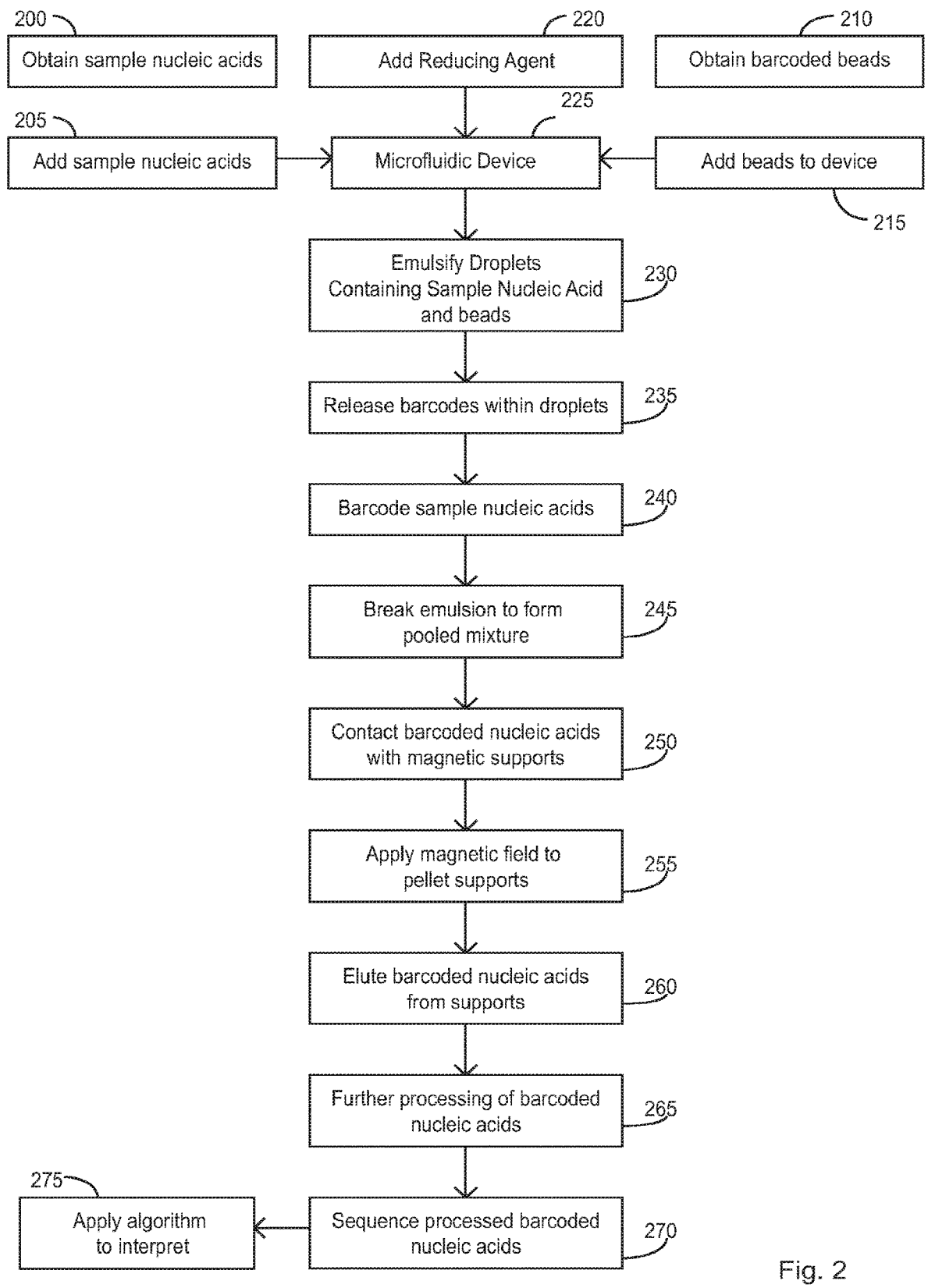
FIG. 2 illustrates an example workflow for performing generating nucleic acid molecules for sequencing as described in Example 1.

FIG. 2 illustrates an example workflow for generating and sequencing a nucleic acid library. As shown in FIG. 2, the example workflow provides for obtaining sample nucleic acids, generating barcoded nucleic acids from the sample nucleic acids, purifying the barcoded nucleic acids, and subsequently sequencing the barcoded nucleic acids. First, a sample comprising nucleic acids may be obtained from a source, 200, and a set of barcoded beads may also be obtained, 210. The beads can be linked to oligonucleotides containing one or more barcode sequences, as well as a primer, such as a random N-mer or other primer. The barcode sequences can be releasable from the barcoded beads, e.g., through cleavage of a linkage between the barcode and the bead or through degradation of the underlying bead to release the barcode, or a combination of the two. For example, in some cases, the barcoded beads can be degraded or dissolved by an agent, such as a reducing agent to release the barcode sequences. In this example, sample comprising nucleic acids, 205, barcoded beads, 215, and optionally other reagents, e.g., a reducing agent, 220, are combined and subjected to partitioning. By way of example, such partitioning may involve introducing the components to a droplet generation system, such as a microfluidic device, 225. With the aid of the microfluidic device 225, a water-in-oil emulsion 230 may be formed, wherein the emulsion contains aqueous droplets that contain sample nucleic acid, 205, reducing agent, 220, and barcoded beads, 215. The reducing agent may dissolve or degrade the barcoded beads, thereby releasing the oligonucleotides with the barcodes and random N-mers from the beads within the droplets, 235. The random N-mers may then prime different regions of the sample nucleic acid, resulting in amplified copies of the sample after amplification (e.g., target nucleic acid molecules), wherein each copy is tagged with a barcode sequence, 240 ("barcoded nucleic acids"). In some cases, each droplet may contain a set of oligonucleotides that contain identical barcode sequences and different random N-mer sequences. Subsequently, the emulsion is broken to form a pooled mixture, 245 in a vessel. A plurality of magnetic supports is contacted with the pooled mixture in the presence of a chaotrope such that the barcoded nucleic acids bind to the magnetic supports, 250. An external magnetic field is applied to the pooled mixture such that the magnetic supports are pelleted, 255. The supernatant is removed and the barcoded nucleic acids are released from the magnetic supports, 260 via the action of one or more elution agents. The process of applying an external magnetic field and pelleting the supports may be repeated for one or more cycles (with the addition and removal of fluid in each cycle) prior to release of the barcoded nucleic acids from the beads. The released barcoded nucleic acids may be subject to further processing, 265. For example, additional sequences (e.g., sequences that aid in particular sequencing methods, additional barcodes, etc.) may be added to the barcoded nucleic acids, via, for example, amplification methods (e.g., PCR or other amplification reaction) and/or ligation methods. Sequencing may then be performed on the barcoded nucleic acids, 270, and one or more algorithms applied to interpret the sequencing data, 275. Sequencing algorithms can be, for example, of performing analysis of barcodes to align sequencing reads and/or identify the sample from which a particular sequence read belongs.

Example 2: Example Purification Methods

Figure 3A:
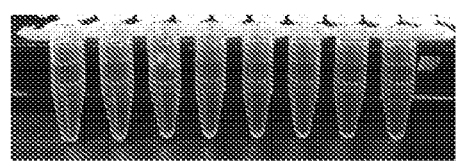
FIGS. 3A-3F illustrate an example method for recovering target molecules from droplets in an emulsion as described in Example 2.
Figure 3B:
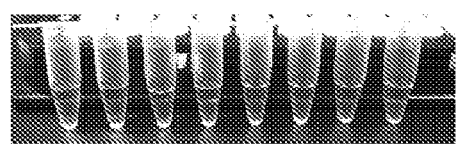

FIGS. 3A-3F provide an example method for purifying target nucleic acid molecules from aqueous droplets in an emulsion using magnetic supports and a magnetic separation device. Aqueous droplets encapsulating a plurality of target nucleic acid molecules in an emulsion were collected into a high profile strip comprising 8 tubes. Each tube in the strip contained an emulsion comprising a plurality of aqeuous droplets in fluorocarbon oil (having a fluorosurfactant) comprising a plurality of target nucleic acid molecules. The droplets had an approximate volume of 360 picoliters (pL). 125 microliters (μL) of perfluorooctanol (PFO) was added to each tube and the strip was vortexed to to destabilize the emulsion and the droplets (FIG. 3A), resulting in the release of the contents of the droplets into a pooled mixture in each tube. The oil/PFO phase separated to the bottom of the tubes/pooled mixtures and the aqueous phase containing the target nucleic acid molecules separated to the top of the tubes/pooled mixtures. 135 μL of the oil/PFO phases was carefully pipetted out of each tube so as not to disrupt the aqueous phase (FIG. 3B). As shown in FIG. 3B, each tube contained a small remnant volume of oil/PFO at its bottom after removal of the 135 μL of the oil/PFO phases.

Figure 3C:
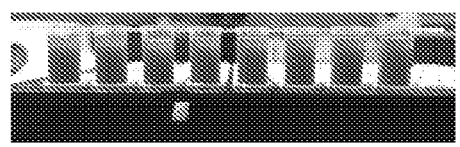
Figure 3D:
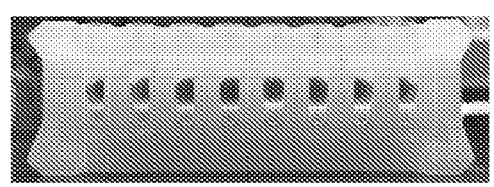
Figure 3E:
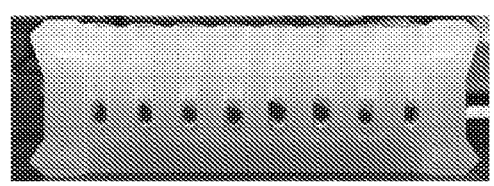
Figure 3F:
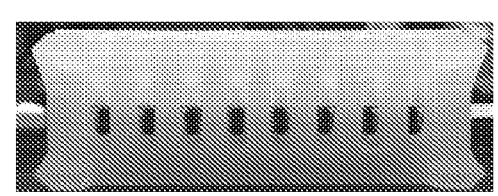

180-200 μL of a mixture comprising 3.5 μg/μL silanized Dynabeads (Life Technologies) and a chaotropic salt (5.5 M), guanidine thiocyanate (GuSCN) were added to each tube and the mixtures were mixed via pipeting to bind target nucleic acid molecules to the Dynabeads (FIG. 3C). After an incubation period of 10 min, the strip of tubes was placed into a magnetic separation device (FIG. 3D). As shown in FIGS. 3D-F, the magnetic separation device comprised a plurality of receptacles each associated with a set of magnets (e.g., two magnets positioned contacting each other back-to-back). Each receptacle was capable of receiving a tube of the strip, such that the strip of tubes was placed in the device and each respective magnet set exerted a magnetic force on Dynabeads in respective tubes. The positioning of the device as a whole determined whether each respective magnet set was in a "high" or "low" position with respect to each receptacle/tube. In a first position of the device, the magnet sets were positioned at a "high" position. After a 4 minute incubation in the magnetic device, the Dynabeads were pulled to the walls of the tubes (high position) such that the Dynabeads were isolated from the pooled mixture. The pooled mixture (e.g.,supernatant) was pipetted out of the tube leaving behind a pellet of Dynabeads attached to each of the walls of the tubes.

The Dynabeads were washed with ethanol (EtOH) and the tubes removed from the device resulting in resuspension of the beads in the EtOH in each tube. After the EtOH wash, the magnetic device was flipped over and the strip of tubes was placed back into the device. At this second position of the device, the magnet sets were positioned at a "low" position. After another 4 minute incubation, the Dynabeads were pulled to bottom walls of the tubes (low position) (FIG. 3E). The EtOH was removed and the Dynabeads were again washed with EtOH. The strip of tubes was once again placed into the second side of the magnetic device such that the Dynabeads were pulled to the bottom of the strip tube (low position) (FIG. 3F). The EtOH wash was removed. The target nucleic acid molecules were eluted off of the Dynabeads with 52 μL of elution buffer comprising 10 mM Tris-HCl buffer at pH 8.5 (FIG. 3F).

The target nucleic acid molecules were optionally further processed with SPRI beads. In this optional step, the target nucleic acid molecules were contacted with SPRI beads in the presence of polyethylene glycol (PEG) to bind the target nucleic acid molecules to the SPRI beads. The SPRI beads underwent another round of magnetic separation and washing steps as described above. The target nucleic acid molecules were eluted from the SPRI beads and collected, subjected to further processing to add additional sequences suitable for Illumina sequencing and sequenced on an Illumina HiSeq 2500 sequencer.

Example 3: Example Purification Methods

To test example one-step purification methods (e.g., purification with only one set of supports) versus an example two-step purification method (e.g., purification with a first set of supports, followed by further purification with a second set of supports), the example methods were compared side-by-side. 2 ng of 20 kb DNA was co-partitioned with barcoded polyacrylamide beads (e.g., beads comprising primers having a barcode sequence and a random N-mer primer sequence as described elsewhere herein) in aqueous droplets within a fluorinated oil continuous phase having a fluorosurfactant using a microfluidic partitioning system (See, e.g., U.S. Patent Application No. 61/977,804, filed Apr. 4, 2014, and incorporated herein by reference in its entirety for all purposes), where the aqueous droplets also included dNTPs, thermostable DNA polymerase and other reagents for carrying out amplification within the droplets, as well as a chemical activator (e.g., reducing agent) for releasing the barcode oligonucleotides from the beads.

Following bead dissolution (e.g., via disruption of disulfide bonds of the beads), the droplets were thermocycled to allow for primer extension of the barcode oligonucleotides against the template of the sample nucleic acids within each droplet. This resulted in the generation of barcoded copy fragments of the sample nucleic acids that included the barcode sequence representative of the originating partition, as described elsewhere herein. Four replicate samples of droplets having barcoded copy fragments were generated.

After generation of the barcoded copy fragments, the emulsion in each sample was destabilized with the addition of perfluorooctanol (PFO). This resulted in destabilization of the droplets and the generation of pooled mixture containing the contents of the droplets in each sample. Purification of the barcoded copy fragments from the pooled mixtures was performed using a magnetic device as described in Example 2 above and using 4 different purification methods, similar to those described in Example 2. Three of the methods (Method 1, Method 2, Method 3) included binding of barcoded copy fragments to varied amounts of single set of Dynabeads in a single purification step, whereas the fourth method included a two-step purification, whereby barcoded copy fragments were bound to a first set of Dynabeads, released and then bound to a second set of SPRI beads. Each of the four samples was processed with one of the four purification methods, where the amount of Dynabeads added was controlled by volume of Dynabead and chaotrope mixture (as in Example 2) added to pooled mixtures. A summary of the methods is as follows:

Method 1: One-step: Dynabeads only (200 µL mixture added) (D 200 µL in FIG. 4A)
Method 2: One-step: Dynabeads only (190 µL mixture added) (D 190 µL in FIG. 4A)
Method 3: One-step: Dynabeads only (180 µL mixture added) (D 180 µL in FIG. 4A)
Method 4: Two-step: Dynabeads (200 µL mixture added) followed by SPRI beads (D 200 µL+SPRI in FIG. 4A)

Figure 4A:
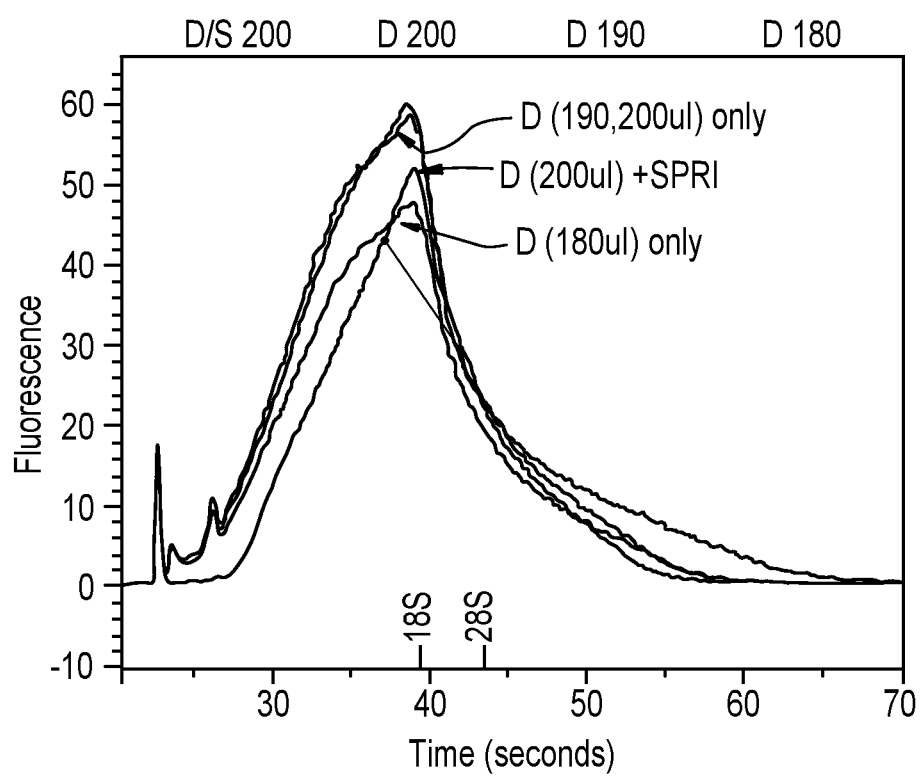
FIG. 4A graphically illustrates product yields obtained from experiments described in Example 3.

Purified barcoded copy fragments were analyzed for yield and those obtained from Methods 1 and 4 were subject to further processing to add appropriate adaptors to the purified barcoded copy fragments for Illumina Sequencing followed by whole genome sequencing (WGS) of the nucleic acid molecules on an Illumina sequencer. Data obtained from the experiments in shown in FIG. 4. FIG. 4A graphically depicts product yields of the various purification methods. Methods 1 and 2 generated higher product yields than Methods 3 and 4, suggesting that a one-step purification method could result in higher yields when compared to a two-step purification method or other one-step purification methods employing a lower amount of Dynabeads. Moreover, Methods 1-4 were effective in lowering linear polyacrylamide (LPA) (e.g., resulting from dissolution of polyacrylamide beads) from the barcoded copy fragments, which aided in further processing of purified copy fragments to add appropriate adaptors for sequencing.

FIG. 4B graphically depicts sequencing data obtained from the experiments and further suggests that a one-step purification method can be comparable to or even an improvement over a two-step method. As shown in FIG. 4B, the table illustrates the results of sequencing on the barcoded, copy amplified fragments of Method 1 and Method 4. Method1 had a higher effective amplification rate and a higher effective barcode diversity as compared to Method 4 and similar unmapped fractions during sequencing.

Example 4: Example Purification Methods

To test an example one-step purification methods (e.g., purification with only one set of supports) versus an example two-step purification method (e.g., purification with a first set of supports, followed by further purification with a second set of supports), the example methods were compared side-by-side. 1 ng of 20 kb DNA was co-partitioned with barcoded polyacrylamide beads (e.g., beads comprising primers having a barcode sequence and a random N-mer primer sequence as described elsewhere herein) in aqueous droplets within a fluorinated oil continuous phase having a fluorosurfactant using a microfluidic partitioning system (See, e.g., U.S. Patent Application No. 61/977,804, filed Apr. 4, 2014, and incorporated herein by reference in its entirety for all purposes), where the aqueous droplets also included dNTPs, thermostable DNA polymerase and other reagents for carrying out amplification within the droplets, as well as a chemical activator (e.g., reducing agent) for releasing the barcode oligonucleotides from the beads.

Following bead dissolution (e.g., via disruption of disulfide bonds of the beads), the droplets were thermocycled to allow for primer extension of the barcode oligonucleotides against the template of the sample nucleic acids within each droplet. This resulted in the generation of barcoded copy fragments of the sample nucleic acids that included the barcode sequence representative of the originating partition, as described elsewhere herein. Six replicate samples of droplets having barcoded copy fragments were generated.

Figure 5:
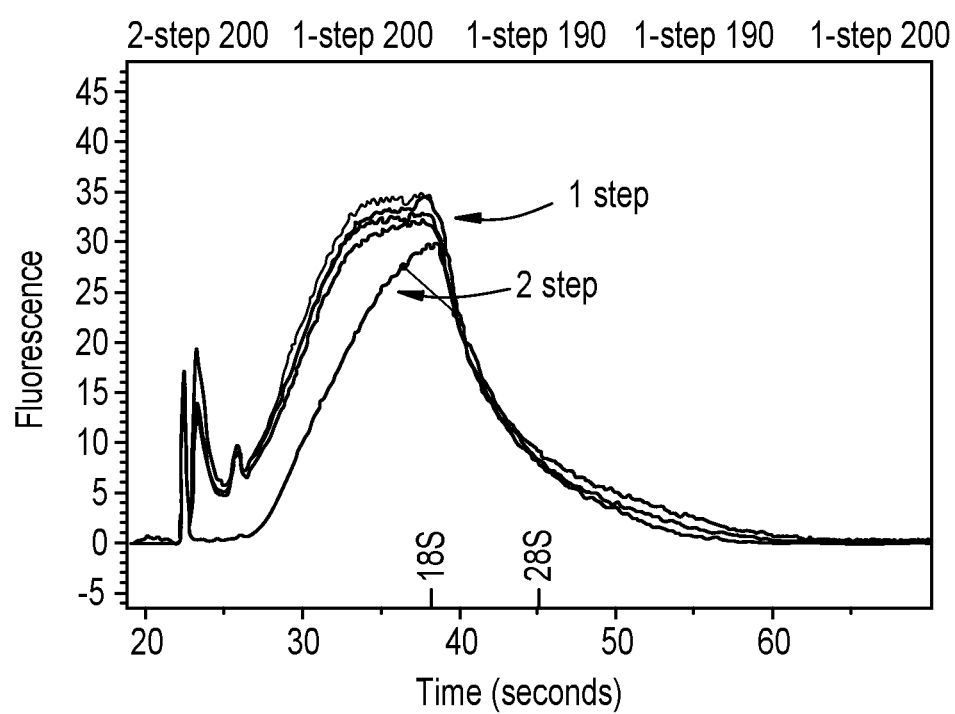
FIG. 5 graphically illustrates product yields obtained from experiments described in Example 4.

After generation of the barcoded copy fragments, the emulsion in each sample was destabilized with the addition of perfluorooctanol (PFO). This resulted in destabilization of the droplets and the generation of a pooled mixture containing the contents of the droplets for each sample. Purification of the barcoded copy fragments from the pooled mixtures was performed using a magnetic device as described in Example 2 above and using 3 different purification methods, similar to those described in Example 2. Two purification methods included binding of barcoded copy fragments to varied volumes of a single set of Dynabeads in a single purification step, whereas the third method included a two-step purification, whereby barcoded copy fragments were bound to a first set of Dynabeads, released and then bound to a second set of SPRI beads. Each of the six samples was processed with one of the three purification methods, where the amount of Dynabeads added was controlled by volume of Dynabead and chaotrope mixture (as in Example 2) added to pooled mixtures. A summary of the methods is as follows:

Method 1: One-step: Dynabeads only (200 µL mixture added)
Method 2: One-step: Dynabeads only (190 µL mixture added)
Method 3: Two-step: Dynabeads (200 µL mixture added) followed by SPRI beads Purified barcoded copy fragments were analyzed for yield. Data obtained from the experiments in shown in FIG. 5. FIG. 5 graphically depicts product yields of the various purification methods. Both one-step methods (Method 1 and 2) generated higher yields than the two-step method (Method 3). The data suggest that a one-step purification method could result in higher yields when compared to a two-step purification method.

Example 5: Example Purification Methods

Genomic DNA from the NA12878 human cell line is subjected to size based separation of fragments using a Blue Pippin DNA sizing system to recover fragments that are approximately 10 kb in length. The size selected sample nucleic acids are then copartitioned with barcoded beads in aqueous droplets within a fluorinated oil continuous phase using a microfluidic partitioning system (See, e.g., U.S. Patent Application No. 61/977,804, filed Apr. 4, 2014, the full disclosure of which is incorporated herein by reference in its entirety for all purposes), where the aqueous droplets also include dNTPs, thermostable DNA polymerase and other reagents for carrying out amplification within the droplets, as well as a chemical activator (e.g., a reducing agent) for releasing the barcode oligonucleotides from the beads. This is repeated both for 1 ng of total input DNA and 2 ng of total input DNA. The barcoded beads are obtained as a subset of a stock library that represents barcode diversity of over 700,000 different barcode sequences. The barcode containing oligonucleotides include additional sequence components and have the general structure:

Bead-P5-BC-R1-Nmer

Where P5 and R1 refer to the Illumina attachment and Read1 primer sequences, respectively, BC denotes the barcode portion of the oligonucleotide, and N-mer denotes a random N-mer priming sequence used to prime the template nucleic acids. See, e.g., U.S. patent application Ser. No. 14/316,383, filed Jun. 26, 2014, the full disclosure of which is hereby incorporated herein by reference in its entirety for all purposes.

Following bead dissolution, the droplets are thermocycled to allow for primer extension of the barcode oligos against the template of the sample nucleic acids within each droplet. Thermocycling results in generation of barcoded copy fragments of the sample nucleic acids that include the barcode sequence representative of the originating partition, in addition to the other included sequences set forth above. Such an amplification reaction is described in more detail elsewhere herein.

After generation of the barcoded copy fragments, the emulsion of droplets including the barcoded copy fragments are destabilized with the addition of a perfluorooctanol (PFO). This results in a pooled mixture containing the contents of the droplets. The pooled mixture is contacted with Dynabeads MyOne Silane Beads (Life Technologies) in the presence of guanidine thiocyanate (GuSCN) to promote the binding of the barcoded copy fragments to the Dynabeads. The vessel containing the pooled mixture is placed into the holder of a magnetic device such that the Dynabeads are pulled to the wall of the vessel. The supernatant is removed and the Dynabeads are washed with 70% ethanol and vortexed to mix. The device is then flipped over and the vessel containing the pooled mixture is placed into the holder of the magnetic device such that the Dynabeads are pulled to the bottom of the vessel. The supernatant (washing agent) is removed. An elution agent is added to the Dynabeads and the mixture is heated to 65° C. to elute the amplified fragments off of the Dynabeads. The eluted barcoded copy fragments are collected, further processed to add any additional functional sequences desired and/or necessary for Illumina sequencing and sequenced on an Illumina sequencer.

In some cases, prior to further processing, the eluted barcoded copy fragments are collected and further purified by contacting the eluted barcoded copy fragments with SPRI beads (Beckman-Coulter) in the presence of polyethylene glycol (PEG) such that the eluted barcoded copy fragments bind to the SPRI beads. The SPRI beads undergo another round of separating (magnetic), washing, separating, and eluting to provide further purified barcoded copy fragments. Following further purification the further purified barcoded copy fragments can be further processed to add any additional sequences desired and/or necessary for Illumina sequencing and sequenced on an Illumina sequencer.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A magnetic separation device comprising:
    (a) a first magnetic source;
    (b) a second magnetic source,
    (c) a first receptacle disposed on a first face of the magnetic separation device, wherein the first receptacle is configured to position a vessel relative to the first magnetic source; and
    (d) a second receptacle disposed on a second face of the device, wherein the second receptacle is configured to position the vessel relative to a second magnetic source;
    wherein the second face of the magnetic separation device is different from the first face of the magnetic separation device, and wherein the second receptacle of the magnetic separation device is different from the first receptacle of the magnetic separation device.

2. The device of claim 1, wherein the device comprises a plurality of the first receptacles.

3. The device of claim 2, wherein the device comprises eight, sixteen, or thirty-two of the first receptacles.

4. The device of claim 3, wherein the device comprises thirty-two of the first receptacles.

5. The device of claim 1, wherein the device comprises a plurality of the second receptacles.

6. The device of claim 5, wherein the device comprises eight, sixteen, or thirty-two of the second receptacles.

7. The device of claim 6, wherein the device comprises thirty-two of the second receptacles.

8. The device of claim 1, wherein the first magnetic source and the second magnetic source are the same magnetic source.

9. The device of claim 1, wherein the first magnetic source and the second magnetic source are different.

10. A system comprising the device of claim 1 and the vessel.

11. The system of claim 10, wherein the vessel is configured to hold a liquid mixture comprising magnetic particles.

12. The system of claim 10, wherein the vessel is positioned in first receptacle, and the first magnetic source is configured to provide a magnetic field that immobilizes the magnetic particles at a first location within the vessel.

13. The system of claim 10, wherein the vessel is positioned in the second receptacle, and the second magnetic source is configured to provide a magnetic field that immobilizes the magnetic particles at a second location within the vessel that is different from the first location.

14. The system of claim 10, wherein the device comprises a plurality of the first receptacles.

15. The system of claim 14, wherein the device comprises eight, sixteen, or thirty-two of the first receptacles.

16. The system of claim 15, wherein the device comprises thirty-two of the first receptacles.

17. The system of claim 10, wherein the device comprises a plurality of the second receptacles.

18. The system of claim 17, wherein the device comprises eight, sixteen, or thirty-two of the second receptacles.

19. The system of claim 10, wherein the system comprises thirty-two of the second receptacles.

20. The system of claim 10, wherein the system comprises a plurality of the vessels.

* * * * *